US010160752B2

(12) United States Patent
Thatcher et al.

(10) Patent No.: US 10,160,752 B2
(45) Date of Patent: Dec. 25, 2018

(54) COMPOSITIONS AND METHODS FOR TREATING ESTROGEN-RELATED MEDICAL DISORDERS

(71) Applicant: THE BOARD OF TRUSTEES OF THE UNIVERSITY OF ILLINOIS, Urbana, IL (US)

(72) Inventors: Gregory R. Thatcher, Chicago, IL (US); Marton Siklos, Chicago, IL (US); Rui Xiong, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 15/382,338

(22) Filed: Dec. 16, 2016

(65) Prior Publication Data

US 2017/0114052 A1    Apr. 27, 2017

Related U.S. Application Data

(63) Continuation of application No. 14/438,361, filed as application No. PCT/US2013/066702 on Oct. 24, 2013, now abandoned.

(60) Provisional application No. 61/809,101, filed on Apr. 5, 2013, provisional application No. 61/718,035, filed on Oct. 24, 2012.

(51) Int. Cl.

| C07D 409/12 | (2006.01) |
| C07D 333/56 | (2006.01) |
| C07D 333/64 | (2006.01) |
| C07D 409/04 | (2006.01) |
| C07D 409/08 | (2006.01) |
| C12Q 1/48 | (2006.01) |
| G01N 33/574 | (2006.01) |

(52) U.S. Cl.
CPC ......... *C07D 409/12* (2013.01); *C07D 333/56* (2013.01); *C07D 333/64* (2013.01); *C07D 409/04* (2013.01); *C07D 409/08* (2013.01); *C12Q 1/485* (2013.01); *G01N 33/57484* (2013.01); *G01N 2333/91205* (2013.01)

(58) Field of Classification Search
CPC .................................................. C07D 409/12
See application file for complete search history.

(56) References Cited

U.S. PATENT DOCUMENTS

| 5,514,703 | A | * | 5/1996 | Carlson ................ A61K 31/381 |
| | | | | 514/443 |
| 5,962,475 | A | | 10/1999 | Schmid et al. |
| 5,994,547 | A | | 11/1999 | Hoard et al. |
| 6,096,781 | A | | 8/2000 | Cullinan |
| 6,291,484 | B1 | | 9/2001 | Bryant et al. |

| 2011/0312925 | A1 | 12/2011 | Labrie |
| 2015/0284357 | A1 | 10/2015 | Thatcher et al. |
| 2015/0291552 | A1 | 10/2015 | Thatcher et al. |

FOREIGN PATENT DOCUMENTS

| EP | 0827959 | 3/1998 | |
| EP | 0905132 | 3/1999 | |
| EP | 0920862 | 6/1999 | |
| EP | 1336602 | 8/2003 | |
| WO | WO-9510513 A1 * | 4/1995 | ........... C07D 231/12 |
| WO | WO 98/56812 | 12/1998 | |
| WO | WO-9925706 A1 * | 5/1999 | ........... A61K 31/381 |
| WO | WO 2011/140198 | 11/2011 | |
| WO | WO 2014/066692 | 5/2014 | |
| WO | WO 2014/066695 | 5/2014 | |

OTHER PUBLICATIONS

Dorwald F. A. Side Reactions in Organic Synthesis, 2005, Wiley: VCH, Weinheim p. IX of Preface p. 1-16.*
Zirka "Catalytic hydrogenation of benzothiophene to 2,3-dihydrobenzothiophene." Reaction Kinetics and Catalysis Letters, 1983, 23(1-2), 7-12.*
Block, E. "Product Subclass 13: 2,3-Dihydrothiophenes and Derivatives" Section 33.1.13 in Science of Synthesis, vol. 33: Houben-Weyl Methods of Molecular Transformations, Molander, G. A. editor.: 2007, 203-234.*
Bradley "Synergistic methodologies for the synthesis of 3-aroyl-2-arylbenzo[b]thiophene-based selective estrogen receptor modulators. Two concise syntheses of raloxifene" Tetrahedron Letters 1999, 40(28), 5155-5159.*
Toader "Nitrosation, Nitration, and Autoxidation of the Selective Estrogen Receptor Modulator Raloxifene by Nitric Oxide, Peroxynitrite, and Reactive Nitrogen/Oxygen Species" Chemical Research in Toxicology 2003, 16(10), 1264-1276.*
Extended European Search Report for Application No. 17158707.4 dated Apr. 7, 2017 (9 pages).
European Examination Report for Application No. 13848425.8 dated Jun. 7, 2017 (4 pages).
Abdelhamid, R. et al., "Benzothiophene Selective Estrogen Receptor Modulators Provide Neuroprotection by a novel GPR30-dependent Mechanism," ACS Chem Neurosci, 2011, 2:256-68.
Abdul-Hay, S. et al., "NO-SSRIs: Nitric Oxide Chimera Drugs Incorporating a Selective Serotonin Reuptake Inhibitor," ACS Med Chem Lett, 2011, 2, 656.
Abdul-Hay, S.O. et al., "NO-flurbiprofen reduces amyloid-beta, is neuroprotective in cell culture, and enhances cognition in response to cholinergic blockade," J Neurochem, 2009, 111, 766.
Agnusdei, D. et al., "Raloxifene: results from the MORE study," J Musculoskelet Neuronal Interact, 2000, 1, 127.
Antonicelli, R. et al., "Prevention of cardiovascular events in early menopause: a possible role for hormone replacement therapy," Int J Cardiol, 2008, 130, 140.
Arlt, S. et al., "Dimethylarginines, homocysteine metabolism, and cerebrospinal fluid markers for Alzheimer's disease," J Alzheimers Dis, 2012, 31, 751.

(Continued)

*Primary Examiner* — David K O'Dell
(74) *Attorney, Agent, or Firm* — Michael Best & Friedrich LLP

(57) ABSTRACT

Disclosed is a compound of formula (I). or a pharmaceutically acceptable salt thereof. Also disclosed are pharmaceutical compositions including the compound of formula (I) and methods of using the compound of formula (I).

3 Claims, 9 Drawing Sheets

(56) References Cited

OTHER PUBLICATIONS

Assender, J.W. et al., "Protein kinase C isoform expression as a predictor of disease outcome on endocrine therapy in breast cancer," Journal of Clinical Pathology, 2007, 60:1216-21.
Ba, F. et al., "The neuroprotective effects of estrogen in SK—N—SH neuroblastoma cell cultures," Neurochem Int, 2004, 44, 401.
Barrett-Connor, E. et al., "Effects of raloxifene on cardiovascular events and breast cancer in postmenopausal women," N Engl J Med, 2006, 355, 125.
Bartus, R.T. et al., "The cholinergic hypothesis of geriatric memory dysfunction," Science, 1982, 217, 408.
Bennet, B.M. et al., "Cognitive deficits in rats after forebrain cholinergic depletion are reversed by a novel NO mimetic nitrate ester," Neuropsychopharmacology, 2007, 32, 505.
Black, L.J. et al., "Raloxifene (LY139481 HCI) prevents bone loss and reduces serum cholesterol without causing uterine hypertrophy in ovariectomized rats," J Clin Invest, 1994, 93:63-9.
Brinton, R.D., "The healthy cell bias of estrogen action: mitochondrial bioenergetics and neurological implications," Trends Neurosci, 2008, 31, 529.
Burke, T.W. et al., "Arzoxifene as therapy for endometrial cancer," Gynecol Oncol, 2003, 90:S40-6.
Buzdar, A. et al., "Phase II, randomized, double-blind study of two dose levels of arzoxifene in patients with locally advanced or metastatic breast cancer," J Clin Oncol, 2003, 21:1007-14.
Cantara, S., "TAT-BH4 counteracts Abeta toxicity on capillary endothelium," FEBS Lett, 2007, 581, 702.
Carlson, L.E. et al., "Steroid hormones, memory and mood in a healthy elderly population," Psychoneuroendocrinology, 1998, 23, 583.
Castoria, G., et al., "PI3-kinase in concert with Src promotes the S-phase entry of oestradiol-stimulated MCF-7 cells," EMBO J, 2001, 20:6050-9.
Catherino, W.H. et al., "Increasing the number of tandem estrogen response elements increases the estrogenic activity of a tamoxifen analogue," Cancer Letters, 1995, 92:39-47.
Chan, Y.C. et al., "Raloxifene improves vascular reactivity in pressurized septal coronary arteries of ovariectomized hamsters fed cholesterol diet," Pharmacol Res, 2012, 65, 182.
Chisamore, M.J. et al., "Novel Antitumor Effect of Estradiol in Athymic Mice Injected with a T47D Breast Cancer Cell Line Overexpressing Protein Kinase Calpha," Clinical Cancer Research, 2001, 7:3156-65.
Ciriza, I. et al., "Selective estrogen receptor modulators protect hippocampal neurons from kainic acid excitotoxicity: differences with the effect of estradiol," J Neurobiol, 2004, 61, 209.
Clegg, N.J. et al., "ARN-509: A Novel Antiandrogen for Prostate Cancer Treatment," Cancer Research, 2012, 72:1494-503.
Cohen, F.J. et al., "Uterine effects of 3-year raloxifene therapy in postmenopausal women younger than age 60," Obstet Gynecol, 2000, 95, 104.
Colton, C.A. et al., "NO synthase 2 (NOS2) deletion promotes multiple pathologies in a mouse model of Alzheimer's disease," Proc Natl Acad Sci U S A, 2006, 103, 12867.
Delmas, P.D. et al., "Effects of raloxifene on bone mineral density, serum cholesterol concentrations, and uterine endometrium in postmenopausal women," N Engl J Med, 1997, 337, 1641.
Dempsey, E.C. et al., "Protein kinase C isozymes and the regulation of diverse cell responses," American Journal of Physiology—Lung Cellular and Molecular Physiology, 2000, 279:L429-L38.
Dennis, M.K. et al., "In vivo effects of a GPR30 antagonist," Nat Chem Biol, 2009, 5, 421.
Dubal, D.B. et al., "Estradiol Modulates bcl-2 in Cerebral Ischemia: A Potential Role for Estrogen Receptors," J. Neurosci, 1999, 19, 6385.
Ellis, M.J. et al., "Lower-Dose vs High-Dose Oral Estradiol Therapy of Hormone Receptor-Positive, Aromatase Inhibitor-Resistant Advanced Breast Cancer," JAMA: The Journal of the American Medical Association, 2009, 302:774-80.

Fan, L. et al., "Estrogen affects levels of Bcl-2 protein and mRNA in medial amygdala of ovariectomized rats," J Neurosci Res, 2008, 86, 3655.
Ferlazzo, N. et al., "The 894G > T (Glu298Asp) variant in the endothelial NOS gene and MTHFR polymorphisms influence homocysteine levels in patients with cognitive decline," Neuromolecular Med, 2011, 13, 167.
Figtree, G.A. et al., "Raloxifene acutely relaxes rabbit coronary arteries in vitro by an estrogen receptor-dependent and nitric oxide-dependent mechanism," Circulation, 1999, 100, 1095.
Fisher, B. et al., "Endometrial Cancer in Tamoxifen-Treated Breast Cancer Patients: Findings From the National Surgical Adjuvant Breast and Bowel Project (NSABP) B-14," Journal of the National Cancer Institute, 1994, 86:527-37.
Foxton, R.H. et al., "Tetrahydrobiopterin availability in Parkinson's and Alzheimer's disease; potential pathogenic mechanisms," Neurochem Res, 2007, 32, 751.
Fuchs-Young, R. et al., "Raloxifene is a tissue-selective agonist/antagonist that functions through the estrogen receptor," Ann N Y Acad Sci, 1995, 761:355-60.
Galea, L.A. et al., "Gonadal hormone modulation of hippocampal neurogenesis in the adult," Hippocampus, 2006, 16, 225.
Galea, L.A., "Gonadal hormone modulation of neurogenesis in the dentate gyms of adult male and female rodents," Brain Res Rev, 2008, 57, 332.
Garthwaite, G. et al., "Signaling from blood vessels to CNS axons through nitric oxide," J Neurosci, 2006, 26, 7730.
Gibbs, R.B. et al., "Effects of raloxifene and estradiol on hippocampal acetylcholine release and spatial learning in the rat," Psychoneuroendocrinology, 2004, 29, 741.
Gibbs, R.B., "Estrogen therapy and cognition: a review of the cholinergic hypothesis," Endocr Rev, 2010, 31, 224.
Gibbs, R.B., "Long-term treatment with estrogen and progesterone enhances acquisition of a spatial memory task by ovariectomized aged rats," Neurobiol Aging, 2000, 21, 107.
Gkaliagkousi, E. et al., "Nitric oxide signalling in the regulation of cardiovascular and platelet function," Front Biosci, 2011, 16, 1873.
Goekoop, R. et al., "Raloxifene exposure enhances brain activation during memory performance in healthy elderly males; its possible relevance to behavior," NeuroImage, 2005, 25, 63.
Goekoop, R. et al., "Raloxifene Treatment Enhances Brain Activation during Recognition of Familiar Items: a Pharmacological fMRI Study in Healthy Elderly Males," Neuropsychopharmacology, 2005, 31, 1508.
Grese, T.A. et al., "Molecular determinants of tissue selectivity in estrogen receptor modulators," Proc Natl Acad Sci U S A, 1997, 94:14105-10.
Grese, T.A. et al., "Structure-activity relationships of selective estrogen receptor modulators: modifications to the 2-arylbenzothiophene core of raloxifene," J Med Chem, 1997, 40:146-67.
Grohe, C. et al., "17 Beta-estradiol regulates nNOS and eNOS activity in the hippocampus," Neuroreport, 2004, 15, 89.
Hammond, R. et al., "GPR30 is positioned to mediate estrogen effects on basal forebrain cholinergic neurons and cognitive performance," Brain Res, 2011, 1379, 53.
Hochner-Celnikier, D., "Pharmacokinetics of raloxifene and its clinical application," Eur J Obstet Gynecol Reprod Biol, 1999, 85:23-9.
Hopper, R.A. et al., "Tonic and phasic nitric oxide signals in hippocampal long-term potentiation," J Neurosci, 2006, 26, 11513.
Ingle, J., "Estrogen as therapy for breast cancer," Breast Cancer Res, 2002, 4:133-6.
Ingle, J.N. et al., "Randomized Clinical Trial of Diethylstilbestrol versus Tamoxifen in Postmenopausal Women with Advanced Breast Cancer," New England Journal of Medicine, 1981, 304:16-21.
Ingle, J.N., "Sequencing of Endocrine Therapy in Postmenopausal Women with Advanced Breast Cancer," Clinical Cancer Research, 2004, 10:362s-7s.
Jacobsen, D.E. et al., "Raloxifene improves verbal memory in late postmenopausal women: a randomized, double-blind, placebo-controlled trial," Menopause, 2009.

(56) References Cited

OTHER PUBLICATIONS

Jans, D.M. et al., "Processing of amyloid precursor protein as a biochemical link between atherosclerosis and Alzheimer's disease," Cardiovasc Hematol Disord Drug Targets, 2006, 6, 21.
Jeynes, B. et al., "Significant negative correlations between capillary expressed eNOS and Alzheimer lesion burden," Neurosci Lett, 2009, 463, 244.
Jordan, V.C. et al., "The St. Gallen Prize Lecture 2011: Evolution of long-term adjuvant anti-hormone therapy: consequences and opportunities," The Breast, 2011, 20, Supplement 3:S1-S11.
Kelly, M.J. et al., "Rapid actions of plasma membrane estrogen receptors," Trends in Endocrinology and Metabolism, 2001, 12:152-6.
Kennedy, B.J., "Massive estrogen administration in premenopausal women with metastatic breast cancer," Cancer, 1962, 15:641-8.
Khorram, O. et al., "Endometrial and myometrial expression of nitric oxide synthase isoforms in pre- and postmenopausal women," J Clin Endocrinol Metab, 1999, 84, 2226.
Kokiko, O.N. et al., "Administration of raloxifene reduces sensorimotor and working memory deficits following traumatic brain injury," Behav Brain Res, 2006, 170, 233.
Kramar, E.A. et al., "Cytoskeletal changes underlie estrogen's acute effects on synaptic transmission and plasticity," J Neurosci, 2009, 29, 12982.
Larson, J. et al., "Role of N-methyl-D-aspartate receptors in the induction of synaptic potentiation by burst stimulation patterned after the hippocampal theta-rhythm," Brain Res, 1988, 441, 111.
Larson, J.et al., "Alterations in synaptic transmission and long-term potentiation in hippocampal slices from young and aged PDAPP mice," Brain Res, 1999, 840, 23.
Leblanc, E.S. et al., "Hormone replacement therapy and cognition: systematic review and meta-analysis," JAMA, 2001, 285, 1489.
Lewis, J.S. et al., "Estrogen-induced apoptosis in a breast cancer model resistant to long-term estrogen withdrawal," The Journal of Steroid Biochemistry and Molecular Biology. 2005;94:131-41.
Liu, H. et al., "Apoptotic Action of 17β-Estradiol in Raloxifene-Resistant MCF-7 Cells In Vitro and In Vivo," Journal of the National Cancer Institute, 2003, 95:1586-97.
Liu, H. et al., "Bioactivation of the selective estrogen receptor modulator desmethylated arzoxifene to quinoids: 4'-fluoro substitution prevents quinoid formation," Chem Res Toxicol, 2005, 18:162-73.
Liu, H. et al., "Chemical modification modulates estrogenic activity, oxidative reactivity, and metabolic stability in 4'F-DMA, a new benzothiophene selective estrogen receptor modulator," Chem Res Toxicol, 2006, 19:779-87.
Liu, H. et al., "Uterine peroxidase-catalyzed formation of diquinone methides from the selective estrogen receptor modulators raloxifene and desmethylated arzoxifene," Chem Res Toxicol, 2007, 20, 1676-84.
Lonne, G. et al., "PKCalpha expression is a marker for breast cancer aggressiveness," Molecular Cancer, 2010, 9:76.
Lønning, P.E. et al., "High-dose estrogen treatment in postmenopausal breast cancer patients heavily exposed to endocrine therapy," Breast Cancer Research and Treatment, 2001, 67:111-6.
Luiking, Y.C. et al., "Arginine de novo and nitric oxide production in disease states," Am J Physiol Endocrinol Metab, 2012, 303, E1177.
Mackay, H.J. et al., "Protein kinase C: a target for anticancer drugs?," Endocrine-Related Cancer, 2003, 10:389-96.
Maki, P.M. et al., "Hormone therapy and cognitive function," Hum Reprod Update 2009, 15, 667.
Maki, P.M. et al., "Longitudinal effects of estrogen replacement therapy on PET cerebral blood flow and cognition," Neurobiol Aging, 2000, 21, 373.
Maki, P.M., "Hormone therapy and cognitive function: is there a critical period for benefit?," Neuroscience, 2006, 138, 1027.
Meyer, M.R. et al., "Deletion of G protein-coupled estrogen receptor increases endothelial vasoconstriction," Hypertension, 2012, 59, 507.
Mufson, E.J. et al., "Mild cognitive impairment: pathology and mechanisms," Acta Neuropathol, 2012, 123, 13.
Nilsen, J. et al., "Dual action of estrogen on glutamate-induced calcium signaling: mechanisms requiring interaction between estrogen receptors and src/mitogen activated protein kinase pathway," Brain Res, 2002, 930, 216.
Nilsen, J. et al., "Mechanism of estrogen-mediated neuroprotection: regulation of mitochondrial calcium and Bcl-2 expression," Proc Natl Acad Sci U S A, 2003, 100, 2842.
Oddo, S. et al., "Triple-transgenic model of Alzheimer's disease with plaques and tangles: intracellular Abeta and synaptic dysfunction," Neuron, 2003, 39, 409.
O'Regan, R.M. et al., "Effects of the Antiestrogens Tamoxifen, Toremifene, and ICI 182,780 on Endometrial Cancer Growth," Journal of the National Cancer Institute, 1998, 90:1552-8.
Osipo, C. et al., "Paradoxical Action of Fulvestrant in Estradiol-Induced Regression of Tamoxifen-Stimulated Breast Cancer," Journal of the National Cancer Institute, 2003, 95:1597-608.
Osipo, C. et al., "Reversal of tamoxifen resistant breast cancer by low dose estrogen therapy," The Journal of Steroid Biochemistry and Molecular Biology, 2005, 93:249-56.
Overk, C.R. et al., "Structure-activity relationships for a family of benzothiophene selective estrogen receptor modulators including raloxifene and arzoxifene," ChemMedChem, 2007, 2:1520-6.
Palkowitz, A.D. et al., "Discovery and synthesis of [6-hydroxy-3-[4-[2-(1-piperidinyl)ethoxy]phenoxy]-2-(4-hydroxyphenyl)]b enzo[b]thiophene: a novel, highly potent, selective estrogen receptor modulator," J Med Chem, 1997, 40:1407-16.
Parcellier, A. et al., "PKB and the mitochondria: AKTing on apoptosis," Cell Signal, 2008, 20, 21.
Peethambaram, P.P. et al., "Randomized trial of diethylstilbestrol vs. tamoxifen in postmenopausal women with metastatic breast cancer. An updated analysis," Breast Cancer Research and Treatment, 1999, 54:117-22.
Pietras, R.J. et al., "Membrane-Associated Estrogen Receptor Signaling Pathways in Human Cancers," Clinical Cancer Research, 2007, 13:4672-6.
Prossnitz, E.R. et al., "The G-protein-coupled estrogen receptor GPER in health and disease," Nat Rev Endocrinol, 2011, 7, 715.
Qin, Z. et al., "Benzothiophene selective estrogen receptor modulators with modulated oxidative activity and receptor affinity," J Med Chem, 2007, 50:2682-92.
Qin, Z. et al., "Design and synthesis of neuroprotective methylthiazoles and modification as NO-chimeras for neurodegenerative therapy," J Med Chem, 2012, 55, 6784.
Qin, Z. et al., "Structural modulation of oxidative metabolism in design of improved benzothiophene selective estrogen receptor modulators," Drug Metab Dispos, 2009, 37:161-9.
Resnick, S.M. et al., "Effects of estrogen replacement therapy on PET cerebral blood flow and neuropsychological performance," Horm Behav, 1998, 34, 171.
Resnick, S.M. et al., "Estrogen replacement therapy and longitudinal decline in visual memory. A possible protective effect?," Neurology, 1997, 49, 1491.
Ridnour, L. et al., "Nitric Oxide-Mediated Regulation of beta-Amyloid Clearance via Alterations of MMP-9/TIMP-1," J Neurochem, 2012, vol. 123, Issue 5, 736-749.
Rocca, W.A. et al., "Oophorectomy, menopause, estrogen, and cognitive aging: the timing hypothesis," Neurodegener Dis, 2010, 7, 163.
Rossouw, J.E. et al., "Risks and benefits of estrogen plus progestin in healthy postmenopausal women: principal results From the Women's Health Initiative randomized controlled trial," JAMA, 2002, 288, 321.
Saita, A. et al., "Randomized, double-blind, placebo-controlled study on effects of raloxifene and hormone replacement therapy on plasma no concentrations, endothelin-1 levels, and endothelium-dependent vasodilation in postmenopausal women," Arterioscler Thromb Vasc Biol, 2001, 21, 1512.
Santen, R.J. et al., "Adaptive Hypersensitivity to Estrogen," Clinical Cancer Research, 2004, 10:337s-45s.

(56) References Cited

OTHER PUBLICATIONS

Sato, M. et al., "LY353381.HC1: a novel raloxifene analog with improved SERM potency and efficacy in vivo," J Pharmacol Exp Ther, 1998, 287, 1.
Schiefer, I.T. et al., "Furoxans (1,2,5-Oxadiazole-N-Oxides) as Novel NO Mimetic Neuroprotective and Procognitive Agents," J Med Chem, 2012, 55, 3076.
Selley, M.L., "Increased (E)-4-hydroxy-2-nonenal and asymmetric dimethylarginine concentrations and decreased nitric oxide concentrations in the plasma of patients with major depression," J Affect Disord, 2004, 80, 249.
Sherwin, B.B., "Estrogen therapy: is time of initiation critical for neuroprotection?," Nat Rev Endocrinol, 2009, 5, 620.
Shim, W-S. et al., "Estradiol Hypersensitivity and Mitogen-Activated Protein Kinase Expression in Long-Term Estrogen Deprived Human Breast Cancer Cells in Vivo," Endocrinology, 2000, 141:396-405.
Shumaker, S.A. et al., "The Women's Health Initiative Memory Study (WHIMS): a trial of the effect of estrogen therapy in preventing and slowing the progression of dementia," Control Clin Trials, 1998, 19, 604.
Simoncini, T. et al., "Nongenomic mechanisms of endothelial nitric oxide synthase activation by the selective estrogen receptor modulator raloxifene," Circulation, 2002, 105, 1368.
Siris, E. et al., "Effects of raloxifene on fracture severity in postmenopausal women with osteoporosis: results from the MORE study. Multiple Outcomes of Raloxifene Evaluation," Osteoporos Int, 2002, 13, 907.
Smith, A.R. et al., "Age-related changes in endothelial nitric oxide synthase phosphorylation and nitric oxide dependent vasodilation: evidence for a novel mechanism involving sphingomyelinase and ceramide-activated phosphatase 2A," Aging Cell, 2006, 5, 391.
Smith, S. et al., "A novel nitrate ester reverses the cognitive impairment caused by scopolamine in the Morris water maze," Neuroreport, 2000, 11, 3883.
Snyder, K.R. et al., "Raloxifene hydrochloride," Am J Health Syst Pharm, 2000, 57:1669-75, quiz 76-8.
Song, R.X-D. et al., "Apoptotic action of estrogen," Apoptosis, 2003, 8:55-60.
Song, R.X-D. et al., "Effect of Long-Term Estrogen Deprivation on Apoptotic Responses of Breast Cancer Cells to 17β-Estradiol," Journal of the National Cancer Institute, 2001, 93:1714-23.
Song, R.X-D. et al., "Linkage of Rapid Estrogen Action to MAPK Activation by ERŒ± -Shc Association and Shc Pathway Activation," Molecular Endocrinology, 2002, 16:116-27.
Sporn, M.B., "Arzoxifene: A promising new selective estrogen receptor modulator for clinical chemoprevention of breast cancer," Clinical Cancer Research, 2004, vol. 10, No. 16, pp. 5313-5315.
Steenland, K. et al., "Recent trends in Alzheimer disease mortality in the United States, 1999 to 2004," Alzheimer Dis Assoc Disord, 2009, 23, 165.
Sterniczuk, R. et al., "Characterization of the 3xTg-AD mouse model of Alzheimer's disease: part 2. Behavioral and cognitive changes," Brain Res, 2010, 1348, 149.
Stirone, C. et al., "Estrogen receptor activation of phosphoinositide-3 kinase, akt, and nitric oxide signaling in cerebral blood vessels: rapid and long-term effects," Mol Pharmacol, 2005, 67, 105.
Suh, N. et al., "Arzoxifene, a new selective estrogen receptor modulator for chemoprevention of experimental breast cancer," Cancer Res, 2001, 61:8412-5.
Taddei, S. et al., "Menopause is associated with endothelial dysfunction in women," Hypertension, 1996, 28, 576.
Tanapat, P. et al., "Estrogen Stimulates a Transient Increase in the Number of New Neurons in the Dentate Gyrus of the Adult Female Rat," J. Neurosci, 1999, 19, 5792.
Thatcher, G.R. et al., "Nitric oxide mimetic molecules as therapeutic agents in Alzheimer's disease," Curr Alzheimer Res, 2005, 2, 171.
Thatcher, G.R. et al., "NO chimeras as therapeutic agents in Alzheimer's disease," Curr Alzheimer Res, 2006, 3, 237.

Tonetti, D.A. et al., "Elevated protein kinase C alpha expression may be predictive of tamoxifen treatment failure," Br J Cancer, 2003, 88:1400-2.
Tonetti, D.A. et al., "Stable transfection of protein kinase C alpha cDNA in hormone-dependent breast cancer cell lines," Br J Cancer, 2000, 83:782-91.
Tran, C. et al., "Development of a Second-Generation Antiandrogen for Treatment of Advanced Prostate Cancer," Science, 2009, 324:787-90.
Turner, R.T. et al., "Skeletal effects of estrogen," Endocr Rev, 1994, 15, 275.
Vogel, V.G. et al., "Effects of tamoxifen vs raloxifene on the risk of developing invasive breast cancer and other disease outcomes: the NSABP Study of Tamoxifen and Raloxifene (STAR) P-2 trial," JAMA, 2006, 295, 2727.
Wegesin, D.J. et al., "Effects of hormone replacement therapy and aging on cognition: evidence for executive dysfunction," Neuropsychol Dev Cogn B Aging Neuropsychol Cogn, 2007, 14, 301.
White, B.P. et al., "Raloxifene and estradiol-induced tumor regression in tamoxifen-resistant T47D:A18/PKCα is accompanied by ERα translocation to extranuclear sites (submitted)," Molecular Cancer Research, 2012.
Wu, T.W. et al., "17Beta-estradiol induced Ca2+ influx via L-type calcium channels activates the Src/ERK/cyclic-AMP response element binding protein signal pathway and BCL-2 expression in rat hippocampal neurons: a potential initiation mechanism for estrogen-induced neuroprotection," Neuroscience, 2005, 135, 59.
Wu, X. et al., "Raloxifene and estradiol benzoate both fully restore hippocampal choline acetyltransferase activity in ovariectomized rats," Brain Research, 1999, 847, 98.
Wyckoff, M.H. et al., "Plasma membrane estrogen receptors are coupled to endothelial nitric-oxide synthase through Galpha(i)," J Biol Chem, 2001, 276, 27071.
Yaffe, K. et al., "Cognitive function in postmenopausal women treated with raloxifene," N Engl J Med, 2001, 344, 1207.
Yaffe, K. et al., "Effect of Raloxifene on Prevention of Dementia and Cognitive Impairment in Older Women: The Multiple Outcomes of Raloxifene Evaluation (MORE) Randomized Trial," Am J Psychiatry, 2005, 162, 683.
Yaffe, K. et al., "Estrogen therapy in postmenopausal women: effects on cognitive function and dementia," JAMA, 1998, 279, 688.
Yao, K. et al., "Antitumor Action of Physiological Estradiol on Tamoxifen-stimulated Breast Tumors Grown in Athymic Mice," Clinical Cancer Research, 2000, 6:2028-36.
Yu, B. et al., "Structural modulation of reactivity/activity in design of improved benzothiophene selective estrogen receptor modulators: induction of chemopreventive mechanisms," Mol Cancer Ther, 2007, 6:2418-28.
Zhang, Q.G. et al., "C terminus of Hsc70-interacting protein (CHIP)-mediated degradation of hippocampal estrogen receptor-alpha and the critical period hypothesis of estrogen neuroprotection," Proc Natl Acad Sci U S A, 2011, 108, E617.
Zhang, Y. et al., "Estradiol-Induced Regression in T47D:A18/PKCα Tumors Requires the Estrogen Receptor and Interaction with the Extracellular Matrix," Molecular Cancer Research, 2009, 7:498-510.
Zhou, J. et al., "Effects of estrogen treatment on expression of brain-derived neurotrophic factor and cAMP response element-binding protein expression and phosphorylation in rat amygdaloid and hippocampal structures," Neuroendocrinology, 2005, 81, 294.
Pitt et al., "Heteroaromatic Rings of the Future" J. Med. Chem. 2009, 52, 2952-2963.
Pozharskii et al., Heterocycles in Life and Society, Wiley, 1997, pp. 1-6.
Toader, V. et al.: "Nitrosation, nitration, and autoxidation of the selective estrogen receptor modulator raloxifene by nitric oxide, peroxynitrite, and reactive nitrogen/oxygen species", Chemical Research in Toxicology, vol. 16, No. 10, Jun. 9, 2003, pp. 1264-1276.
International Search Report and Written Opinion for Application No. PCT/US2013/066699 dated Jan. 28, 2014 (13 pages).
International Search Report and Written Opinion for Application No. PCT/US2013/066702 dated Feb. 10, 2014 (12 pages).

(56) References Cited

OTHER PUBLICATIONS

European Search Report for Application No. 13848425.8 dated Jun. 15, 2016 (8 pages).
European Search Report for Application No. 13849663.3 dated Aug. 17, 2016 (7 pages).
United States Patent Office Action for U.S. Appl. No. 14/438,361 dated Jun. 28, 2016 (18 pages).
United States Patent Office Notice of Allowance for U.S. Appl. No. 14/438,326 dated Jun. 10, 2016 (7 pages).
Extended European Search Report for Application No. 13848425.8 dated Sep. 19, 2016 (13 pages).
United States Patent Office Action for U.S. Appl. No. 15/264,407 dated Feb. 24, 2017 (17 pages).
United States Patent Office Notice of Allowance for U.S. Appl. No. 15/264,407 dated Oct. 5, 2017 (7 pages).

* cited by examiner

COMPOSITIONS AND METHODS FOR TREATING ESTROGEN-RELATED MEDICAL DISORDERS

CROSS-REFERENCE TO RELATED APPLICATIONS

This is a continuation of U.S. patent application Ser. No. 14/438,361, filed on Apr. 24, 2015, which is a U.S. national stage entry of International Patent Application No. PCT/US2013/066702, filed on Oct. 24, 2013, which claims priority to U.S. Provisional Patent Application No. 61/809,101, filed on Apr. 5, 2013, and U.S. Provisional Patent Application No. 61/718,035, filed on Oct. 24, 2012, the entire contents of all of which are fully incorporated herein by reference.

STATEMENT OF GOVERNMENT INTEREST

This invention was made with government support under contract number NIH RO1 CA102590 awarded by the National Institutes of Health. The government has certain rights in the invention.

TECHNICAL FIELD

The present invention relates to compounds, compositions, and methods for treating and identifying estrogen-related medical disorders such as cancer, inflammation, osteoporosis, vaginal atrophy, central nervous diseases, and cardiovascular system diseases.

BACKGROUND

In addition to developmental functions, estrogens have been found to reduce incidence of coronary heart disease (1), maintain bone mineral density (2), and in the CNS, promote neuronal survival (3, 4) and hippocampal neurogenesis (5-7). Neuro-imaging studies reveal that estrogen therapy improves cerebral blood flow and performance in hippocampal-dependent memory tasks in humans (8, 9). Other observational studies have found that estrogen helps alleviate age-related cognitive decline by preserving executive function in the frontal lobe (10).

Raloxifene (EVISTA) is a second generation selective estrogen receptor modulator (SERM) used clinically for the treatment of osteoporosis in postmenopausal women, which acts as an antiestrogen in breast and endometrium (17-21). Raloxifene, however, increases the lifetime risk of thromboembolism (23). Raloxifene has been found to enhance levels of vasodilatory NO through action on endothelial nitric oxide synthase (eNOS) (24-26), and, the increased thromboembolic events have been attributed to decreased eNOS activity in postmenopausal women (27). NO inhibits thrombus formation through inhibition of platelet recruitment, adhesion and aggregation (28). The next generation SERM, arzoxifene (41, 42), a prodrug of desmethylarzoxifene (DMA) was designed to improve the pharmacokinetic (PK) profile relative to raloxifene, from which it differs by only one atom (43, 44).

SUMMARY

In one aspect, disclosed is a compound of formula (I)

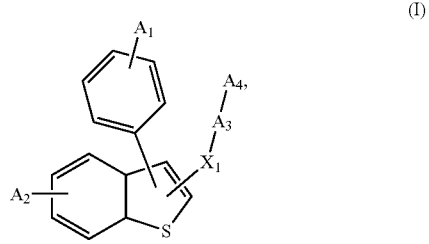

or a pharmaceutically acceptable salt thereof. $A_1$ is selected from the group consisting of halogen, trifluoromethyl, and —$OR_1$. $A_2$ is selected from the group consisting of halogen, trifluoromethyl, and —$OR_2$. $X_1$ is selected from the group consisting of alkyl, —O—, —N(H)—, —S—, —S(=O)—, and —C(=O)—. $A_3$ is selected from the group consisting of alkyl, aryl, cycloalkyl, cycloalkylalkyl, heterocycle, and heteroaryl. $A_4$ is selected from the group consisting of hydrogen, halogen, alkyl, cyano, trifluoromethyl, aryl-heteroaryl wherein the aryl is substituted or unsubstituted (e.g., 1-(4-fluorophenyl)-1H-1,2,3-triazolyl), and —$OR_3$. $R_1$, $R_2$ and $R_3$ are each independently selected from the group consisting of hydrogen, alkyl, —$SO_3R^{x1}$, —$PO_3R^{y1}R^{z1}$, —$C(=O)R^a$, and —$R_4$-$G_1$. $R^{x1}$, $R^{y1}$ and $R^{z1}$, at each occurrence, are independently selected from the group consisting of hydrogen and a pharmaceutically acceptable cation. $R^a$ is alkyl or —OH. $R_4$, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. $G_1$, at each occurrence, is independently selected from the group consisting of hydrogen and —$ONO_2$, wherein at least one of $R_1$, $R_2$ and $R_3$ is —$R_4$-$G_1$, and wherein at least one occurrence of $G_1$ is —$ONO_2$.

Also provided herein is a compound of formula (I), wherein $R_4$, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

Also provided herein is a compound of formula (I), wherein $R_4$, at each occurrence, is independently selected from the group consisting of alkyl, alkylheterocyclealkyl, and heterocyclealkyl.

Also provided herein is a compound of formula (I), wherein $A_4$ is selected from the group consisting of halogen and —$OR_3$.

The compound of formula (I) may comprise a compound of formula (I-i), a compound of formula (I-ii), a compound of formula (I-iii), a compound of formula (I-iv), a compound of formula (I-v), or a compound of formula (I-vi)

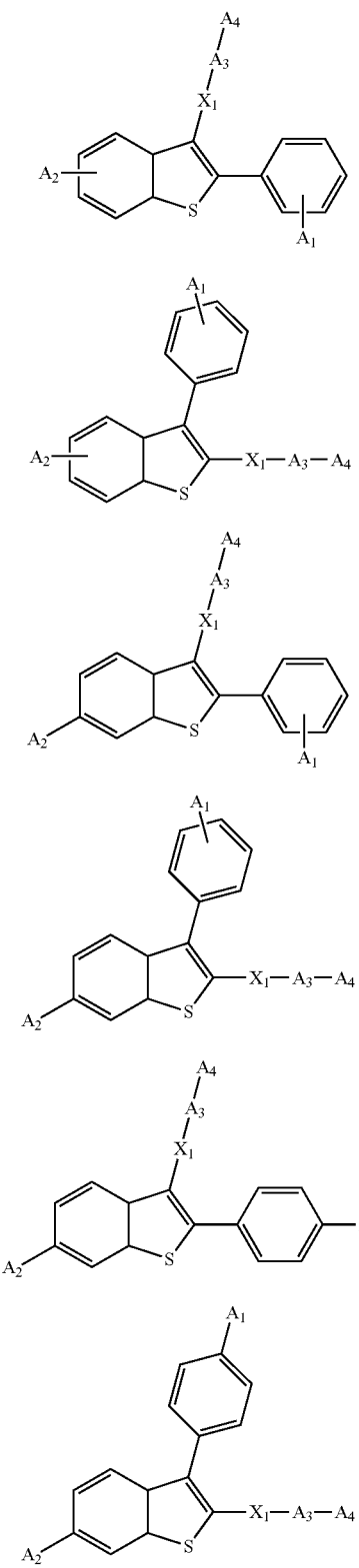

or a pharmaceutically acceptable salt thereof. $A_1$ is selected from the group consisting of halogen, trifluoromethyl, and —$OR_1$. $A_2$ is selected from the group consisting of halogen, trifluoromethyl, and —$OR_2$. $X_1$ is selected from the group consisting of alkyl, —O—, —N(H)—, —S—, —S(=O)—, and —C(=O)—. $A_3$ is selected from the group consisting of alkyl, aryl, cycloalkyl, cycloalkylalkyl, heterocycle, and heteroaryl. $A_4$ is selected from the group consisting of hydrogen, halogen, alkyl, cyano, trifluoromethyl, aryl-heteroaryl wherein the aryl is substituted or unsubstituted (e.g., 1-(4-fluorophenyl)-1H-1,2,3-triazolyl), and —$OR_3$. $R_1$, $R_2$ and $R_3$ are each independently selected from the group consisting of hydrogen, alkyl, —$SO_3R^{x1}$, —$PO_3R^{y1}R^{z1}$, —C(=O)$R^a$, and —$R_4$-$G_1$. $R^{x1}$, $R^{y1}$ and $R^{z1}$, at each occurrence, are independently selected from the group consisting of hydrogen and a pharmaceutically acceptable cation. $R^a$ is alkyl or —OH. $R_4$, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. $G_1$, at each occurrence, is independently selected from the group consisting of hydrogen and —$ONO_2$, wherein at least one of $R_1$, $R_2$ and $R_3$ is —$R_4$-$G_1$, and wherein at least one occurrence of $G_1$ is —$ONO_2$.

Also provided herein is a compound of formula (I-i), a compound of formula (I-ii), a compound of formula (I-iii), a compound of formula (I-iv), a compound of formula (I-v), or a compound of formula (I-vi), wherein $R_4$, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

Also provided herein is a compound of formula (I-i), a compound of formula (I-ii), a compound of formula (I-iii), a compound of formula (I-iv), a compound of formula (I-v), or a compound of formula (I-vi), wherein $R_4$, at each occurrence, is independently selected from the group consisting of alkyl, alkylheterocyclealkyl, and heterocyclealkyl.

The compound of formula (I) may comprise a compound of formula (Ia)

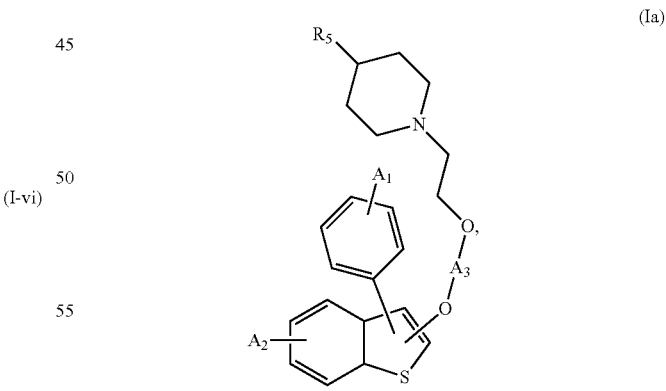

or a pharmaceutically acceptable salt thereof. $A_1$ is selected from the group consisting of halogen, trifluoromethyl, and —$OR_1$. $A_2$ is selected from the group consisting of halogen, trifluoromethyl, and —$OR_2$. $A_3$ is selected from the group consisting of alkyl, aryl, cycloalkyl, cycloalkylalkyl, heterocycle, and heteroaryl. $R_1$ and $R_2$ are each independently selected from the group consisting of hydrogen, alkyl, —$SO_3R^{x1}$, —$PO_3R^{y1}R^{z1}$, —C(=O)$R^a$, and —$R_4$-$G_1$. $R_4$, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. $R_5$ is selected from the group consisting of hydrogen and $C_1$-$C_3$-alkyl-$G_1$. $G_1$, at each occurrence, is independently selected from the group consisting of hydrogen and —$ONO_2$, wherein at least one of $R_1$ and $R_2$ is —$R_4$-$G_1$ and/or $R_5$ is $C_1$-$C_3$-alkyl-$G_1$, and wherein at least one occurrence of $G_1$ is —$ONO_2$. $R^{x1}$, $R^{y1}$ and $R^{z1}$ are each independently selected from the group consisting of hydrogen and a pharmaceutically acceptable cation. $R^a$ is alkyl or —OH.

The compound of formula (I) may comprise a compound of formula (Ia), wherein $R_4$, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

The compound of formula (I) may comprise a compound of formula (Ia), wherein $R_4$, at each occurrence, is independently selected from the group consisting of alkyl, alkylheterocyclealkyl, and heterocyclealkyl.

The compound of formula (I) may comprise a compound of formula (Ia), wherein —$R_4$-$G_1$ is

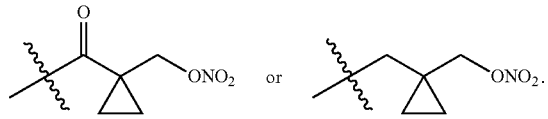

The compound of formula (I) may comprise a compound of formula (Ia-i), a compound of formula (Ia-ii), a compound of formula (Ia-iii), a compound of formula (Ia-iv), a compound of formula (Ia-v), or a compound of formula (Ia-vi)

(Ia-i)

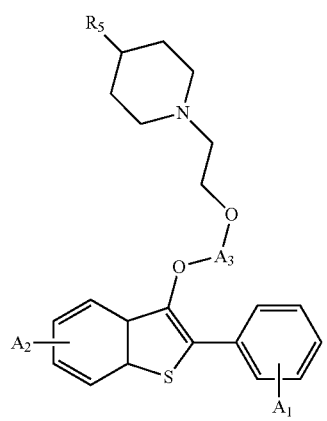

(Ia-ii)

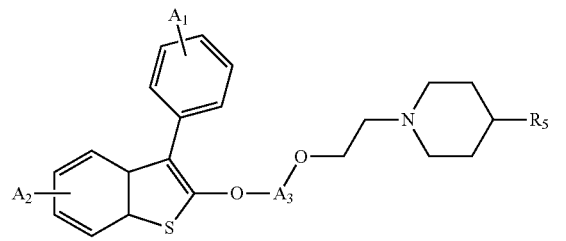

(Ia-iii)

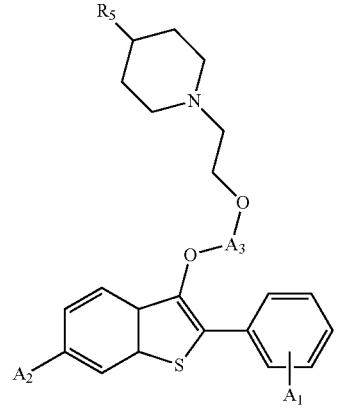

(Ia-iv)

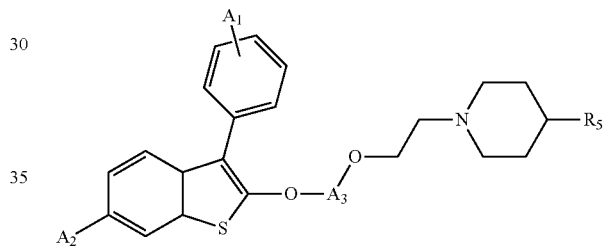

(Ia-v)

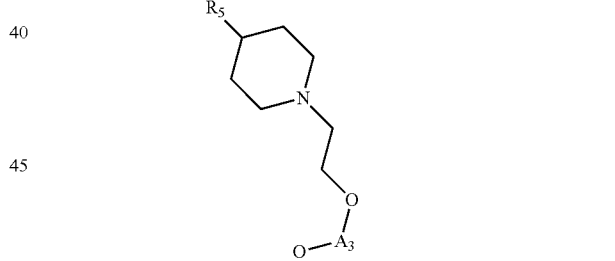

(Ia-vi)

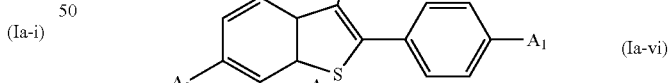

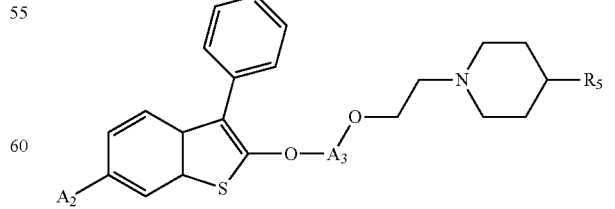

or a pharmaceutically acceptable salt thereof. $A_1$ is selected from the group consisting of halogen, trifluoromethyl, and —$OR_1$. $A_2$ is selected from the group consisting of halogen, trifluoromethyl, and —OR₂. A₃ is selected from the group consisting of alkyl, aryl, cycloalkyl, cycloalkylalkyl, heterocycle, and heteroaryl. $R_1$ and $R_2$ are each independently selected from the group consisting of hydrogen, alkyl, —SO₃$R^{x1}$, —PO₃$R^{y1}R^{z1}$, —C(=O)$R^a$, and —R₄-G₁. R₄, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. $R_5$ is selected from the group consisting of hydrogen and $C_1$-$C_3$-alkyl-G₁. G₁, at each occurrence, is independently selected from the group consisting of hydrogen and —ONO₂, wherein at least one of $R_1$ and $R_2$ is —R₄-G₁ and/or $R_5$ is $C_1$-$C_3$-alkyl-G₁, and wherein at least one occurrence of G₁ is —ONO₂. $R^{x1}$, $R^{y1}$ and $R^{z1}$ are each independently selected from the group consisting of hydrogen and a pharmaceutically acceptable cation. $R^a$ is alkyl.

The compound of formula (I) may comprise a compound of formula (Ia-i), a compound of formula (Ia-ii), a compound of formula (Ia-iii), a compound of formula (Ia-iv), a compound of formula (Ia-v), or a compound of formula (Ia-vi), wherein R₄, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

The compound of formula (I) may comprise a compound of formula (Ia-i), a compound of formula (Ia-ii), a compound of formula (Ia-iii), a compound of formula (Ia-iv), a compound of formula (Ia-v), or a compound of formula (Ia-vi), wherein R₄, at each occurrence, is independently selected from the group consisting of alkyl, alkylheterocyclealkyl, and heterocyclealkyl.

The compound of formula (I) may comprise a compound of formula (Ia-i), a compound of formula (Ia-ii), a compound of formula (Ia-iii), a compound of formula (Ia-iv), a compound of formula (Ia-v), or a compound of formula (Ia-vi), wherein —R₄-G₁ is

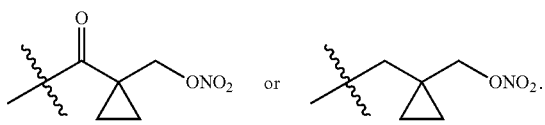

The compound of formula (I) may comprise formula (Ib)

or a pharmaceutically acceptable salt thereof. $A_1$ is selected from the group consisting of halogen, trifluoromethyl, and —OR₁. $A_2$ is selected from the group consisting of halogen, trifluoromethyl, and —OR₂. $R_1$ and $R_2$ are each independently selected from the group consisting of hydrogen, alkyl, —SO₃$R^{x1}$, —PO₃$R^{y1}R^{z1}$, —C(=O)$R^a$, and —R⁴-G₁. R₄, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. $R_5$ is selected from the group consisting of hydrogen and $C_1$-$C_3$-alkyl-G₁. G₁, at each occurrence, is independently selected from the group consisting of hydrogen and —ONO₂, wherein at least one of $R_1$ and $R_2$ is —R₄-G₁ and/or $R_5$ is $C_1$-$C_3$-alkyl-G₁, and wherein at least one occurrence of G₁ is —ONO₂. $R^{x1}$, $R^{y1}$ and $R^{z1}$ are each independently selected from the group consisting of hydrogen and a pharmaceutically acceptable cation. $R^a$ is alkyl or —OH.

The compound of formula (I) may comprise a compound of formula (Ib), wherein R₄, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

The compound of formula (I) may comprise a compound of formula (Ib), wherein R₄, at each occurrence, is independently selected from the group consisting of alkyl, alkylheterocyclealkyl, and heterocyclealkyl.

The compound of formula (I) may comprise a compound of formula (Ib), wherein R₄-G₁ is

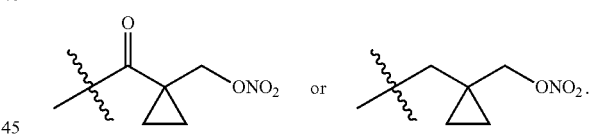

The compound of formula (I) may comprise a compound of formula (Ib-i), a compound of formula (Ib-ii), a compound of formula (Ib-iii), a compound of formula (Ib-iv), a compound of formula (Ib-v), or a compound of formula (Ib-vi)

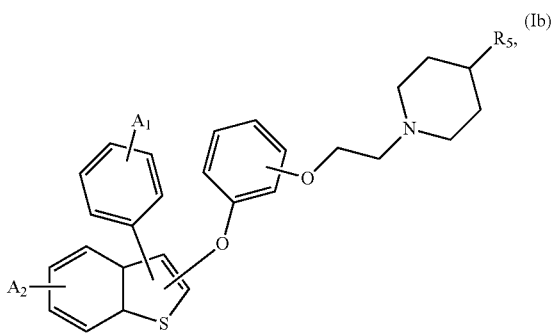

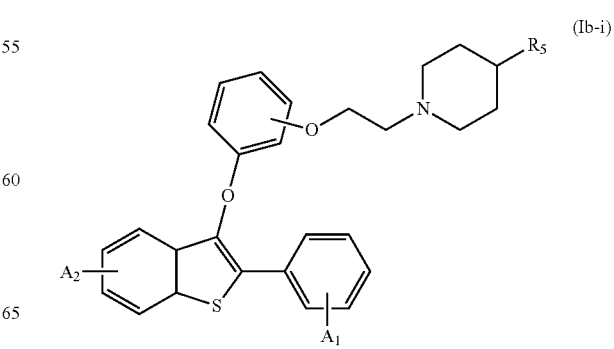

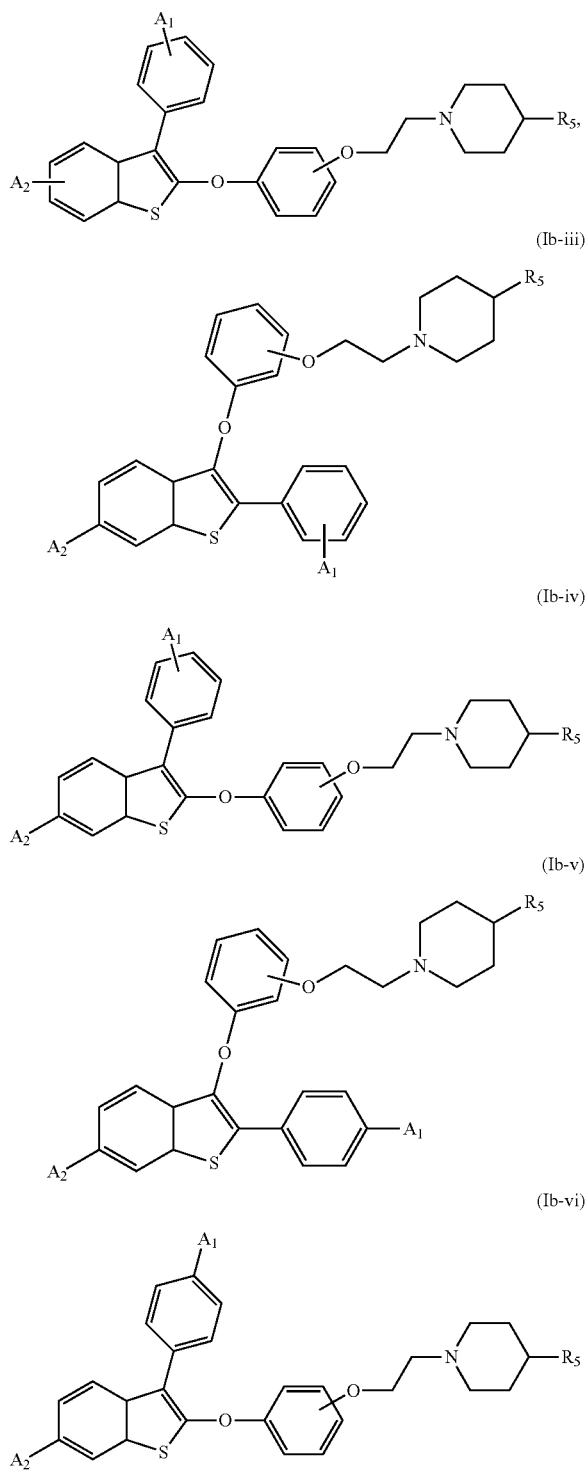

a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. $R_5$ is selected from the group consisting of hydrogen and $C_1$-$C_3$-alkyl-$G_1$. $G_1$, at each occurrence, is independently selected from the group consisting of hydrogen and —$ONO_2$, wherein at least one of $R_1$ and $R_2$ is —$R_4$-$G_1$ and/or $R_5$ is $C_1$-$C_3$-alkyl-$G_1$, and wherein at least one occurrence of $G_1$ is —$ONO_2$. $R^{x1}$, $R^{y1}$ and $R^{z1}$ are each independently selected from the group consisting of hydrogen and a pharmaceutically acceptable cation. $R^a$ is alkyl or —OH.

The compound of formula (I) may comprise a compound of formula (Ib-i), a compound of formula (Ib-ii), a compound of formula (Ib-iii), a compound of formula (Ib-iv), a compound of formula (Ib-v), or a compound of formula (Ib-vi), wherein $R_4$, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

The compound of formula (I) may a compound of formula (Ib-i), a compound of formula (Ib-ii), a compound of formula (Ib-iii), a compound of formula (Ib-iv), a compound of formula (Ib-v), or a compound of formula (Ib-vi), wherein $R_4$, at each occurrence, is independently selected from the group consisting of alkyl, alkylheterocyclealkyl, and heterocyclealkyl.

The compound of formula (I) may comprise a compound of formula (Ib-i), a compound of formula (Ib-ii), a compound of formula (Ib-iii), a compound of formula (Ib-iv), a compound of formula (Ib-v), or a compound of formula (Ib-vi), wherein $R_4$-$G_1$ is

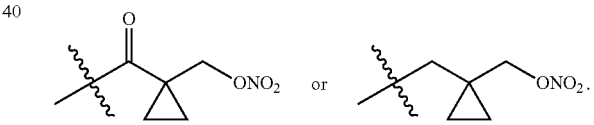

The compound of formula (I) may comprise formula (Ic)

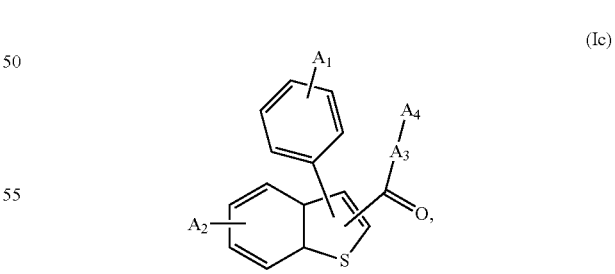

or a pharmaceutically acceptable salt thereof. $A_1$ is selected from the group consisting of halogen, trifluoromethyl, and —$OR_1$. $A_2$ is selected from the group consisting of halogen, trifluoromethyl, and —$OR_2$. $R_1$ and $R_2$ are each independently selected from the group consisting of hydrogen, alkyl, —$SO_3R^{x1}$, —$PO_3R^{y1}R^{z1}$, —C(=O)$R^a$, and —$R^4$-$G_1$. $R_4$, at each occurrence, is independently selected from the group consisting of a substituent comprising 1 to 10 carbon atoms, or a pharmaceutically acceptable salt thereof. $A_1$ is selected from the group consisting of halogen, trifluoromethyl, and —$OR_1$. $A_2$ is selected from the group consisting of halogen, trifluoromethyl, and —$OR_2$. $A_3$ is selected from the group consisting of alkyl, aryl, cycloalkyl, cycloalkylalkyl, heterocycle, and heteroaryl. $A_4$ is selected from the group consisting of hydrogen, halogen, alkyl, cyano, trifluoromethyl, aryl-heteroaryl wherein the aryl is substituted or unsubstituted (e.g., 1-(4-fluorophenyl)-1H-1,2,3-triazolyl), and —OR₃. R₁, R₂ and R₃ are each independently selected from the group consisting of hydrogen, alkyl, —SO₃R$^{x1}$, —PO₃R$^{y1}$R$^{z1}$, —C(=O)R$^a$, and —R₄-G₁. R$^{x1}$, R$^{y1}$ and R$^{z1}$, at each occurrence, are independently selected from the group consisting of hydrogen and a pharmaceutically acceptable cation. R$^a$ is alkyl or —OH. R₄, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. G₁, at each occurrence, is independently selected from the group consisting of hydrogen and —ONO₂, wherein at least one of R₁, R₂ and R₃ is —R₄-G₁, and wherein at least one occurrence of G₁ is —ONO₂.

The compound of formula (I) may comprise a compound of formula (Ic), wherein R₄, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

The compound of formula (I) may comprise a compound of formula (Ic), wherein R₄, at each occurrence, is independently selected from the group consisting of alkyl, alkylheterocyclealkyl, and heterocyclealkyl.

The compound of formula (I) may comprise a compound of formula (Ic), wherein R₄-G₁ is

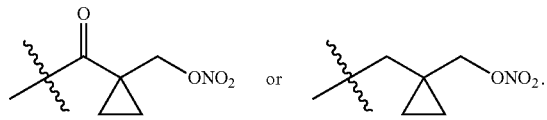

The compound of formula (I) may comprise a compound of formula (Ic-i), a compound of formula (Ic-ii), a compound of formula (Ic-iii), a compound of formula (Ic-iv), a compound of formula (Ic-v), or a compound of formula (Ic-vi)

(Ic-i)
(Ic-ii)

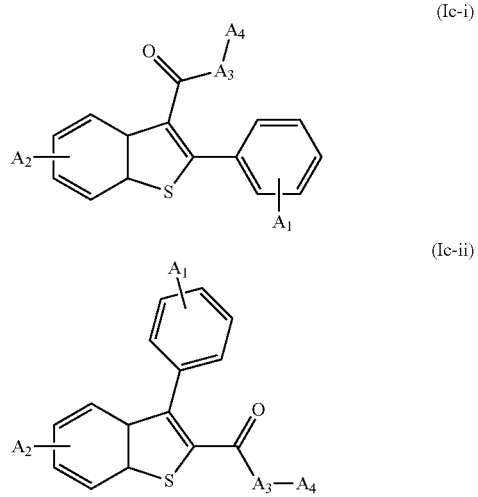

(Ic-iii)
(Ic-iv)
(Ic-v)
(Ic-vi)

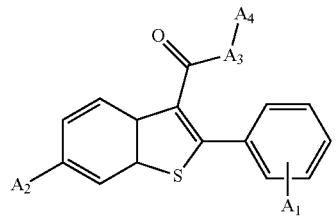
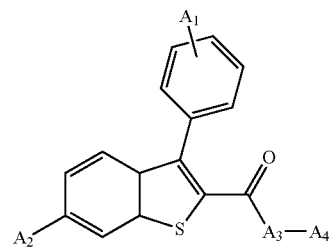
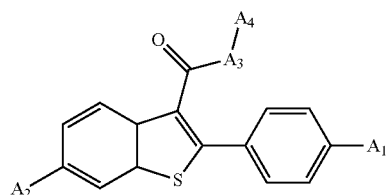
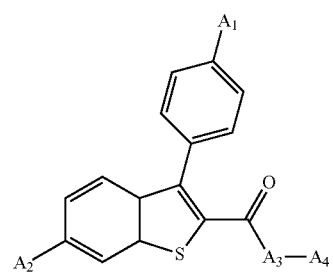

or a pharmaceutically acceptable salt thereof. A₁ is selected from the group consisting of halogen, trifluoromethyl, and —OR₁. A₂ is selected from the group consisting of halogen, trifluoromethyl, and —OR₂. A₃ is selected from the group consisting of alkyl, aryl, cycloalkyl, cycloalkylalkyl, heterocycle, and heteroaryl. A₄ is selected from the group consisting of hydrogen, halogen, alkyl, cyano, trifluoromethyl, aryl-heteroaryl wherein the aryl is substituted or unsubstituted (e.g., 1-(4-fluorophenyl)-1H-1,2,3-triazolyl), and —OR₃. R₁, R₂ and R₃ are each independently selected from the group consisting of hydrogen, alkyl, —SO₃R$^{x1}$, —PO₃R$^{y1}$R$^{z1}$, —C(=O)R$^a$, and —R₄-G₁. R$^{x1}$, R$^{y1}$ and R$^{z1}$, at each occurrence, are independently selected from the group consisting of hydrogen and a pharmaceutically acceptable cation. R$^a$ is alkyl or —OH. R₄, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. G₁, at each occurrence, is independently selected from the group consisting of hydrogen and —ONO₂, wherein at least one of R₁, R₂ and R₃ is —R₄-G₁, and wherein at least one occurrence of G₁ is —ONO₂.

The compound of formula (I) may comprise a compound of formula (Ic-i), a compound of formula (Ic-ii), a compound of formula (Ic-iii), a compound of formula (Ic-iv), a compound of formula (Ic-v), or a compound of formula (Ic-vi), wherein R₄, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

The compound of formula (I) may comprise a compound of formula (Ic-i), a compound of formula (Ic-ii), a compound of formula (Ic-iii), a compound of formula (Ic-iv), a compound of formula (Ic-v), or a compound of formula (Ic-vi), wherein R₄, at each occurrence, is independently selected from the group consisting of alkyl, alkylheterocyclealkyl, and heterocyclealkyl.

The compound of formula (I) may comprise a compound of formula (Ic-i), a compound of formula (Ic-ii), a compound of formula (Ic-iii), a compound of formula (Ic-iv), a compound of formula (Ic-v), or a compound of formula (Ic-vi), wherein R₄-G₁ is

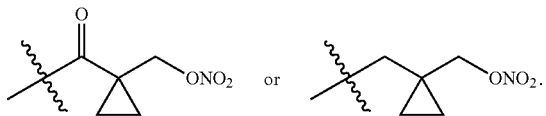

The compound of formula (I) may be selected from the group consisting of:
3-(1-(2-(4-((6-hydroxy-2-(4-hydroxyphenyl)benzo[b]thiophen-3-yl)oxy)phenoxy)ethyl)piperidin-4-yl)propyl nitrate;
4-(6-hydroxy-3-(4-(2-(piperidin-1-yl)ethoxy)phenoxy)benzo[b]thiophen-2-yl)phenyl 1-((nitrooxy)methyl)cyclopropanecarboxylate;
2-(4-fluorophenyl)-3-(4-(2-(piperidin-1-yl)ethoxy)phenoxy)benzo[b]thiophen-6-yl 1-((nitrooxy)methyl)cyclopropanecarboxylate;
3-(1-(2-(4-((6-hydroxy-3-(4-hydroxyphenyl)benzo[b]thiophen-2-yl)oxy)phenoxy)ethyl)piperidin-4-yl)propyl nitrate;
4-(6-hydroxy-2-(4-(2-(piperidin-1-yl)ethoxy)phenoxy)benzo[b]thiophen-3-yl)phenyl 1-((nitrooxy)methyl)cyclopropanecarboxylate;
3-(4-fluorophenyl)-2-(4-(2-(piperidin-1-yl)ethoxy)phenoxy)benzo[b]thiophen-6-yl 1-((nitrooxy)methyl)cyclopropanecarboxylate;
2-(4-fluorophenyl)-3-(4-(trifluoromethyl)benzoyl)benzo[b]thiophen-6-yl 1-((nitrooxy)methyl)cyclopropanecarboxylate;
(1-(((2-(4-fluorophenyl)-3-(4-(trifluoromethyl)benzoyl)benzo[b]thiophen-6-yl)oxy)methyl)cyclopropyl)methyl nitrate;
3-(4-fluorophenyl)-2-(4-(trifluoromethyl)benzoyl)benzo[b]thiophen-6-yl 1-((nitrooxy)methyl)cyclopropanecarboxylate;
(1-(((3-(4-fluorophenyl)-2-(4-(trifluoromethyl)benzoyl)benzo[b]thiophen-6-yl)oxy)methyl)cyclopropyl)methyl nitrate;
3-(cyclopropanecarbonyl)-2-(4-fluorophenyl)benzo[b]thiophen-6-yl 1-((nitrooxy)methyl)cyclopropanecarboxylate;
(1-(((3-(cyclopropanecarbonyl)-2-(4-fluorophenyl)benzo[b]thiophen-6-yl)oxy)methyl)cyclopropyl)methyl nitrate;
2-(cyclopropanecarbonyl)-3-(4-fluorophenyl)benzo[b]thiophen-6-yl 1-((nitrooxy)methyl)cyclopropanecarboxylate;
(1-(((2-(cyclopropanecarbonyl)-3-(4-fluorophenyl)benzo[b]thiophen-6-yl)oxy)methyl)cyclopropyl)methyl nitrate;
2-(4-fluorophenyl)-3-isonicotinoylbenzo[b]thiophen-6-yl 1-((nitrooxy)methyl)cyclopropanecarboxylate;
(1-(((2-(4-fluorophenyl)-3-isonicotinoylbenzo[b]thiophen-6-yl)oxy)methyl)cyclopropyl)methyl nitrate;
3-(4-fluorophenyl)-2-isonicotinoylbenzo[b]thiophen-6-yl 1-((nitrooxy)methyl)cyclopropanecarboxylate;
(1-(((3-(4-fluorophenyl)-2-isonicotinoylbenzo[b]thiophen-6-yl)oxy)methyl)cyclopropyl)methyl nitrate;
2-(4-fluorophenyl)-3-isobutyrylbenzo[b]thiophen-6-yl 1-((nitrooxy)methyl)cyclopropanecarboxylate;
(1-(((2-(4-fluorophenyl)-3-isobutyrylbenzo[b]thiophen-6-yl)oxy)methyl)cyclopropyl)methyl nitrate;
3-(4-fluorophenyl)-2-isobutyrylbenzo[b]thiophen-6-yl 1-((nitrooxy)methyl)cyclopropanecarboxylate;
(1-(((3-(4-fluorophenyl)-2-isobutyrylbenzo[b]thiophen-6-yl)oxy)methyl)cyclopropyl)methyl nitrate;
3-(4-ethynylbenzoyl)-2-(4-fluorophenyl)benzo[b]thiophen-6-yl 1-((nitrooxy)methyl)cyclopropanecarboxylate;
(1-(((3-(4-ethynylbenzoyl)-2-(4-fluorophenyl)benzo[b]thiophen-6-yl)oxy)methyl)cyclopropyl)methyl nitrate;
2-(4-ethynylbenzoyl)-3-(4-fluorophenyl)benzo[b]thiophen-6-yl 1-((nitrooxy)methyl)cyclopropanecarboxylate;
(1-(((2-(4-ethynylbenzoyl)-3-(4-fluorophenyl)benzo[b]thiophen-6-yl)oxy)methyl)cyclopropyl)methyl nitrate;
2-(4-fluorophenyl)-3-(4-methylbenzoyl)benzo[b]thiophen-6-yl 1-((nitrooxy)methyl)cyclopropanecarboxylate;
(1-(((2-(4-fluorophenyl)-3-(4-methylbenzoyl)benzo[b]thiophen-6-yl)oxy)methyl)cyclopropyl)methyl nitrate;
3-(4-fluorophenyl)-2-(4-methylbenzoyl)benzo[b]thiophen-6-yl 1-((nitrooxy)methyl)cyclopropanecarboxylate;
(1-(((3-(4-fluorophenyl)-2-(4-methylbenzoyl)benzo[b]thiophen-6-yl)oxy)methyl)cyclopropyl)methyl nitrate;
2-(4-fluorophenyl)-3-(4-(1-(4-fluorophenyl)-1H-1,2,3-triazol-4-yl)benzoyl)benzo[b]thiophen-6-yl 1-((nitrooxy)methyl)cyclopropanecarboxylate;
(1-(((2-(4-fluorophenyl)-3-(4-(1-(4-fluorophenyl)-1H-1,2,3-triazol-4-yl)benzoyl)benzo[b]thiophen-6-yl)oxy)methyl)cyclopropyl)methyl nitrate;
3-(4-fluorophenyl)-2-(4-(1-(4-fluorophenyl)-1H-1,2,3-triazol-4-yl)benzoyl)benzo[b]thiophen-6-yl 1-((nitrooxy)methyl)cyclopropanecarboxylate;
(1-(((3-(4-fluorophenyl)-2-(4-(1-(4-fluorophenyl)-1H-1,2,3-triazol-4-yl)benzoyl)benzo[b]thiophen-6-yl)oxy)methyl)cyclopropyl)methyl nitrate;
3-((3r,5r,7r)-adamantane-1-carbonyl)-2-(4-fluorophenyl)benzo[b]thiophen-6-yl 1-((nitrooxy)methyl)cyclopropanecarboxylate;
(1-(((3-((3r,5r,7r)-adamantane-1-carbonyl)-2-(4-fluorophenyl)benzo[b]thiophen-6-yl)oxy)methyl)cyclopropyl)methyl nitrate;
2-((3r,5r,7r)-adamantane-1-carbonyl)-3-(4-fluorophenyl)benzo[b]thiophen-6-yl 1-((nitrooxy)methyl)cyclopropanecarboxylate; and
(1-(((2-((3r,5r,7r)-adamantane-1-carbonyl)-3-(4-fluorophenyl)benzo[b]thiophen-6-yl)oxy)methyl)cyclopropyl)methyl nitrate;
or a pharmaceutically acceptable salt thereof.

In another aspect, disclosed is a compound of formula (II),

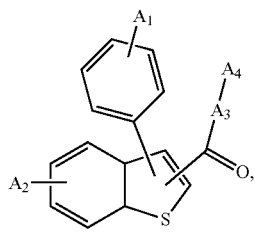

(II)

or a pharmaceutically acceptable salt thereof. $A_1$ is selected from the group consisting of halogen, trifluoromethyl, and —$OR_1$. $A_2$ is selected from the group consisting of halogen, trifluoromethyl, and —$OR_2$. $A_3$ is selected from the group consisting of alkyl, aryl, cycloalkyl, cycloalkylalkyl, heterocycle, and heteroaryl. $A_4$ is selected from the group consisting of hydrogen, halogen, alkyl, cyano, trifluoromethyl, aryl-heteroaryl wherein the aryl is substituted or unsubstituted (e.g., 1-(4-fluorophenyl)-1H-1,2,3-triazolyl), and —$OR_3$. $R_1$, $R_2$ and $R_3$ are each independently selected from the group consisting of hydrogen, alkyl, —$SO_3R^{x1}$, —$PO_3R^{y1}R^{z1}$ and —$C(=O)R^a$. $R^{x1}$, $R^{y1}$ and $R^{z1}$, at each occurrence, are independently selected from the group consisting of hydrogen and a pharmaceutically acceptable cation. $R^a$ is alkyl or —OH.

Also provided are compounds of formula (II), wherein $A_1$ is fluoro. $A_1$ may be fluoro located in the 4-position of the phenyl ring to which it is attached. Also provided are compounds of formula (II), wherein $A_2$ is —OH.

The compound of formula (II) may comprise a compound of formula (II-i), a compound of formula (II-ii), a compound of formula (II-iii), a compound of formula (II-iv), a compound of formula (II-v), or a compound of formula (II-vi)

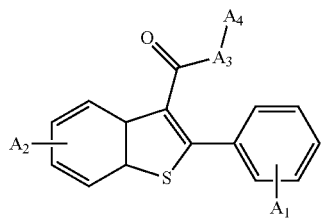

(II-i)

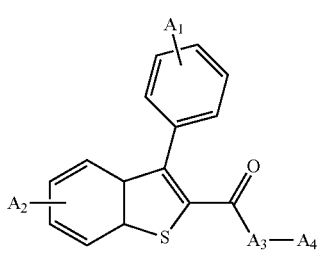

(II-ii)

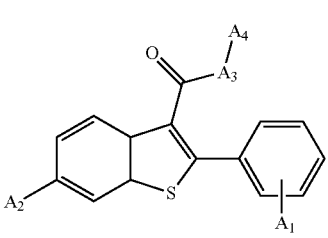

(II-iii)

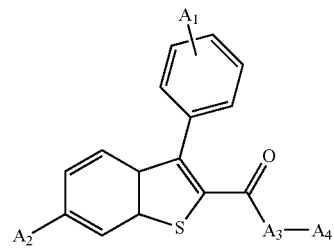

(II-iv)

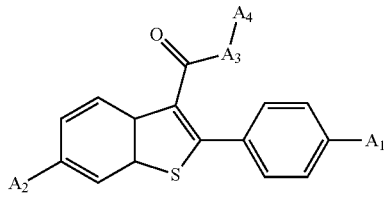

(II-v)

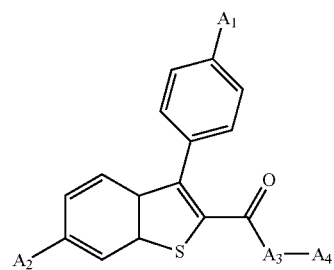

(II-vi)

or a pharmaceutically acceptable salt thereof. $A_1$ is selected from the group consisting of halogen, trifluoromethyl, and —$OR_1$. $A_2$ is selected from the group consisting of halogen, trifluoromethyl, and —$OR_2$. $A_3$ is selected from the group consisting of alkyl, aryl, cycloalkyl, cycloalkylalkyl, heterocycle, and heteroaryl. $A_4$ is selected from the group consisting of hydrogen, halogen, alkyl, cyano, trifluoromethyl, aryl-heteroaryl wherein the aryl is substituted or unsubstituted (e.g., 1-(4-fluorophenyl)-1H-1,2,3-triazolyl), and —$OR_3$. $R_1$, $R_2$ and $R_3$ are each independently selected from the group consisting of hydrogen, alkyl, —$SO_3R^{x1}$, —$PO_3R^{y1}R^{z1}$, and —$C(=O)R^a$. $R^{x1}$, $R^{y1}$ and $R^{z1}$, at each occurrence, are independently selected from the group consisting of hydrogen and a pharmaceutically acceptable cation. $R^a$ is alkyl or —OH.

Also provided herein is a compound of formula (II-i), a compound of formula (II-ii), a compound of formula (II-iii), a compound of formula (II-iv), a compound of formula (II-v), or a compound of formula (II-vi), wherein $A_1$ is fluoro. $A_1$ may be fluoro located in the 4-position of the phenyl ring to which it is attached. Also provided herein is a compound of formula (II-i), a compound of formula (II-ii), a compound of formula (II-iii), a compound of formula (II-iv), a compound of formula (II-v), or a compound of formula (II-vi), wherein $A_2$ is —OH.

The compound of formula (II) may be selected from the group consisting of:
(2-(4-fluorophenyl)-6-hydroxybenzo[b]thiophen-3-yl)(4-(trifluoromethyl)phenyl)methanone;
(3-(4-fluorophenyl)-6-hydroxybenzo[b]thiophen-2-yl)(4-(trifluoromethyl)phenyl)methanone;
cyclopropyl(2-(4-fluorophenyl)-6-hydroxybenzo[b]thiophen-3-yl)methanone;
cyclopropyl(3-(4-fluorophenyl)-6-hydroxybenzo[b]thiophen-2-yl)methanone;

(2-(4-fluorophenyl)-6-hydroxybenzo[b]thiophen-3-yl)(pyridin-4-yl)methanone;
(3-(4-fluorophenyl)-6-hydroxybenzo[b]thiophen-2-yl)(pyridin-4-yl)methanone;
1-(2-(4-fluorophenyl)-6-hydroxybenzo[b]thiophen-3-yl)-2-methylpropan-1-one;
1-(3-(4-fluorophenyl)-6-hydroxybenzo[b]thiophen-2-yl)-2-methylpropan-1-one;
(4-ethynylphenyl)(2-(4-fluorophenyl)-6-hydroxybenzo[b]thiophen-3-yl)methanone;
(4-ethynylphenyl)(3-(4-fluorophenyl)-6-hydroxybenzo[b]thiophen-2-yl)methanone;
(2-(4-fluorophenyl)-6-hydroxybenzo[b]thiophen-3-yl)(p-tolyl)methanone;
(3-(4-fluorophenyl)-6-hydroxybenzo[b]thiophen-2-yl)(p-tolyl)methanone;
(4-(1-(4-fluorophenyl)-1H-1,2,3-triazol-4-yl)phenyl)(2-(4-fluorophenyl)-6-hydroxybenzo[b]thiophen-3-yl)methanone;
(4-(1-(4-fluorophenyl)-1H-1,2,3-triazol-4-yl)phenyl)(3-(4-fluorophenyl)-6-hydroxybenzo[b]thiophen-2-yl)methanone;
(3r,5r,7r)-adamantan-1-yl(2-(4-fluorophenyl)-6-hydroxybenzo[b]thiophen-3-yl)methanone; and
(3r,5r,7r)-adamantan-1-yl(3-(4-fluorophenyl)-6-hydroxybenzo[b]thiophen-2-yl)methanone;
or a pharmaceutically acceptable salt thereof.

In another aspect, disclosed is a method for treatment of an estrogen-related medical disorder. The method may comprise administering to a subject in need of such treatment a composition comprising a therapeutically effective amount of at least one compound of formula (I) or a pharmaceutically acceptable salt thereof. The method may comprise administering to a subject in need of such treatment a composition comprising a therapeutically effective amount of at least one compound of formula (II) or a pharmaceutically acceptable salt thereof.

The estrogen-related medical disorder may be selected from the group consisting of: cancer, inflammation, osteoporosis, vaginal atrophy, central nervous system diseases, and cardiovascular system diseases. The central nervous system disease may be selected from the group consisting of Alzheimer's Disease and mild cognitive impairment. The cardiovascular disease may be thrombosis. The cancer may be selected from the group consisting of breast cancer, ovarian cancer, prostate cancer, and lung cancer. The breast cancer may be a tamoxifen resistant breast cancer or a triple negative breast cancer.

The at least one compound of formula (I) may be selected from the group consisting of: 3-(1-(2-(4-((6-hydroxy-2-(4-hydroxyphenyl)benzo[b]thiophen-3-yl)oxy)phenoxy)ethyl)piperidin-4-yl)propyl nitrate; 4-(6-hydroxy-3-(4-(2-(piperidin-1-yl)ethoxy)phenoxy)benzo[b]thiophen-2-yl)phenyl 1-((nitrooxy)methyl)cyclopropanecarboxylate; 2-(4-fluorophenyl)-3-(4-(2-(piperidin-1-yl)ethoxy)phenoxy)benzo[b]thiophen-6-yl 1-((nitrooxy)methyl)cyclopropanecarboxylate; 3-(1-(2-(4-((6-hydroxy-3-(4-hydroxyphenyl)benzo[b]thiophen-2-yl)oxy)phenoxy)ethyl)piperidin-4-yl)propyl nitrate; 4-(6-hydroxy-2-(4-(2-(piperidin-1-yl)ethoxy)phenoxy)benzo[b]thiophen-3-yl)phenyl 1-((nitrooxy)methyl)cyclopropanecarboxylate; 3-(4-fluorophenyl)-2-(4-(2-(piperidin-1-yl)ethoxy)phenoxy)benzo[b]thiophen-6-yl 1-((nitrooxy)methyl)cyclopropanecarboxylate; 2-(4-fluorophenyl)-3-(4-(trifluoromethyl)benzoyl)benzo[b]thiophen-6-yl 1-((nitrooxy)methyl)cyclopropanecarboxylate; (1-(((2-(4-fluorophenyl)-3-(4-(trifluoromethyl)benzoyl)benzo[b]thiophen-6-yl)oxy)methyl)cyclopropyl)methyl nitrate; 3-(4-fluorophenyl)-2-(4-(trifluoromethyl)benzoyl)benzo[b]thiophen-6-yl 1-((nitrooxy)methyl)cyclopropanecarboxylate; (1-(((3-(4-fluorophenyl)-2-(4-(trifluoromethyl)benzoyl)benzo[b]thiophen-6-yl)oxy)methyl)cyclopropyl)methyl nitrate; 3-(cyclopropanecarbonyl)-2-(4-fluorophenyl)benzo[b]thiophen-6-yl 1-((nitrooxy)methyl)cyclopropanecarboxylate; (1-(((3-(cyclopropanecarbonyl)-2-(4-fluorophenyl)benzo[b]thiophen-6-yl)oxy)methyl)cyclopropyl)methyl nitrate; 2-(cyclopropanecarbonyl)-3-(4-fluorophenyl)benzo[b]thiophen-6-yl 1-((nitrooxy)methyl)cyclopropanecarboxylate; (1-(((2-(cyclopropanecarbonyl)-3-(4-fluorophenyl)benzo[b]thiophen-6-yl)oxy)methyl)cyclopropyl)methyl nitrate; 2-(4-fluorophenyl)-3-isonicotinoylbenzo[b]thiophen-6-yl 1-((nitrooxy)methyl)cyclopropanecarboxylate; (1-(((2-(4-fluorophenyl)-3-isonicotinoylbenzo[b]thiophen-6-yl)oxy)methyl)cyclopropyl)methyl nitrate; 3-(4-fluorophenyl)-2-isonicotinoylbenzo[b]thiophen-6-yl 1-((nitrooxy)methyl)cyclopropanecarboxylate; (1-(((3-(4-fluorophenyl)-2-isonicotinoylbenzo[b]thiophen-6-yl)oxy)methyl)cyclopropyl)methyl nitrate; 2-(4-fluorophenyl)-3-isobutyrylbenzo[b]thiophen-6-yl 1-((nitrooxy)methyl)cyclopropanecarboxylate; (1-(((2-(4-fluorophenyl)-3-isobutyrylbenzo[b]thiophen-6-yl)oxy)methyl)cyclopropyl)methyl nitrate; 3-(4-fluorophenyl)-2-isobutyrylbenzo[b]thiophen-6-yl 1-((nitrooxy)methyl)cyclopropanecarboxylate; (1-(((3-(4-fluorophenyl)-2-isobutyrylbenzo[b]thiophen-6-yl)oxy)methyl)cyclopropyl)methyl nitrate; 3-(4-ethynylbenzoyl)-2-(4-fluorophenyl)benzo[b]thiophen-6-yl 1-((nitrooxy)methyl)cyclopropanecarboxylate; (1-(((3-(4-ethynylbenzoyl)-2-(4-fluorophenyl)benzo[b]thiophen-6-yl)oxy)methyl)cyclopropyl)methyl nitrate; 2-(4-ethynylbenzoyl)-3-(4-fluorophenyl)benzo[b]thiophen-6-yl 1-((nitrooxy)methyl)cyclopropanecarboxylate; (1-(((2-(4-ethynylbenzoyl)-3-(4-fluorophenyl)benzo[b]thiophen-6-yl)oxy)methyl)cyclopropyl)methyl nitrate; 2-(4-fluorophenyl)-3-(4-methylbenzoyl)benzo[b]thiophen-6-yl 1-((nitrooxy)methyl)cyclopropanecarboxylate; (1-(((2-(4-fluorophenyl)-3-(4-methylbenzoyl)benzo[b]thiophen-6-yl)oxy)methyl)cyclopropyl)methyl nitrate; 3-(4-fluorophenyl)-2-(4-methylbenzoyl)benzo[b]thiophen-6-yl 1-((nitrooxy)methyl)cyclopropanecarboxylate; (1-(((3-(4-fluorophenyl)-2-(4-methylbenzoyl)benzo[b]thiophen-6-yl)oxy)methyl)cyclopropyl)methyl nitrate; 2-(4-fluorophenyl)-3-(4-(1-(4-fluorophenyl)-1H-1,2,3-triazol-4-yl)benzoyl)benzo[b]thiophen-6-yl 1-((nitrooxy)methyl)cyclopropanecarboxylate; (1-(((2-(4-fluorophenyl)-3-(4-(1-(4-fluorophenyl)-1H-1,2,3-triazol-4-yl)benzoyl)benzo[b]thiophen-6-yl)oxy)methyl)cyclopropyl)methyl nitrate; 3-(4-fluorophenyl)-2-(4-(1-(4-fluorophenyl)-1H-1,2,3-triazol-4-yl)benzoyl)benzo[b]thiophen-6-yl 1-((nitrooxy)methyl)cyclopropanecarboxylate; (1-(((3-(4-fluorophenyl)-2-(4-(1-(4-fluorophenyl)-1H-1,2,3-triazol-4-yl)benzoyl)benzo[b]thiophen-6-yl)oxy)methyl)cyclopropyl)methyl nitrate; 3-((3r,5r,7r)-adamantane-1-carbonyl)-2-(4-fluorophenyl)benzo[b]thiophen-6-yl 1-((nitrooxy)methyl)cyclopropanecarboxylate; (1-(((3-((3r,5r,7r)-adamantane-1-carbonyl)-2-(4-fluorophenyl)benzo[b]thiophen-6-yl)oxy)methyl)cyclopropyl)methyl nitrate; 2-((3r,5r,7r)-adamantane-1-carbonyl)-3-(4-fluorophenyl)benzo[b]thiophen-6-yl 1-((nitrooxy)methyl)cyclopropanecarboxylate; (1-(((2-((3r,5r,7r)-adamantane-1-carbonyl)-3-(4-fluorophenyl)benzo[b]thiophen-6-yl)oxy)methyl)cyclopropyl)methyl nitrate; and pharmaceutically acceptable salts thereof.

The at least one compound of formula (II) may be selected from the group consisting of: (2-(4-fluorophenyl)-6-hydroxybenzo[b]thiophen-3-yl)(4-(trifluoromethyl)phenyl) methanone; (3-(4-fluorophenyl)-6-hydroxybenzo[b]thiophen-2-yl)(4-(trifluoromethyl)phenyl)methanone; cyclopropyl(2-(4-fluorophenyl)-6-hydroxybenzo[b]thiophen-3-yl)methanone; cyclopropyl(3-(4-fluorophenyl)-6-hydroxybenzo[b]thiophen-2-yl)methanone; (2-(4-fluorophenyl)-6-hydroxybenzo[b]thiophen-3-yl)(pyridin-4-yl)methanone; (3-(4-fluorophenyl)-6-hydroxybenzo[b]thiophen-2-yl)(pyridin-4-yl)methanone; 1-(2-(4-fluorophenyl)-6-hydroxybenzo[b]thiophen-3-yl)-2-methylpropan-1-one; 1-(3-(4-fluorophenyl)-6-hydroxybenzo[b]thiophen-2-yl)-2-methylpropan-1-one; (4-ethynylphenyl)(2-(4-fluorophenyl)-6-hydroxybenzo[b]thiophen-3-yl)methanone; (4-ethynylphenyl)(3-(4-fluorophenyl)-6-hydroxybenzo[b]thiophen-2-yl)methanone; (2-(4-fluorophenyl)-6-hydroxybenzo[b]thiophen-3-yl)(p-tolyl)methanone; (3-(4-fluorophenyl)-6-hydroxybenzo[b]thiophen-2-yl)(p-tolyl)methanone; (4-(1-(4-fluorophenyl)-1H-1,2,3-triazol-4-yl)phenyl)(2-(4-fluorophenyl)-6-hydroxybenzo[b]thiophen-3-yl)methanone; (4-(1-(4-fluorophenyl)-1H-1,2,3-triazol-4-yl)phenyl)(3-(4-fluorophenyl)-6-hydroxybenzo[b]thiophen-2-yl)methanone; (3r,5r,7r)-adamantan-1-yl(2-(4-fluorophenyl)-6-hydroxybenzo[b]thiophen-3-yl)methanone; (3r,5r,7r)-adamantan-1-yl(3-(4-fluorophenyl)-6-hydroxybenzo[b]thiophen-2-yl)methanone; and pharmaceutically acceptable salts thereof.

In another aspect, disclosed is a method of identifying a cancer in a subject. The method may comprise obtaining a test sample from the subject having cancer, and determining an amount of protein kinase C alpha (PKCα) in the test sample. If the amount of PKCα in the test sample is greater than an amount of PKCα in a test sample from a subject not having cancer, then the cancer may be sensitive to at least one compound of formula (I) or a pharmaceutically acceptable salt thereof, or at least one compound of formula (II) or a pharmaceutically acceptable salt thereof.

The at least one compound of formula (I) may be selected from the group consisting of: 3-(1-(2-(4-((6-hydroxy-2-(4-hydroxyphenyl)benzo[b]thiophen-3-yl)oxy)phenoxy)ethyl)piperidin-4-yl)propyl nitrate; 4-(6-hydroxy-3-(4-(2-(piperidin-1-yl)ethoxy)phenoxy)benzo[b]thiophen-2-yl)phenyl 1-((nitrooxy)methyl)cyclopropanecarboxylate; 2-(4-fluorophenyl)-3-(4-(2-(piperidin-1-yl)ethoxy)phenoxy)benzo[b]thiophen-6-yl 1-((nitrooxy)methyl)cyclopropanecarboxylate; 3-(1-(2-(4-((6-hydroxy-3-(4-hydroxyphenyl)benzo[b]thiophen-2-yl)oxy)phenoxy)ethyl)piperidin-4-yl)propyl nitrate; 4-(6-hydroxy-2-(4-(2-(piperidin-1-yl)ethoxy)phenoxy)benzo[b]thiophen-3-yl)phenyl 1-((nitrooxy)methyl)cyclopropanecarboxylate; 3-(4-fluorophenyl)-2-(4-(2-(piperidin-1-yl)ethoxy)phenoxy)benzo[b]thiophen-6-yl 1-((nitrooxy)methyl)cyclopropanecarboxylate; 2-(4-fluorophenyl)-3-(4-(trifluoromethyl)benzoyl)benzo[b]thiophen-6-yl 1-((nitrooxy)methyl)cyclopropanecarboxylate; (1-(((2-(4-fluorophenyl)-3-(4-(trifluoromethyl)benzoyl)benzo[b]thiophen-6-yl)oxy)methyl)cyclopropyl)methyl nitrate; 3-(4-fluorophenyl)-2-(4-(trifluoromethyl)benzoyl)benzo[b]thiophen-6-yl 1-((nitrooxy)methyl)cyclopropanecarboxylate; (1-(((3-(4-fluorophenyl)-2-(4-(trifluoromethyl)benzoyl)benzo[b]thiophen-6-yl)oxy)methyl)cyclopropyl)methyl nitrate; 3-(cyclopropanecarbonyl)-2-(4-fluorophenyl)benzo[b]thiophen-6-yl 1-((nitrooxy)methyl)cyclopropanecarboxylate; (1-(((3-(cyclopropanecarbonyl)-2-(4-fluorophenyl)benzo[b]thiophen-6-yl)oxy)methyl)cyclopropyl)methyl nitrate; 2-(cyclopropanecarbonyl)-3-(4-fluorophenyl)benzo[b]thiophen-6-yl 1-((nitrooxy)methyl)cyclopropanecarboxylate; (1-(((2-(cyclopropanecarbonyl)-3-(4-fluorophenyl)benzo[b]thiophen-6-yl)oxy)methyl)cyclopropyl)methyl nitrate; 2-(4-fluorophenyl)-3-isonicotinoylbenzo[b]thiophen-6-yl 1-((nitrooxy)methyl)cyclopropanecarboxylate; (1-(((2-(4-fluorophenyl)-3-isonicotinoylbenzo[b]thiophen-6-yl)oxy)methyl)cyclopropyl)methyl nitrate; 3-(4-fluorophenyl)-2-isonicotinoylbenzo[b]thiophen-6-yl 1-((nitrooxy)methyl)cyclopropanecarboxylate; (1-(((3-(4-fluorophenyl)-2-isonicotinoylbenzo[b]thiophen-6-yl)oxy)methyl)cyclopropyl)methyl nitrate; 2-(4-fluorophenyl)-3-isobutyrylbenzo[b]thiophen-6-yl 1-((nitrooxy)methyl)cyclopropanecarboxylate; (1-(((2-(4-fluorophenyl)-3-isobutyrylbenzo[b]thiophen-6-yl)oxy)methyl)cyclopropyl)methyl nitrate; 3-(4-fluorophenyl)-2-isobutyrylbenzo[b]thiophen-6-yl 1-((nitrooxy)methyl)cyclopropanecarboxylate; (1-(((3-(4-fluorophenyl)-2-isobutyrylbenzo[b]thiophen-6-yl)oxy)methyl)cyclopropyl)methyl nitrate; 3-(4-ethynylbenzoyl)-2-(4-fluorophenyl)benzo[b]thiophen-6-yl 1-((nitrooxy)methyl)cyclopropanecarboxylate; (1-(((3-(4-ethynylbenzoyl)-2-(4-fluorophenyl)benzo[b]thiophen-6-yl)oxy)methyl)cyclopropyl)methyl nitrate; 2-(4-ethynylbenzoyl)-3-(4-fluorophenyl)benzo[b]thiophen-6-yl 1-((nitrooxy)methyl)cyclopropanecarboxylate; (1-(((2-(4-ethynylbenzoyl)-3-(4-fluorophenyl)benzo[b]thiophen-6-yl)oxy)methyl)cyclopropyl)methyl nitrate; 2-(4-fluorophenyl)-3-(4-methylbenzoyl)benzo[b]thiophen-6-yl 1-((nitrooxy)methyl)cyclopropanecarboxylate; (1-(((2-(4-fluorophenyl)-3-(4-methylbenzoyl)benzo[b]thiophen-6-yl)oxy)methyl)cyclopropyl)methyl nitrate; 3-(4-fluorophenyl)-2-(4-methylbenzoyl)benzo[b]thiophen-6-yl 1-((nitrooxy)methyl)cyclopropanecarboxylate; (1-(((3-(4-fluorophenyl)-2-(4-methylbenzoyl)benzo[b]thiophen-6-yl)oxy)methyl)cyclopropyl)methyl nitrate; 2-(4-fluorophenyl)-3-(4-(1-(4-fluorophenyl)-1H-1,2,3-triazol-4-yl)benzoyl)benzo[b]thiophen-6-yl 1-((nitrooxy)methyl)cyclopropanecarboxylate; (1-(((2-(4-fluorophenyl)-3-(4-(1-(4-fluorophenyl)-1H-1,2,3-triazol-4-yl)benzoyl)benzo[b]thiophen-6-yl)oxy)methyl)cyclopropyl)methyl nitrate; 3-(4-fluorophenyl)-2-(4-(1-(4-fluorophenyl)-1H-1,2,3-triazol-4-yl)benzoyl)benzo[b]thiophen-6-yl 1-((nitrooxy)methyl)cyclopropanecarboxylate; (1-(((3-(4-fluorophenyl)-2-(4-(1-(4-fluorophenyl)-1H-1,2,3-triazol-4-yl)benzoyl)benzo[b]thiophen-6-yl)oxy)methyl)cyclopropyl)methyl nitrate; 3-((3r,5r,7r)-adamantane-1-carbonyl)-2-(4-fluorophenyl)benzo[b]thiophen-6-yl 1-((nitrooxy)methyl)cyclopropanecarboxylate; (1-(((3-((3r,5r,7r)-adamantane-1-carbonyl)-2-(4-fluorophenyl)benzo[b]thiophen-6-yl)oxy)methyl)cyclopropyl)methyl nitrate; 2-((3r,5r,7r)-adamantane-1-carbonyl)-3-(4-fluorophenyl)benzo[b]thiophen-6-yl 1-((nitrooxy)methyl)cyclopropanecarboxylate; (1-(((2-((3r,5r,7r)-adamantane-1-carbonyl)-3-(4-fluorophenyl)benzo[b]thiophen-6-yl)oxy)methyl)cyclopropyl)methyl nitrate; and pharmaceutically acceptable salts thereof.

The at least one compound of formula (II) may be selected from the group consisting of: (2-(4-fluorophenyl)-6-hydroxybenzo[b]thiophen-3-yl)(4-(trifluoromethyl)phenyl)methanone; (3-(4-fluorophenyl)-6-hydroxybenzo[b]thiophen-2-yl)(4-(trifluoromethyl)phenyl)methanone; cyclopropyl(2-(4-fluorophenyl)-6-hydroxybenzo[b]thiophen-3-yl)methanone; cyclopropyl(3-(4-fluorophenyl)-6-hydroxybenzo[b]thiophen-2-yl)methanone; (2-(4-fluorophenyl)-6-hydroxybenzo[b]thiophen-3-yl)(pyridin-4-yl)methanone; (3-(4-fluorophenyl)-6-hydroxybenzo[b]thiophen-2-yl)(pyridin-4-yl)methanone; 1-(2-(4-fluorophenyl)-6-hydroxybenzo[b]thiophen-3-yl)-2-methylpropan-1-one; 1-(3-(4-fluorophenyl)-6-hydroxybenzo[b]thiophen-2-yl)-2-methylpropan-1-one;

(4-ethynylphenyl)(2-(4-fluorophenyl)-6-hydroxybenzo[b]thiophen-3-yl)methanone; (4-ethynylphenyl)(3-(4-fluorophenyl)-6-hydroxybenzo[b]thiophen-2-yl)methanone; (2-(4-fluorophenyl)-6-hydroxybenzo[b]thiophen-3-yl)(p-tolyl)methanone; (3-(4-fluorophenyl)-6-hydroxybenzo[b]thiophen-2-yl)(p-tolyl)methanone; (4-(1-(4-fluorophenyl)-1H-1,2,3-triazol-4-yl)phenyl)(2-(4-fluorophenyl)-6-hydroxybenzo[b]thiophen-3-yl)methanone; (4-(1-(4-fluorophenyl)-1H-1,2,3-triazol-4-yl)phenyl)(3-(4-fluorophenyl)-6-hydroxybenzo[b]thiophen-2-yl)methanone; (3r,5r,7r)-adamantan-1-yl(2-(4-fluorophenyl)-6-hydroxybenzo[b]thiophen-3-yl)methanone; (3r,5r,7r)-adamantan-1-yl(3-(4-fluorophenyl)-6-hydroxybenzo[b]thiophen-2-yl)methanone; and pharmaceutically acceptable salts thereof.

DETAILED DESCRIPTION

Figure 1:
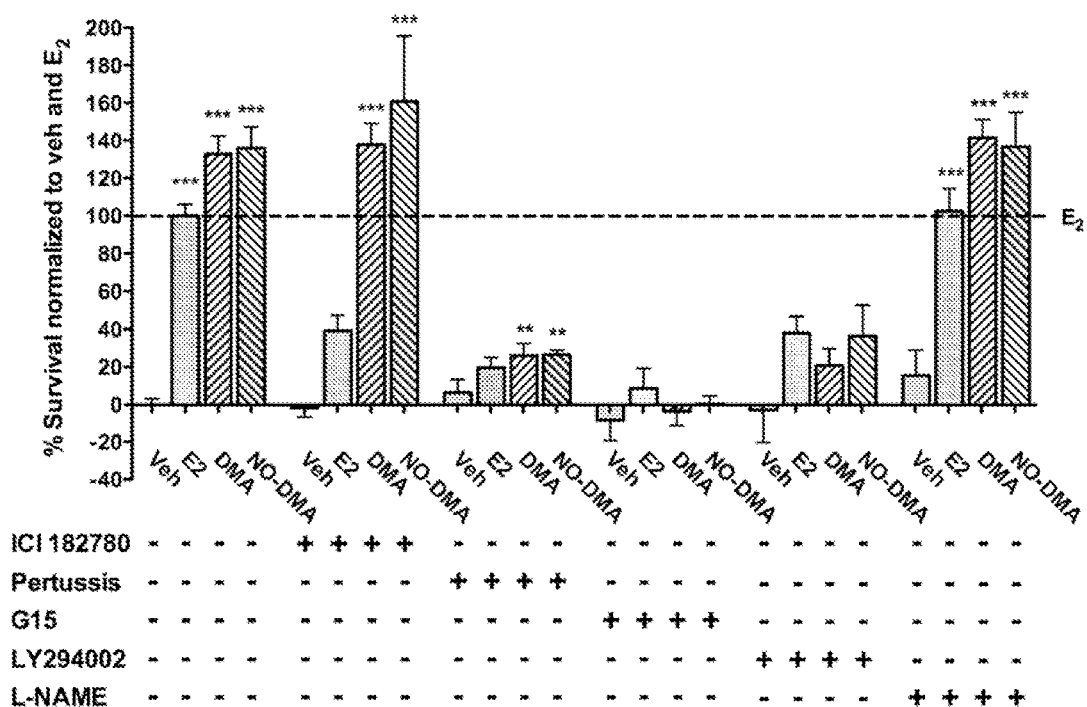
FIG. 1 shows SERM-elicited neuroprotection in primary cortical neurons exposed to OGD is GPR30 dependent. Primary neuronal cultures were subjected to 2 h OGD with compounds added at the start of OGD and inhibitors added 45 min prior to OGD. Cell survival was measured at 24 h. Use of pathway-selective inhibitors indicates that neuroprotection of DMA and NO-DMA is mediated through PI3K-dependent GPR30 signaling in an ER- and NOS-independent manner. Data show mean and S.E.M. normalized to veh. control and E2 (n=6); =$p<0.01$, *=$p<0.001$ compared to veh. control using one-way ANOVA with Dunnett's post hoc test.

In one aspect, the present invention relates to a compound of formula (I)

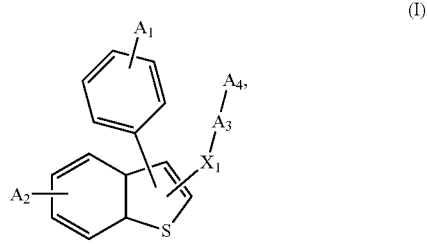

or a pharmaceutically acceptable salt thereof. $A_1$ is selected from the group consisting of halogen, trifluoromethyl, and —$OR_1$. $A_2$ is selected from the group consisting of halogen, trifluoromethyl, and —$OR_2$. $X_1$ is selected from the group consisting of alkyl, —O—, —N(H)—, —S—, —S(=O)—, and —C(=O)—. $A_3$ is selected from the group consisting of alkyl, aryl, cycloalkyl, cycloalkylalkyl, heterocycle, and heteroaryl. $A_4$ is selected from the group consisting of hydrogen, halogen, alkyl, cyano, trifluoromethyl, aryl-heteroaryl wherein the aryl is substituted or unsubstituted (e.g., 1-(4-fluorophenyl)-1H-1,2,3-triazolyl), and —$OR_3$. $R_1$, $R_2$ and $R_3$ are each independently selected from the group consisting of hydrogen, alkyl, —$SO_3R^{x1}$, —$PO_3R^{y1}R^{z1}$, —C(=O)$R^a$, and —$R_4$-$G_1$. $R^{x1}$, $R^{y1}$ and $R^{z1}$, at each occurrence, are independently selected from the group consisting of hydrogen and a pharmaceutically acceptable cation. $R^a$ is alkyl or —OH. $R_4$, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. $G_1$, at each occurrence, is independently selected from the group consisting of hydrogen and —$ONO_2$, wherein at least one of $R_1$, $R_2$ and $R_3$ is —$R_4$-$G_1$, and wherein at least one occurrence of $G_1$ is —$ONO_2$.

The present invention may also relate to a compound of formula (I), wherein $R_4$, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

The present invention may also relate to a compound of formula (I), wherein $R_4$, at each occurrence, is independently selected from the group consisting of alkyl, alkylheterocyclealkyl, and heterocyclealkyl.

The compound of formula (I) may comprise a compound of formula (Ia)

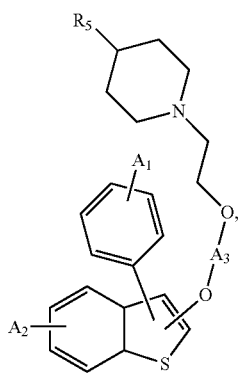

(Ia)

or a pharmaceutically acceptable salt thereof. $A_1$ is selected from the group consisting of halogen, trifluoromethyl, and —$OR_1$. $A_2$ is selected from the group consisting of halogen, trifluoromethyl, and —$OR_2$. $A_3$ is selected from the group consisting of alkyl, aryl, cycloalkyl, cycloalkylalkyl, heterocycle, and heteroaryl. $R_1$ and $R_2$ are each independently selected from the group consisting of hydrogen, alkyl, —$SO_3R^{x1}$, —$PO_3R^{y1}R^{z1}$, —C(=O)$R^a$, and —$R_4$-$G_1$. $R_4$, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. $R_5$ is selected from the group consisting of hydrogen and $C_1$-$C_3$-alkyl-$G_1$. $G_1$, at each occurrence, is independently selected from the group consisting of hydrogen and —$ONO_2$, wherein at least one of $R_1$ and $R_2$ is —$R_4$-$G_1$ and/or $R_5$ is $C_1$-$C_3$-alkyl-$G_1$, and wherein at least one occurrence of $G_1$ is —$ONO_2$. $R^{x1}$, $R^{y1}$ and $R^{z1}$ are each independently selected from the group consisting of hydrogen and a pharmaceutically acceptable cation. $R^a$ is alkyl or —OH.

The compound of formula (I) may comprise a compound of formula (Ia), wherein $R_4$, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

The compound of formula (I) may comprise a compound of formula (Ia), wherein $R_4$, at each occurrence, is independently selected from the group consisting of alkyl, alkylheterocyclealkyl, and heterocyclealkyl.

The compound of formula (I) may comprise a compound of formula (Ia), wherein $R_4$-$G_1$ is

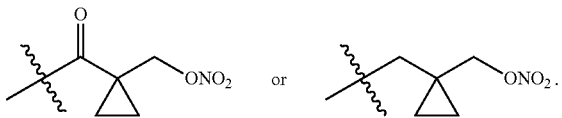

The compound of formula (I) may comprise a compound of formula (Ib)

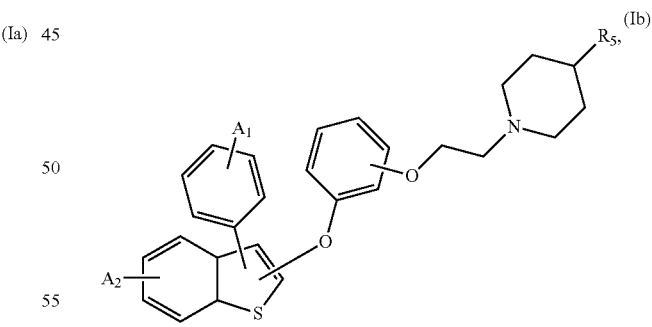

(Ib)

or a pharmaceutically acceptable salt thereof. $A_1$ is selected from the group consisting of halogen, trifluoromethyl, and —$OR_1$. $A_2$ is selected from the group consisting of halogen, trifluoromethyl, and —$OR_2$. $R_1$ and $R_2$ are each independently selected from the group consisting of hydrogen, alkyl, —$SO_3R^{x1}$, —$PO_3R^{y1}R^{z1}$, —C(=O)$R^a$, and —$R_4$-$G_1$. $R_4$, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. $R_5$ is selected from the group consisting of hydrogen and $C_1$-$C_3$-alkyl-$G_1$. $G_1$, at each occurrence, is independently selected from the group consisting of hydrogen and —$ONO_2$, wherein at least one of $R_1$ and $R_2$ is —$R_4$-$G_1$ and/or $R_5$ is $C_1$-$C_3$-alkyl-$G_1$, and wherein at least one occurrence of $G_1$ is —$ONO_2$. $R^{x1}$, $R^{y1}$ and $R^{z1}$ are each independently selected from the group consisting of hydrogen and a pharmaceutically acceptable cation. $R^a$ is alkyl or —OH.

The compound of formula (I) may comprise a compound of formula (Ib), wherein $R_4$, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

The compound of formula (I) may comprise a compound of formula (Ib), wherein $R_4$, at each occurrence, is independently selected from the group consisting of alkyl, alkylheterocyclealkyl, and heterocyclealkyl.

The compound of formula (I) may comprise a compound of formula (Ib), wherein $R_4$-$G_1$ is

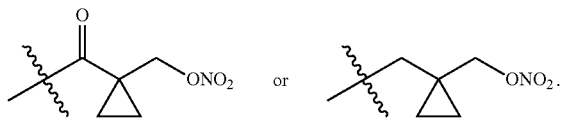

The compound of formula (I) may comprise a compound of formula (Ic)

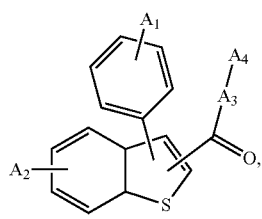

or a pharmaceutically acceptable salt thereof. $A_1$ is selected from the group consisting of halogen, trifluoromethyl, and —$OR_1$. $A_2$ is selected from the group consisting of halogen, trifluoromethyl, and —$OR_2$. $A_3$ is selected from the group consisting of alkyl, aryl, cycloalkyl, cycloalkylalkyl, heterocycle, and heteroaryl. $A_4$ is selected from the group consisting of hydrogen, halogen, alkyl, cyano, trifluoromethyl, aryl-heteroaryl wherein the aryl is substituted or unsubstituted (e.g., 1-(4-fluorophenyl)-1H-1,2,3-triazolyl), and —$OR_3$. $R_1$, $R_2$ and $R_3$ are each independently selected from the group consisting of hydrogen, alkyl, —$SO_3R^{x1}$, —$PO_3R^{y1}R^{z1}$, —C(=O)$R^a$, and —$R_4$-$G_1$. $R^{x1}$, $R^{y1}$ and $R^{z1}$ at each occurrence, are independently selected from the group consisting of hydrogen and a pharmaceutically acceptable cation. $R^a$ is alkyl or —OH. $R_4$, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. $G_1$, at each occurrence, is independently selected from the group consisting of hydrogen and —$ONO_2$, wherein at least one of $R_1$, $R_2$ and $R_3$ is —$R_4$-$G_1$, and wherein at least one occurrence of $G_1$ is —$ONO_2$.

The compound of formula (I) may comprise a compound of formula (Ic), wherein $R_4$, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

The compound of formula (I) may comprise a compound of formula (Ic), wherein $R_4$, at each occurrence, is independently selected from the group consisting of alkyl, alkylheterocyclealkyl, and heterocyclealkyl.

The compound of formula (I) may comprise a compound of formula (Ic), wherein $R_4$-$G_1$ is

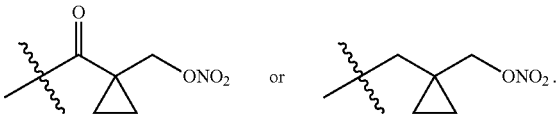

Representative examples of compounds of formula (I), formula (Ia), formula (Ib), and formula (Ic) may include, but are not limited to:
3-(1-(2-(4-((6-hydroxy-2-(4-hydroxyphenyl)benzo[b]thiophen-3-yl)oxy)phenoxy)ethyl)piperidin-4-yl)propyl nitrate;
4-(6-hydroxy-3-(4-(2-(piperidin-1-yl)ethoxy)phenoxy)benzo[b]thiophen-2-yl)phenyl 1-((nitrooxy)methyl)cyclopropanecarboxylate;
2-(4-fluorophenyl)-3-(4-(2-(piperidin-1-yl)ethoxy)phenoxy)benzo[b]thiophen-6-yl 1-((nitrooxy)methyl)cyclopropanecarboxylate;
3-(1-(2-(4-((6-hydroxy-3-(4-hydroxyphenyl)benzo[b]thiophen-2-yl)oxy)phenoxy)ethyl)piperidin-4-yl)propyl nitrate;
4-(6-hydroxy-2-(4-(2-(piperidin-1-yl)ethoxy)phenoxy)benzo[b]thiophen-3-yl)phenyl 1-((nitrooxy)methyl)cyclopropanecarboxylate;
3-(4-fluorophenyl)-2-(4-(2-(piperidin-1-yl)ethoxy)phenoxy)benzo[b]thiophen-6-yl 1-((nitrooxy)methyl)cyclopropanecarboxylate;
2-(4-fluorophenyl)-3-(4-(trifluoromethyl)benzoyl)benzo[b]thiophen-6-yl 1-((nitrooxy)methyl)cyclopropanecarboxylate;
(1-(((2-(4-fluorophenyl)-3-(4-(trifluoromethyl)benzoyl)benzo[b]thiophen-6-yl)oxy)methyl)cyclopropyl)methyl nitrate;
3-(4-fluorophenyl)-2-(4-(trifluoromethyl)benzoyl)benzo[b]thiophen-6-yl 1-((nitrooxy)methyl)cyclopropanecarboxylate;
(1-(((3-(4-fluorophenyl)-2-(4-(trifluoromethyl)benzoyl)benzo[b]thiophen-6-yl)oxy)methyl)cyclopropyl)methyl nitrate;
3-(cyclopropanecarbonyl)-2-(4-fluorophenyl)benzo[b]thiophen-6-yl 1-((nitrooxy)methyl)cyclopropanecarboxylate;
(1-(((3-(cyclopropanecarbonyl)-2-(4-fluorophenyl)benzo[b]thiophen-6-yl)oxy)methyl)cyclopropyl)methyl nitrate;

2-(cyclopropanecarbonyl)-3-(4-fluorophenyl)benzo[b]thiophen-6-yl 1-((nitrooxy)methyl)cyclopropanecarboxylate;
(1-(((2-(cyclopropanecarbonyl)-3-(4-fluorophenyl)benzo[b]thiophen-6-yl)oxy)methyl)cyclopropyl)methyl nitrate;
2-(4-fluorophenyl)-3-isonicotinoylbenzo[b]thiophen-6-yl 1-((nitrooxy)methyl)cyclopropanecarboxylate;
(1-(((2-(4-fluorophenyl)-3-isonicotinoylbenzo[b]thiophen-6-yl)oxy)methyl)cyclopropyl)methyl nitrate;
3-(4-fluorophenyl)-2-isonicotinoylbenzo[b]thiophen-6-yl 1-((nitrooxy)methyl)cyclopropanecarboxylate;
(1-(((3-(4-fluorophenyl)-2-isonicotinoylbenzo[b]thiophen-6-yl)oxy)methyl)cyclopropyl)methyl nitrate;
2-(4-fluorophenyl)-3-isobutyrylbenzo[b]thiophen-6-yl 1-((nitrooxy)methyl)cyclopropanecarboxylate;
(1-(((2-(4-fluorophenyl)-3-isobutyrylbenzo[b]thiophen-6-yl)oxy)methyl)cyclopropyl)methyl nitrate;
3-(4-fluorophenyl)-2-isobutyrylbenzo[b]thiophen-6-yl 1-((nitrooxy)methyl)cyclopropanecarboxylate;
(1-(((3-(4-fluorophenyl)-2-isobutyrylbenzo[b]thiophen-6-yl)oxy)methyl)cyclopropyl)methyl nitrate;
3-(4-ethynylbenzoyl)-2-(4-fluorophenyl)benzo[b]thiophen-6-yl 1-((nitrooxy)methyl)cyclopropanecarboxylate;
(1-(((3-(4-ethynylbenzoyl)-2-(4-fluorophenyl)benzo[b]thiophen-6-yl)oxy)methyl)cyclopropyl)methyl nitrate;
2-(4-ethynylbenzoyl)-3-(4-fluorophenyl)benzo[b]thiophen-6-yl 1-((nitrooxy)methyl)cyclopropanecarboxylate;
(1-(((2-(4-ethynylbenzoyl)-3-(4-fluorophenyl)benzo[b]thiophen-6-yl)oxy)methyl)cyclopropyl)methyl nitrate;
2-(4-fluorophenyl)-3-(4-methylbenzoyl)benzo[b]thiophen-6-yl 1-((nitrooxy)methyl)cyclopropanecarboxylate;
(1-(((2-(4-fluorophenyl)-3-(4-methylbenzoyl)benzo[b]thiophen-6-yl)oxy)methyl)cyclopropyl)methyl nitrate;
3-(4-fluorophenyl)-2-(4-methylbenzoyl)benzo[b]thiophen-6-yl 1-((nitrooxy)methyl)cyclopropanecarboxylate;
(1-(((3-(4-fluorophenyl)-2-(4-methylbenzoyl)benzo[b]thiophen-6-yl)oxy)methyl)cyclopropyl)methyl nitrate;
2-(4-fluorophenyl)-3-(4-(1-(4-fluorophenyl)-1H-1,2,3-triazol-4-yl)benzoyl)benzo[b]thiophen-6-yl 1-((nitrooxy)methyl)cyclopropanecarboxylate;
(1-(((2-(4-fluorophenyl)-3-(4-(1-(4-fluorophenyl)-1H-1,2,3-triazol-4-yl)benzoyl)benzo[b]thiophen-6-yl)oxy)methyl)cyclopropyl)methyl nitrate;
3-(4-fluorophenyl)-2-(4-(1-(4-fluorophenyl)-1H-1,2,3-triazol-4-yl)benzoyl)benzo[b]thiophen-6-yl 1-((nitrooxy)methyl)cyclopropanecarboxylate;
(1-(((3-(4-fluorophenyl)-2-(4-(1-(4-fluorophenyl)-1H-1,2,3-triazol-4-yl)benzoyl)benzo[b]thiophen-6-yl)oxy)methyl)cyclopropyl)methyl nitrate;
3-((3r,5r,7r)-adamantane-1-carbonyl)-2-(4-fluorophenyl)benzo[b]thiophen-6-yl 1-((nitrooxy)methyl)cyclopropanecarboxylate;
(1-(((3-((3r,5r,7r)-adamantane-1-carbonyl)-2-(4-fluorophenyl)benzo[b]thiophen-6-yl)oxy)methyl)cyclopropyl)methyl nitrate;
2-((3r,5r,7r)-adamantane-1-carbonyl)-3-(4-fluorophenyl)benzo[b]thiophen-6-yl 1-((nitrooxy)methyl)cyclopropanecarboxylate;
(1-(((2-((3r,5r,7r)-adamantane-1-carbonyl)-3-(4-fluorophenyl)benzo[b]thiophen-6-yl)oxy)methyl)cyclopropyl)methyl nitrate;
or pharmaceutically acceptable salts thereof.

The compounds of formula (I), formula (Ia), formula (Ib), and/or formula (Ic) may be a nitric oxide (NO) donating selective estrogen receptor modulator (NO-SERM). The compounds of formula (I), formula (Ia), formula (Ib), and/or formula (Ic) may prevent or reduce the risk of thrombosis through the anticoagulant intrinsic and/or extrinsic pathways. The compounds of formula (I), formula (Ia), formula (Ib), and/or formula (Ic) may prevent or reduce the risk of thrombosis even when eNOS is inhibited or inactive. The compounds of formula (I), formula (Ia), formula (Ib), and/or formula (Ic) may be procognitive and neuroprotective even in the presence of NOS dysfunction.

The present invention also relates to methods of treatment of estrogen-related medical disorders. The methods of treatment may include administering to a subject in need of such treatment a composition comprising a therapeutically effective amount of at least one compound of formula (I), formula (Ia), formula (Ib), formula (Ic), and/or pharmaceutically acceptable salts thereof.

An estrogen-related medical disorder may be selected from the group consisting of cancer, inflammation, osteoporosis, vaginal atrophy, central nervous system diseases (e.g., Alzheimer's Disease and mild cognitive impairment), and cardiovascular system diseases (e.g., thrombosis). The cancer may be selected from the group consisting of breast cancer, ovarian cancer, prostate cancer, and lung cancer. The breast cancer may be a tamoxifen resistant breast cancer or a triple negative breast cancer.

The present invention also relates to methods of identifying a cancer in a subject. The methods may include obtaining a test sample from the subject having cancer and determining an amount of PKCα in the test sample. If the amount of PKCα in the test sample is greater than an amount of PKCα in a test sample from a subject not having cancer, then the cancer may be sensitive to at least one compound of formula (I), formula (Ia), formula (Ib), formula (Ic), and/or pharmaceutically acceptable salts thereof.

In another aspect, the present invention relates to a compound of formula (II),

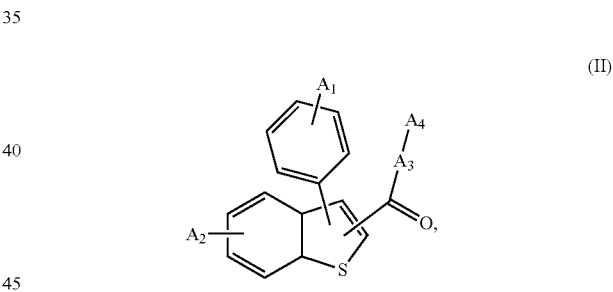

or a pharmaceutically acceptable salt thereof. $A_1$ is selected from the group consisting of halogen, trifluoromethyl, and —$OR_1$. $A_2$ is selected from the group consisting of halogen, trifluoromethyl, and —$OR_2$. $A_3$ is selected from the group consisting of alkyl, aryl, cycloalkyl, cycloalkylalkyl, heterocycle, and heteroaryl. $A_4$ is selected from the group consisting of hydrogen, halogen, alkyl, cyano, trifluoromethyl, aryl-heteroaryl wherein the aryl is substituted or unsubstituted (e.g., 1-(4-fluorophenyl)-1H-1,2,3-triazolyl), and —$OR_3$. $R_1$, $R_2$ and $R_3$ are each independently selected from the group consisting of hydrogen, alkyl, —$SO_3R^{x1}$, —$PO_3R^{y1}R^{z1}$, and —C(=O)$R^a$. $R^{x1}$, $R^{y1}$ and $R^{z1}$, at each occurrence, are independently selected from the group consisting of hydrogen and a pharmaceutically acceptable cation. $R^a$ is alkyl or —OH.

Also provided are compounds of formula (II), wherein $A_1$ is fluoro. $A_1$ may be fluoro located in the 4-position of the phenyl ring to which it is attached. Also provided are compounds of formula (II), wherein $A_2$ is —OH.

Representative examples of compounds of formula (II) may include, but are not limited to:

(2-(4-fluorophenyl)-6-hydroxybenzo[b]thiophen-3-yl)(4-(trifluoromethyl)phenyl)methanone;
(3-(4-fluorophenyl)-6-hydroxybenzo[b]thiophen-2-yl)(4-(trifluoromethyl)phenyl)methanone;
cyclopropyl(2-(4-fluorophenyl)-6-hydroxybenzo[b]thiophen-3-yl)methanone;
cyclopropyl(3-(4-fluorophenyl)-6-hydroxybenzo[b]thiophen-2-yl)methanone;
(2-(4-fluorophenyl)-6-hydroxybenzo[b]thiophen-3-yl)(pyridin-4-yl)methanone;
(3-(4-fluorophenyl)-6-hydroxybenzo[b]thiophen-2-yl)(pyridin-4-yl)methanone;
1-(2-(4-fluorophenyl)-6-hydroxybenzo[b]thiophen-3-yl)-2-methylpropan-1-one;
1-(3-(4-fluorophenyl)-6-hydroxybenzo[b]thiophen-2-yl)-2-methylpropan-1-one;
(4-ethynylphenyl)(2-(4-fluorophenyl)-6-hydroxybenzo[b]thiophen-3-yl)methanone;
(4-ethynylphenyl)(3-(4-fluorophenyl)-6-hydroxybenzo[b]thiophen-2-yl)methanone;
(2-(4-fluorophenyl)-6-hydroxybenzo[b]thiophen-3-yl)(p-tolyl)methanone;
(3-(4-fluorophenyl)-6-hydroxybenzo[b]thiophen-2-yl)(p-tolyl)methanone;
(4-(1-(4-fluorophenyl)-1H-1,2,3-triazol-4-yl)phenyl)(2-(4-fluorophenyl)-6-hydroxybenzo[b]thiophen-3-yl)methanone;
(4-(1-(4-fluorophenyl)-1H-1,2,3-triazol-4-yl)phenyl)(3-(4-fluorophenyl)-6-hydroxybenzo[b]thiophen-2-yl)methanone;
(3r,5r,7r)-adamantan-1-yl(2-(4-fluorophenyl)-6-hydroxybenzo[b]thiophen-3-yl)methanone;
(3r,5r,7r)-adamantan-1-yl(3-(4-fluorophenyl)-6-hydroxybenzo[b]thiophen-2-yl)methanone;
or pharmaceutically acceptable salts thereof.

The compound of formula (II) may be a selective estrogen receptor modulator (SERM). The compounds of formula (II) may prevent or reduce the risk of thrombosis through the anticoagulant intrinsic and/or extrinsic pathways. The compounds of formula may prevent or reduce the risk of thrombosis even when eNOS is inhibited or inactive. The compounds of formula (II) may be procognitive and neuroprotective even in the presence of NOS dysfunction.

The present invention also relates to methods of treatment of estrogen-related medical disorders. The methods of treatment may include administering to a subject in need of such treatment a composition comprising a therapeutically effective amount of at least one compound of formula (II), and/or pharmaceutically acceptable salts thereof.

An estrogen-related medical disorder may be selected from the group consisting of cancer, inflammation, osteoporosis, vaginal atrophy, central nervous system diseases (e.g., Alzheimer's Disease and mild cognitive impairment), and cardiovascular system diseases (e.g., thrombosis). The cancer may be selected from the group consisting of breast cancer, ovarian cancer, prostate cancer, and lung cancer. The breast cancer may be a tamoxifen resistant breast cancer or a triple negative breast cancer.

The present invention also relates to methods of identifying a cancer in a subject. The methods may include obtaining a test sample from the subject having cancer and determining an amount of PKCα in the test sample. If the amount of PKCα in the test sample is greater than an amount of PKCα in a test sample from a subject not having cancer, then the cancer may be sensitive to at least one compound of formula (II), and/or pharmaceutically acceptable salts thereof.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkoxycarbonyl" as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkyl" as used herein, refers to a straight or branched chain hydrocarbon containing from 1 to 10 carbon atoms. Representative examples of alkyl include, but are not limited to, methyl, ethyl, n-propyl, isopropyl, n-butyl, sec-butyl, iso-butyl, tert-butyl, pentyl, hexyl, heptyl, octyl, nonyl, and decyl. The alkyl groups of this invention may be unsubstituted or substituted with 1, 2, or 3 oxo substituents.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "alkylheterocyclealkyl", as used herein, refers to an alkyl group, as defined herein, appended to a heterocycle group, as defined herein, wherein the heterocycle group is appended to the parent molecular moiety through another alkyl group, as defined herein. Representative examples of alkylheteroalkyl include, but are not limited to, ethylpiperidinylpropyl.

The term "aryl" as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl and tetrahydroquinolinyl.

The term "carbonyl" as used herein, refers to a —C(=O)— group.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl. The cycloalkyl groups of this invention may be optionally substituted with 1, 2 or 3 alkyl substituents.

The term "cycloalkylalkyl" as used herein, refers to a cycloalkyl group, as defined herein, appended to the parent molecular moiety through an alkyl group, as defined herein. Representative examples of cycloalkylalkyl include, but are not limited to, cyclopropylmethyl, 1-methylcyclopropylmethyl, cyclohexylmethyl and 3,5-dimethylcyclohexylmethyl.

The term "halogen" as used herein, means Cl, Br, I, or F.

The term "heteroaryl" as used herein, refers to an aromatic monocyclic ring or an aromatic bicyclic ring system. The aromatic monocyclic rings are five or six membered rings containing at least one heteroatom independently selected from the group consisting of N, O and S. The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl and quinolinyl.

The term "heterocycle" as use herein, refers to a non-aromatic monocyclic ring or a non-aromatic bicyclic ring. The non-aromatic monocyclic ring is a three, four, five, six, seven, or eight membered ring containing at least one heteroatom, independently selected from the group consisting of N, O and S. Representative examples of monocyclic ring systems include, but are not limited to, azetidinyl (including azetidin-2-yl, azetidin-3-yl), piperidinyl (including piperidin-2-yl, piperidin-3-yl, piperidin-4-yl), tetrahydrofuranyl (including tetrahydrofuran-2-yl, tetrahydrofuran-3-yl) and tetrahydropyranyl (including tetrahydro-2H-pyran-2-yl, tetrahydro-2H-pyran-3-yl, tetrahydro-2H-pyran-4-yl). The bicyclic heterocycles are exemplified by a monocyclic heterocycle appended to the parent molecular moiety and fused to a monocyclic cycloalkyl heterocycle, as defined herein. Bicyclic ring systems are also exemplified by a bridged monocyclic ring system in which two non-adjacent atoms of the monocyclic ring are linked by a bridge of between one and three additional atoms selected from the group consisting of carbon, nitrogen and oxygen.

The heterocycles of this invention may be optionally substituted with 1, 2 or 3 substituents independently selected from alkyl, alkoxycarbonyl, and oxo.

The term "heterocyclealkyl" as used herein, refers to a heterocycle group, as defined herein, appended to the parent molecular moiety through an alkyl group, as defined herein. Representative examples of heterocyclealkyl include, but are not limited to ethylpiperidinyl and 1-ethylpiperidinyl.

The term "oxo" as used herein, refers to a =O group.

The term "pharmaceutically acceptable cation" refers to a positively charged molecule or atom that is balanced by a negatively charged molecule or atom. Representative pharmaceutically acceptable cations include metal salts such as, for example, aluminum, calcium, copper, ferric, ferrous, lithium, magnesium, manganic salts, manganous, potassium, sodium, zinc, and the like as well as nontoxic ammonium, quaternary ammonium and amine cations including, but not limited to ammonium, tetramethylammonium, tetraethylammonium, methylamine, dimethylamine, trimethylamine, triethylamine, ethylamine, naturally occurring substituted amine, cyclic amines, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, procaine, purines, theobromine, tripropylamine, tromethamine, triethanolamine and the like.

The term "trifluoromethyl" as used herein means a $-CF_3$ group.

In some instances, the number of carbon atoms in a hydrocarbyl substituent (e.g., alkyl or cycloalkyl) is indicated by the prefix "$C_x$-$C_y$—", wherein x is the minimum and y is the maximum number of carbon atoms in the substituent. Thus, for example, "$C_1$-$C_3$-alkyl" refers to an alkyl substituent containing from 1 to 3 carbon atoms.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS OF THE INVENTION

Compounds of the invention (also referred to herein as "agents") include compounds of formula (I)

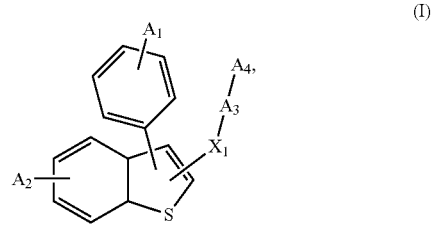

(I)

or a pharmaceutically acceptable salt thereof. $A_1$ is selected from the group consisting of halogen, trifluoromethyl, and $-OR_1$. $A_2$ is selected from the group consisting of halogen, trifluoromethyl, and $-OR_2$. $X_1$ is selected from the group consisting of alkyl, $-O-$, $-N(H)-$, $-S-$, $-S(=O)-$, and $-C(=O)-$. $A_3$ is selected from the group consisting of alkyl, aryl, cycloalkyl, cycloalkylalkyl, heterocycle, and heteroaryl. $A_4$ is selected from the group consisting of hydrogen, halogen, alkyl, cyano, trifluoromethyl, aryl-heteroaryl wherein the aryl is substituted or unsubstituted (e.g., 1-(4-fluorophenyl)-1H-1,2,3-triazolyl), and $-OR_3$. $R_1$, $R_2$ and $R_3$ are each independently selected from the group consisting of hydrogen, alkyl, $-SO_3R^{x1}$, $-PO_3R^{y1}R^{z1}$, $-C(=O)R^a$, and $-R_4$-$G_1$. $R^{x1}$, $R^{y1}$ and $R^{z1}$, at each occurrence, are independently selected from the group consisting of hydrogen and a pharmaceutically acceptable cation. $R^a$ is alkyl or $-OH$. $R_4$, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. $G_1$, at each occurrence, is independently selected from the group consisting of hydrogen and —$ONO_2$, wherein at least one of $R_1$, $R_2$ and $R_3$ is —$R_4$-$G_1$, and wherein at least one occurrence of $G_1$ is —$ONO_2$.

The agent may be a compound of formula (I), wherein $R_4$, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

The agent may be a compound of formula (I), wherein $R_4$, at each occurrence, is independently selected from the group consisting of alkyl, alkylheterocyclealkyl, and heterocyclealkyl.

The compound of formula (I) may comprise a compound of formula (Ia)

together with an alkylene, may form a cycloalkyl, and wherein alkyl may be unsubstituted or substituted with 1, 2, or 3 oxo substituents.

The compound of formula (I) may comprise a compound of formula (Ia), wherein $R_4$, at each occurrence, is independently selected from the group consisting of alkyl, alkylheterocyclealkyl, and heterocyclealkyl.

The compound of formula (I) may comprise a compound of formula (Ia), wherein $R_4$-$G_1$ is

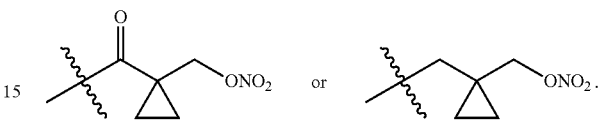

The compound of formula (I) may comprise a compound of formula (Ib)

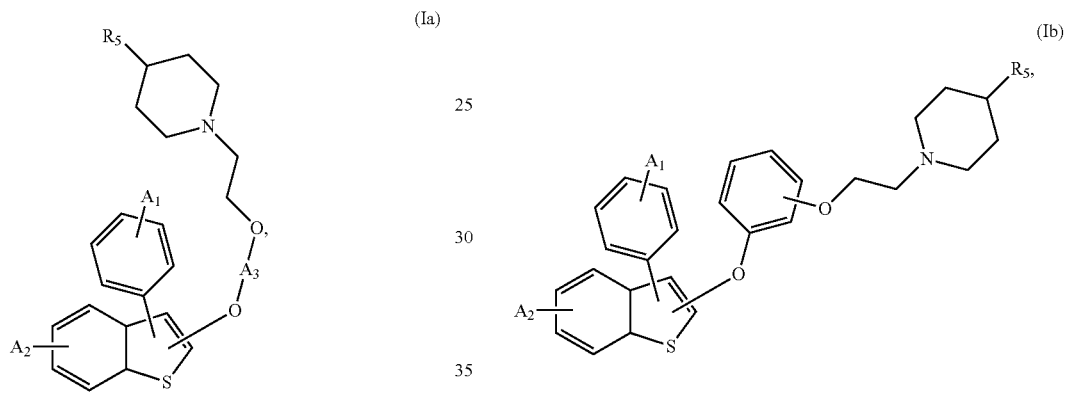

or a pharmaceutically acceptable salt thereof. $A_1$ is selected from the group consisting of halogen, trifluoromethyl, and —$OR_1$. $A_2$ is selected from the group consisting of halogen, trifluoromethyl, and —$OR_2$. $A_3$ is selected from the group consisting of alkyl, aryl, cycloalkyl, cycloalkylalkyl, heterocycle, and heteroaryl. $R_1$ and $R_2$ are each independently selected from the group consisting of hydrogen, alkyl, —$SO_3R^{x1}$, —$PO_3R^{y1}R^{z1}$, —$C(=O)R^a$, and —$R_4$-$G_1$. $R_4$, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. $R_5$ is selected from the group consisting of hydrogen and $C_1$-$C_3$-alkyl-$G_1$. $G_1$, at each occurrence, is independently selected from the group consisting of hydrogen and —$ONO_2$, wherein at least one of $R_1$ and $R_2$ is —$R_4$-$G_1$ and/or $R_5$ is $C_1$-$C_3$-alkyl-$G_1$, and wherein at least one occurrence of $G_1$ is —$ONO_2$. $R^{x1}$, $R^{y1}$ and $R^{z1}$ are each independently selected from the group consisting of hydrogen and a pharmaceutically acceptable cation. $R^a$ is alkyl or —OH.

The compound of formula (I) may comprise a compound of formula (Ia), wherein $R_4$, at each occurrence, is independently selected from the group consisting of alkyl, cycloalkyl, cycloalkylalkyl, heterocyclealkyl, and alkylheterocyclealkyl, wherein any carbon atom on the alkyl group, or a pharmaceutically acceptable salt thereof. $A_1$ is selected from the group consisting of halogen, trifluoromethyl, and —$OR_1$. $A_2$ is selected from the group consisting of halogen, trifluoromethyl, and —$OR_2$. $R_1$ and $R_2$ are each independently selected from the group consisting of hydrogen, alkyl, —$SO_3R^{x1}$, —$PO_3R^{y1}R^{z1}$, —$C(=O)R^a$, and —$R_4$-$G_1$. $R_4$, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. $R_5$ is selected from the group consisting of hydrogen and $C_1$-$C_3$-alkyl-$G_1$. $G_1$, at each occurrence, is independently selected from the group consisting of hydrogen and —$ONO_2$, wherein at least one of $R_1$ and $R_2$ is —$R_4$-$G_1$ and/or $R_5$ is $C_1$-$C_3$-alkyl-$G_1$, and wherein at least one occurrence of $G_1$ is —$ONO_2$. $R^{x1}$, $R^{y1}$ and $R^{z1}$ are each independently selected from the group consisting of hydrogen and a pharmaceutically acceptable cation. $R^a$ is alkyl or —OH.

The compound of formula (I) may comprise a compound of formula (Ib), wherein $R_4$, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

The compound of formula (I) may comprise a compound of formula (Ib), wherein R$_4$, at each occurrence, is independently selected from the group consisting of alkyl, alkylheterocyclealkyl, and heterocyclealkyl.

The compound of formula (I) may comprise a compound of formula (Ib), wherein R$_4$-G$_1$ is

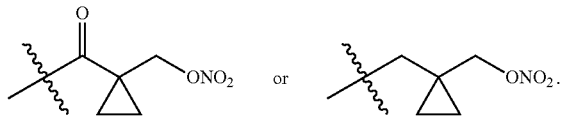

The compound of formula (I) may comprise a compound of formula (Ic)

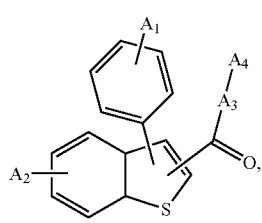

or a pharmaceutically acceptable salt thereof. A$_1$ is selected from the group consisting of halogen, trifluoromethyl, and —OR$_1$. A$_2$ is selected from the group consisting of halogen, trifluoromethyl, and —OR$_2$. A$_3$ is selected from the group consisting of alkyl, aryl, cycloalkyl, cycloalkylalkyl, heterocycle, and heteroaryl. A$_4$ is selected from the group consisting of hydrogen, halogen, alkyl, cyano, trifluoromethyl, aryl-heteroaryl wherein the aryl is substituted or unsubstituted (e.g., 1-(4-fluorophenyl)-1H-1,2,3-triazolyl), and —OR$_3$. R$_1$, R$_2$ and R$_3$ are each independently selected from the group consisting of hydrogen, alkyl, —SO$_3$R$^{x1}$, —PO$_3$R$^{y1}$R$^{z1}$, —C(=O)R$^a$, and —R$_4$-G$_1$. R$^{x1}$, R$^{y1}$ and R$^{z1}$, at each occurrence, are independently selected from the group consisting of hydrogen and a pharmaceutically acceptable cation. R$^a$ is alkyl or —OH. R$_4$, at each occurrence, is independently selected from the group consisting of a substituent comprising 1 to 10 carbon atoms, a substituent comprising 1 to 10 carbon atoms and optionally containing at least one nitrogen atom, a substituent comprising 1 to 10 carbon atoms and optionally containing at least one C=O group, and a substituent comprising 1 to 10 carbon atoms and optionally containing at least one nitrogen and/or at least one C=O group. G$_1$, at each occurrence, is independently selected from the group consisting of hydrogen and —ONO$_2$, wherein at least one of R$_1$, R$_2$ and R$_3$ is —R$_4$-G$_1$, and wherein at least one occurrence of G$_1$ is —ONO$_2$.

The compound of formula (I) may comprise a compound of formula (Ic), wherein R$_4$, at each occurrence, is independently selected from the group consisting of alkyl, cycloalkyl, cycloalkylalkyl, heterocyclealkyl, and alkylheterocyclealkyl, wherein any carbon atom on the alkyl group, together with an alkylene, may form a cycloalkyl, and wherein alkyl may be unsubstituted or substituted with 1, 2, or 3 oxo substituents.

The compound of formula (I) may comprise a compound of formula (Ic), wherein R$_4$, at each occurrence, is independently selected from the group consisting of alkyl, alkylheterocyclealkyl, and heterocyclealkyl.

The compound of formula (I) may comprise a compound of formula (Ic), wherein R$_4$-G$_1$ or

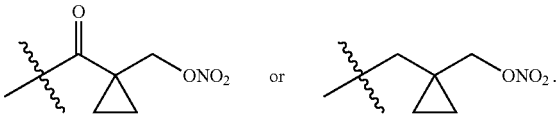

A compound of formula (I) may include, but may not be limited to
3-(1-(2-(4-((6-hydroxy-2-(4-hydroxyphenyl)benzo[b]thiophen-3-yl)oxy)phenoxy)ethyl)piperidin-4-yl)propyl nitrate;
4-(6-hydroxy-3-(4-(2-(piperidin-1-yl)ethoxy)phenoxy)benzo[b]thiophen-2-yl)phenyl 1-((nitrooxy)methyl)cyclopropanecarboxylate;
2-(4-fluorophenyl)-3-(4-(2-(piperidin-1-yl)ethoxy)phenoxy)benzo[b]thiophen-6-yl 1-((nitrooxy)methyl)cyclopropanecarboxylate;
3-(1-(2-(4-((6-hydroxy-3-(4-hydroxyphenyl)benzo[b]thiophen-2-yl)oxy)phenoxy)ethyl)piperidin-4-yl)propyl nitrate;
4-(6-hydroxy-2-(4-(2-(piperidin-1-yl)ethoxy)phenoxy)benzo[b]thiophen-3-yl)phenyl 1-((nitrooxy)methyl)cyclopropanecarboxylate;
3-(4-fluorophenyl)-2-(4-(2-(piperidin-1-yl)ethoxy)phenoxy)benzo[b]thiophen-6-yl 1-((nitrooxy)methyl)cyclopropanecarboxylate;
2-(4-fluorophenyl)-3-(4-(trifluoromethyl)benzoyl)benzo[b]thiophen-6-yl 1-((nitrooxy)methyl)cyclopropanecarboxylate;
(1-(((2-(4-fluorophenyl)-3-(4-(trifluoromethyl)benzoyl)benzo[b]thiophen-6-yl)oxy)methyl)cyclopropyl)methyl nitrate;
3-(4-fluorophenyl)-2-(4-(trifluoromethyl)benzoyl)benzo[b]thiophen-6-yl 1-((nitrooxy)methyl)cyclopropanecarboxylate;
(1-(((3-(4-fluorophenyl)-2-(4-(trifluoromethyl)benzoyl)benzo[b]thiophen-6-yl)oxy)methyl)cyclopropyl)methyl nitrate;
3-(cyclopropanecarbonyl)-2-(4-fluorophenyl)benzo[b]thiophen-6-yl 1-((nitrooxy)methyl)cyclopropanecarboxylate;
(1-(((3-(cyclopropanecarbonyl)-2-(4-fluorophenyl)benzo[b]thiophen-6-yl)oxy)methyl)cyclopropyl)methyl nitrate;
2-(cyclopropanecarbonyl)-3-(4-fluorophenyl)benzo[b]thiophen-6-yl 1-((nitrooxy)methyl)cyclopropanecarboxylate;
(1-(((2-(cyclopropanecarbonyl)-3-(4-fluorophenyl)benzo[b]thiophen-6-yl)oxy)methyl)cyclopropyl)methyl nitrate;
2-(4-fluorophenyl)-3-isonicotinoylbenzo[b]thiophen-6-yl 1-((nitrooxy)methyl)cyclopropanecarboxylate;
(1-(((2-(4-fluorophenyl)-3-isonicotinoylbenzo[b]thiophen-6-yl)oxy)methyl)cyclopropyl)methyl nitrate;
3-(4-fluorophenyl)-2-isonicotinoylbenzo[b]thiophen-6-yl 1-((nitrooxy)methyl)cyclopropanecarboxylate;
(1-(((3-(4-fluorophenyl)-2-isonicotinoylbenzo[b]thiophen-6-yl)oxy)methyl)cyclopropyl)methyl nitrate;
2-(4-fluorophenyl)-3-isobutyrylbenzo[b]thiophen-6-yl 1-((nitrooxy)methyl)cyclopropanecarboxylate;
(1-(((2-(4-fluorophenyl)-3-isobutyrylbenzo[b]thiophen-6-yl)oxy)methyl)cyclopropyl)methyl nitrate;
3-(4-fluorophenyl)-2-isobutyrylbenzo[b]thiophen-6-yl 1-((nitrooxy)methyl)cyclopropanecarboxylate;
(1-(((3-(4-fluorophenyl)-2-isobutyrylbenzo[b]thiophen-6-yl)oxy)methyl)cyclopropyl)methyl nitrate;

3-(4-ethynylbenzoyl)-2-(4-fluorophenyl)benzo[b]thiophen-6-yl 1-((nitrooxy)methyl)cyclopropanecarboxylate;
(1-(((3-(4-ethynylbenzoyl)-2-(4-fluorophenyl)benzo[b]thiophen-6-yl)oxy)methyl)cyclopropyl)methyl nitrate;
2-(4-ethynylbenzoyl)-3-(4-fluorophenyl)benzo[b]thiophen-6-yl 1-((nitrooxy)methyl)cyclopropanecarboxylate;
(1-(((2-(4-ethynylbenzoyl)-3-(4-fluorophenyl)benzo[b]thiophen-6-yl)oxy)methyl)cyclopropyl)methyl nitrate;
2-(4-fluorophenyl)-3-(4-methylbenzoyl)benzo[b]thiophen-6-yl 1-((nitrooxy)methyl)cyclopropanecarboxylate;
(1-(((2-(4-fluorophenyl)-3-(4-methylbenzoyl)benzo[b]thiophen-6-yl)oxy)methyl)cyclopropyl)methyl nitrate;
3-(4-fluorophenyl)-2-(4-methylbenzoyl)benzo[b]thiophen-6-yl 1-((nitrooxy)methyl)cyclopropanecarboxylate;
(1-(((3-(4-fluorophenyl)-2-(4-methylbenzoyl)benzo[b]thiophen-6-yl)oxy)methyl)cyclopropyl)methyl nitrate;
2-(4-fluorophenyl)-3-(4-(1-(4-fluorophenyl)-1H-1,2,3-triazol-4-yl)benzoyl)benzo[b]thiophen-6-yl 1-((nitrooxy)methyl)cyclopropanecarboxylate;
(1-(((2-(4-fluorophenyl)-3-(4-(1-(4-fluorophenyl)-1H-1,2,3-triazol-4-yl)benzoyl)benzo[b]thiophen-6-yl)oxy)methyl)cyclopropyl)methyl nitrate;
3-(4-fluorophenyl)-2-(4-(1-(4-fluorophenyl)-1H-1,2,3-triazol-4-yl)benzoyl)benzo[b]thiophen-6-yl 1-((nitrooxy)methyl)cyclopropanecarboxylate;
(1-(((3-(4-fluorophenyl)-2-(4-(1-(4-fluorophenyl)-1H-1,2,3-triazol-4-yl)benzoyl)benzo[b]thiophen-6-yl)oxy)methyl)cyclopropyl)methyl nitrate;
3-((3r,5r,7r)-adamantane-1-carbonyl)-2-(4-fluorophenyl)benzo[b]thiophen-6-yl 1-((nitrooxy)methyl)cyclopropanecarboxylate;
(1-(((3-((3r,5r,7r)-adamantane-1-carbonyl)-2-(4-fluorophenyl)benzo[b]thiophen-6-yl)oxy)methyl)cyclopropyl)methyl nitrate;
2-((3r,5r,7r)-adamantane-1-carbonyl)-3-(4-fluorophenyl)benzo[b]thiophen-6-yl 1-((nitrooxy)methyl)cyclopropanecarboxylate;
(1-(((2-((3r,5r,7r)-adamantane-1-carbonyl)-3-(4-fluorophenyl)benzo[b]thiophen-6-yl)oxy)methyl)cyclopropyl)methyl nitrate;
and pharmaceutically acceptable salts thereof.

Compounds of the invention (also referred to herein as "agents") include compounds of formula (II)

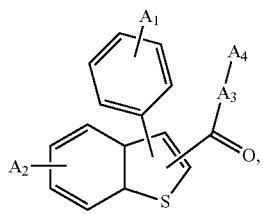

(II)

or a pharmaceutical acceptable salt thereof. $A_1$ is selected from the group consisting of halogen, trifluoromethyl, and —$OR_1$. $A_2$ is selected from the group consisting of halogen, trifluoromethyl, and —$OR_2$. $A_3$ is selected from the group consisting of alkyl, aryl, cycloalkyl, cycloalkylalkyl, heterocycle, and heteroaryl. $A_4$ is selected from the group consisting of hydrogen, halogen, alkyl, cyano, trifluoromethyl, aryl-heteroaryl wherein the aryl is substituted or unsubstituted (e.g., 1-(4-fluorophenyl)-1H-1,2,3-triazolyl), and —$OR_3$. $R_1$, $R_2$ and $R_3$ are each independently selected from the group consisting of hydrogen, alkyl, —$SO_3R^{x1}$, —$PO_3R^{y1}R^{z1}$, and —$C(=O)R^a$. $R^{x1}$, $R^{y1}$ and $R^{z1}$, at each occurrence, are independently selected from the group consisting of hydrogen and a pharmaceutically acceptable cation. $R^a$ is alkyl or —OH.

Also provided are compounds of formula (II), wherein $A_1$ is fluoro. $A_1$ may be fluoro located in the 4-position of the phenyl ring to which it is attached. Also provided are compounds of formula (II), wherein $A_2$ is —OH.

Representative examples of compounds of formula (II) may include, but are not limited to:
(2-(4-fluorophenyl)-6-hydroxybenzo[b]thiophen-3-yl)(4-(trifluoromethyl)phenyl)methanone;
(3-(4-fluorophenyl)-6-hydroxybenzo[b]thiophen-2-yl)(4-(trifluoromethyl)phenyl)methanone;
cyclopropyl(2-(4-fluorophenyl)-6-hydroxybenzo[b]thiophen-3-yl)methanone;
cyclopropyl(3-(4-fluorophenyl)-6-hydroxybenzo[b]thiophen-2-yl)methanone;
(2-(4-fluorophenyl)-6-hydroxybenzo[b]thiophen-3-yl)(pyridin-4-yl)methanone;
(3-(4-fluorophenyl)-6-hydroxybenzo[b]thiophen-2-yl)(pyridin-4-yl)methanone;
1-(2-(4-fluorophenyl)-6-hydroxybenzo[b]thiophen-3-yl)-2-methylpropan-1-one;
1-(3-(4-fluorophenyl)-6-hydroxybenzo[b]thiophen-2-yl)-2-methylpropan-1-one;
(4-ethynylphenyl)(2-(4-fluorophenyl)-6-hydroxybenzo[b]thiophen-3-yl)methanone;
(4-ethynylphenyl)(3-(4-fluorophenyl)-6-hydroxybenzo[b]thiophen-2-yl)methanone;
(2-(4-fluorophenyl)-6-hydroxybenzo[b]thiophen-3-yl)(p-tolyl)methanone;
(3-(4-fluorophenyl)-6-hydroxybenzo[b]thiophen-2-yl)(p-tolyl)methanone;
(4-(1-(4-fluorophenyl)-1H-1,2,3-triazol-4-yl)phenyl)(2-(4-fluorophenyl)-6-hydroxybenzo[b]thiophen-3-yl)methanone;
(4-(1-(4-fluorophenyl)-1H-1,2,3-triazol-4-yl)phenyl)(3-(4-fluorophenyl)-6-hydroxybenzo[b]thiophen-2-yl)methanone;
(3r,5r,7r)-adamantan-1-yl(2-(4-fluorophenyl)-6-hydroxybenzo[b]thiophen-3-yl)methanone;
(3r,5r,7r)-adamantan-1-yl(3-(4-fluorophenyl)-6-hydroxybenzo[b]thiophen-2-yl)methanone;
and pharmaceutically acceptable salts thereof.

Compounds of the invention may act or function as an agonist, an antagonist, a selective estrogen receptor modulator (SERM), or a selective estrogen mimic (SEM). The compounds of may be a nitric oxide (NO) donating selective estrogen receptor modulator (NO-SERM). The compounds may prevent or reduce the risk of thrombosis through the anticoagulant intrinsic and/or extrinsic pathways. The compounds of may prevent or reduce the risk of thrombosis even when eNOS is inhibited or inactive. The compounds may be procognitive and neuroprotective even in the presence of NOS dysfunction.

The present compounds may exist as a pharmaceutically acceptable salt. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like, are contemplated as being within the scope of the present invention.

3. PHARMACEUTICAL COMPOSITIONS

Compounds of the invention may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention [e.g., a compound of formula (I), formula (Ia), formula (Ib), formula (Ic), and/or formula (II)] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), formula (Ia), formula (Ib), formula (Ic), or formula (II), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

4. METHODS OF TREATMENT

The compounds and compositions of the present invention may be used in methods for treatment of estrogen-related medical disorders. The methods of treatment may comprise administering to a subject in need of such treatment a composition comprising a therapeutically effective amount of an agent.

a. Estrogen-Related Disorders

The compositions of the present invention may be used in methods for treatment of estrogen-related medical disorders. An estrogen-related medical disorder may be any medical disorder in which the activity of an estrogen receptor is altered or changed. Alteration of the activity of an estrogen receptor may include upregulation or downregulation of estrogen receptor activity. Alteration of the activity of an estrogen receptor may be the same or different in organs, tissues, and/or cells of a subject.

An estrogen-related medical disorder may also be any medical disorder responsive to modulation of the activity of an estrogen receptor. Such modulation of the activity of an estrogen receptor may include upregulation or downregulation of estrogen receptor activity. The activity of an estrogen receptor may be modulated or altered by an agonist, an antagonist, a selective estrogen receptor modulator (SERM), a selective estrogen mimic (SEM), a nitric oxide donating SERM (NO-SERM), and/or nitric oxide donating SEM (NO-SEM). The activity of the estrogen receptor may be modulated the same or differently in different organs, tissues, and/or cells of a subject.

An estrogen-related medical disorder may further be any medical disorder caused by the action of estrogen and/or lack or blocking of estrogen action. An estrogen-related medical disorder may be any medical disorder responsive to the action of a composition of the present invention and/or lack or blocking of estrogen action by a composition of the present invention.

An estrogen-related medical disorder may be, but is not limited to, cancer, inflammation, osteoporosis, vaginal atrophy, central nervous system diseases, and cardiovascular diseases.

(1) Cancer

The methods of the present invention may be used in methods for treatment of estrogen-related medical disorders, for example, cancer. The cancer may be a breast cancer, a uterine cancer, an ovarian cancer, a prostate cancer, and a lung cancer. Particularly, the breast cancer may be a tamoxifen resistant breast cancer or a triple negative breast cancer. The expression or over expression of PKCα may be indicative of or associated with breast cancer. PKCα may be a biomarker or marker of breast cancer.

The method of treatment may prevent or reduce the risk of cancer. The method of treatment may cause partial or complete regression of cancer in a subject.

The method of treatment may antagonize estrogen action in the breast. The method of treatment may block or limit the mitogenic activities of estrogen in the breast, reproductive system, and the prostate. The method of treatment may cause partial or complete regression of a tamoxifen resistant cancer or tumor. The method of treatment may cause partial or complete regression of a triple negative breast cancer.

(2) Inflammation

The methods of the present invention may be used in methods for treatment of estrogen-related medical disorders, for example, inflammation. The method of treatment may prevent or reduce inflammation in a subject in need of such treatment.

(3) Osteoporosis

The methods of the present invention may be used in methods for treatment of estrogen-related medical disorders, for example, osteoporosis. The methods of treatment may prevent or reduce osteoporosis in a subject in need of such treatment. The methods of treatment may prevent or reduce the loss of bone mineral density in a subject. The methods of treatment may reduce or decrease the rate of bone turnover or fractures. The methods of treatment may improve or maintain bone mineral density in a subject.

(4) Vaginal Atrophy

The methods of the present invention may be used in methods for treatment of estrogen-related medical disorders, for example, vaginal atrophy. The methods of treatment may prevent or reduce vaginal atrophy in a subject in need of such treatment.

(5) Cardiovascular System Diseases

The methods of the present invention may be used in methods for treatment of estrogen-related medical disorders, for example, cardiovascular system diseases. The methods of treatment may enhance or maintain the vasodilatory effects of estradiol on the coronary vasculature. The methods of treatment may decrease or lower low-density lipoprotein cholesterol (LDL-C) levels. The methods of treatment may raise high-density lipoprotein cholesterol (HDL-C) levels. The methods of treatment may decrease or reduce the risk of myocardial infarction. The methods of treatment may prevent or reduce the risk of thrombosis. The methods of treatment may prevent or reduce the risk of stroke. The methods of treatment may prevent or reduce the risk of coronary heart disease.

(6) Central Nervous System Diseases

The methods of the present invention may be used in methods for treatment of estrogen-related medical disorders, for example, central nervous system diseases. The disease of the central nervous system may be Alzheimer's Disease or mild cognitive impairment. The methods of treatment may prevent, reduce, or reverse Alzheimer's Disease or mild cognitive impairment in a subject in need of such treatment. The methods of the present invention may reverse cognitive deficits. The methods of the present invention may restore cognition, long term potentiation (LTP), and synaptic function, and/or be neuroprotective. The methods of present invention may promote neuronal survival and/or hippocampal neurogenesis.

b. Modes of Administration

Methods of treatment may include any number of modes of administering the composition of the present invention. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

5. METHOD OF IDENTIFICATION

The present invention also relates to methods of identifying a cancer in a subject. The method may include obtaining a test sample from the subject having cancer and determining an amount of PKCα in the test sample. If the amount of PKCα in the test sample is greater than an amount of PKCα in a test a sample from a subject not having cancer, then the cancer is sensitive to at least one compound of the invention [e.g., a compound of formula (I), formula (Ia), formula (Ib), formula (Ic), and/or formula (II)].

A cancer sensitive to at least one compound of the invention may overexpress protein kinase C alpha (PKCα) and/or be resistant to tamoxifen. A subject having a cancer sensitive to at least once compound of the invention may have an amount of PKCα that is greater than a subject not having cancer and/or not having a cancer sensitive to at least once compound of the invention.

The present invention has multiple aspects, illustrated by the following non-limiting examples.

6. EXAMPLES

In the examples below, DMA analogues and NO-DMA were prepared for study of neuroprotective and procognitive effects of SERMs and of the potential for an NO-SERM to overcome adverse effects associated with thrombus formation and eNOS dysfunction. We demonstrate that SERM neuroprotection is mediated through a GPR30-dependent mechanism, and extend these results to show that GPR30 mediates the actions of SERMs in restoration of synaptic transmission in an AD transgenic mouse model. We also demonstrate that the procognitive and vasodilatory effects of SERMs are dependent on intact NOS signaling, whereas NO-SERMs preserve action in models where NOS signaling is impaired. This is the first report of an NO-SERM that acts as an antithrombotic agent able to reverse deficits in synaptic transmission and memory in mouse models, while preserving ER binding and retaining efficacy in the face of attenuated eNOS activity.

Example 1

Materials and Methods for Examples 2-8

Synthesis of NO-DMA (i.e., Compound 8) and DMA Analogues.

Synthesis of F-DMA and DMA has been described (96). Synthesis of NO-DMA (3-(1-(2-(4-(6-hydroxy-2-(4-hydroxyphenyl)benzo[b]thiophen-3-yloxy)phenoxy)ethyl)piperidin-4-yl)propyl nitrate) and full characterization data are supplied in Example 11.

Animal Use.

Use of animals was approved by the Institutional Animal Care and Use Committee at the University of Illinois at Chicago. All experiments conformed to the Animal Welfare Act, Guide to Use and Care of Laboratory Animals, and the US Government Principles of the Utilization and Care of Vertebrate Animals Used in Testing, Research and Training guidelines on the ethical use of animals.

Primary Neuron Preparation.

Primary cultures of dissociated cortical neurons were prepared as follows; briefly, cortices were dissected from E16-18 Sprague-Dawley rats (Charles River). After removal of meninges, cortices were manually dissociated and plated at a density of $10^6$ cells/mL into 96-well plates. Twenty-four hours after plating, cultures were grown in Neurobasal A media supplemented with B27, glutamine and pen/strep, with media changes every 3-4 days. In accordance with published protocols, measured levels of glia in culture after DIV2 are <0.5%.

Oxygen Glucose Deprivation (OGD).

The cell media was changed to phenol red-free growing media at least 3 h before OGD. Receptor blockers were added 45 min prior to the start of OGD, and SERMs were added at the start of OGD, with concentrations maintained through media changes. For OGD, the cells were transferred to a hypoxia chamber controlled at 5% $CO_2$ and <1% $O_2$, and growth media was replaced with a physiological salt solution (in mM: NaCl 116, $CaCl_2$ 1.8, $MgSO_4$ 0.8, KCl 5.4, $NaHCO_3$ 14.7, $NaHPO_4$ 1, HEPES 10, pH=7.4). After 2 h OGD, cells were removed from the chamber and growth media was replaced. After 24 h, cell viability was measured by MTT assay using a Dynex MRX 11 micro-plate spectrophotometer.

Electrophysiology.

All experiments used 16-month old male 3×Tg transgenic or age-matched WT background controls. For electrophysiology, mice were rapidly decapitated, and brains were removed into an ice-cold aCSF solution (in mM: NaCl 124, KCl 3.0, $KH_2PO_4$ 1.25, $NaHCO_3$ 25.7, D-glucose 10, L-ascorbate 2.0, $MgSO_4$ 2.5, and $CaCl_2$ 3.3) and sectioned on a tissue chopper into 400 um sections. Slices were transported to a 37° C. solution of aCSF, continuously bubbled with 95% $O_2$/5% $CO_2$, and allowed to recover at least 60 min before experimentation. After placement of a stimulation electrode in the Schaffer commissural fibers and recording electrodes with 2 M NaCl solution into the stratum radiatum of the CA1 area, stimulus intensity was set to evoke submaximal fEPSP and continuously monitored at 20 s intervals for at least 15 min to establish a stable baseline. SERMs (100 nM) and G15 (100 nM) were prepared fresh in perfusate and started at least 30 min before LTP induction to reach a new baseline after enhancement of basal synaptic transmission was observed (97). LTP was induced using a theta burst induction protocol by applying 10 bursts of four pulses at 100 Hz with an interburst interval of 200 msec. Resulting fEPSP was monitored at 20 s intervals for ~60 min post TBS.

CNS Bioavailability & $NO_x$ Measurement.

All experiments were performed on either male C57Bl/6 mice (Charles River Laboratory) or eNOS (−/−) animals. Animals were injected (i.p.) at various time points before sacrifice at the doses specified. After euthanasia via $CO_2$, plasma was collected, and cortices and hippocampi were collected after PBS perfusion and stored at −80° C. Tissue samples were weighed and extracted with methanol. Plasma samples were extracted with cold acetonitrile. Quantitative analysis of drug concentrations in plasma and brain used internal standards spiked into plasma and brain homogenates before liquid extraction with acetonitrile or methanol, and separation and measurement was performed with LC-MS/MS tandem mass spectrometry. The supernatant (deproteinized) was analyzed by chemiluminescence with SIEVERS 280i nitric oxide analyzer.

Step Through Passive Avoidance.

All experiments were performed either on male C57Bl/6 mice or eNOS (−/−) animals. Scopolamine (1 mg/kg) or L-NAME (50 mg/kg) were injected (i.p.) 30 min prior to training, while SERMs (2 mg/kg) were injected 20 min prior to training. Mice were placed in the light compartment of the light/dark box, and as soon as they entered the dark compartment, they received an electric shock (0.5 mA, 60 Hz for 2 seconds). This training was repeated until latency to enter the dark side reached 300 s. At 24 h post-training, animals were individually placed in the light compartment and the latency to enter the dark compartment was recorded with a 300 s cutoff. Details of this widely used assay of behavior have been discussed previously for NO-donor compounds (51, 98, 99).

Aortic Ring Relaxation.

Isolated rings of aortae from male Sprague-Dawley rats (250-300 g) were prepared for isometric tension measurements and were equilibrated for 1 h at an optimal resting tension of 10 mN. Tissues were contracted submaximally with 0.3 µM phenylepinephrine, and after 10-15 m cumulative concentration-response curves for SERMs (0.01-30 µM) were obtained. Some aortic ring preparations were denuded of the endothelium, or were treated with 100 µM L-NAME, prior to assessment of SERM-induced relaxation responses.

Anticoagulation.

SERMs were injected (i.p.) 1 h before blood collection, and L-NAME was injected (i.p.) 30 min before blood collection. The mouse was sedated by exposing it to $CO_2$ until unconscious and blood was collected in 4.5 mL BD Vacutainer Glass Evacuated Blood Collection Tubes (with 0.105 M buffered sodium citrate) by cardiac puncture. The blood samples were centrifuged at 300 g for 30 min to separate the plasma from the blood, and then 200 uL of plasma was taken from each sample and the PT and aPTT were measured using an ACL 7000 Coagulation Analyzer. The analyzer injects 125 µM of PT-fibrinogen (lyophilized rabbit brain calcium thromboplastin with stabilizers, polybrene, buffer and preservatives) to 75 µL of plasma sample to measure the PT, and 75 µL of synthAFAX (0.025 M)+100 µL of $CaCl_2$ (0.02 M) were added to 75 µL of plasma to measure aPTT. The analysis was at 37° C. using a photo sensor at λ=671 nm.

Example 2

Synthesis of an NO-SERM Retaining Nanomolar Binding Affinity for ER

Structural modification of DMA to introduce NO-donor properties, as detailed below, was accomplished without loss of ER binding. Ligand binding affinity was measured by competitive $E_2$ displacement as previously described (52). The $IC_{50}$ values for ERα and ERPβ measured for NO-DMA were 21.4±6.7 nM and 24.4±9.6 nM, respectively. For comparison, ERα $IC_{50}$ values of 21.0±2.7 nM, 7.8±1.9 nM, and 17±0.6 nM were measured for raloxifene, DMA, and F-DMA, respectively.

Example 3

Neuroprotection is Mediated Through GPR30 Receptor Activation, Independent of ERα and NOS Previously, we have shown that the neuroprotective actions of raloxifene and DMA are GPR30-dependent and mediated via PI3K/Akt signaling (53). The oxygen glucose deprivation (OGD) assay was used as a composite model in primary neuronal culture of ischemia-reperfusion injury to determine if addition of NO-donor capacity to DMA altered the mechanism of action. Twenty-four hours after a 2 h glucose deprivation period, 100 nM NO-DMA was observed to elicit robust neuroprotection identical to DMA, as measured by MTT (FIG. 1) or LDH (data not shown) and normalized to estradiol (E2, 10 nM). Blockade of classical ERα signaling by ICI 182780 (100 nM) did not block this effect. However, both pertussis toxin (100 ng/mL), a GPR blocker, and G15 (100 nM), a selective GPR30 antagonist (54), blocked the neuroprotective activity of NO-DMA and DMA. LY294002 (10 µM), a selective PI3K inhibitor, was effective, whereas L-NAME (100 µM), a non-selective NOS antagonist, was ineffective in attenuating neuroprotective activity, supporting the hypothesis that NO-DMA signals through the PI3K/Akt pathway downstream of GPR30 in a manner similar to DMA. In this experimental model, signaling via NOS downstream of PI3/Akt is not indicated.

Example 4

LTP Restoration in an Alzheimer's Mouse Model is GPR30-Dependent

Figure 2:
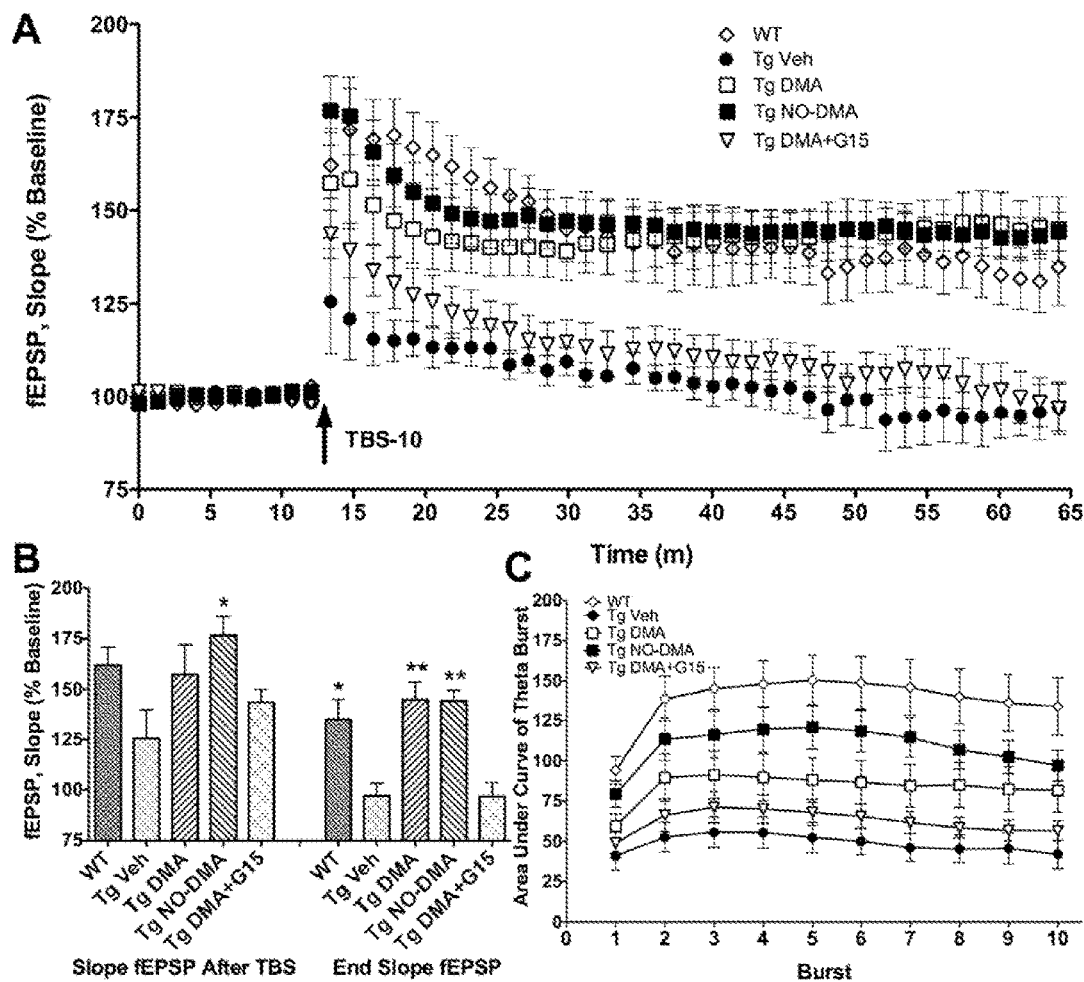
FIG. 2 shows reversal of LTP deficit in aged 3×Tg mice by SERMs is GPR30 dependent. LTP was measured after TBS in the CA1 region of hippocampal sections from 16 month male 3×Tg mice or WT controls. Test compounds (SERMs 100 nM; G15 100 nM) were added 30 min prior to TBS. (A, B) DMA and NO-DMA restored deficits in LTP to WT levels and G15 blocked the actions of DMA. (C) Secondary analysis of theta bursts indicate action both during induction and stabilization of LTP, through a GPR30 dependent mechanism. Data show mean and S.E.M. normalized to baseline (n=4-9); *=$p<0.05$, **=$p<0.01$ compared to transgenic veh. control using one-way ANOVA with Dunnett's post hoc test.
Figure 7:
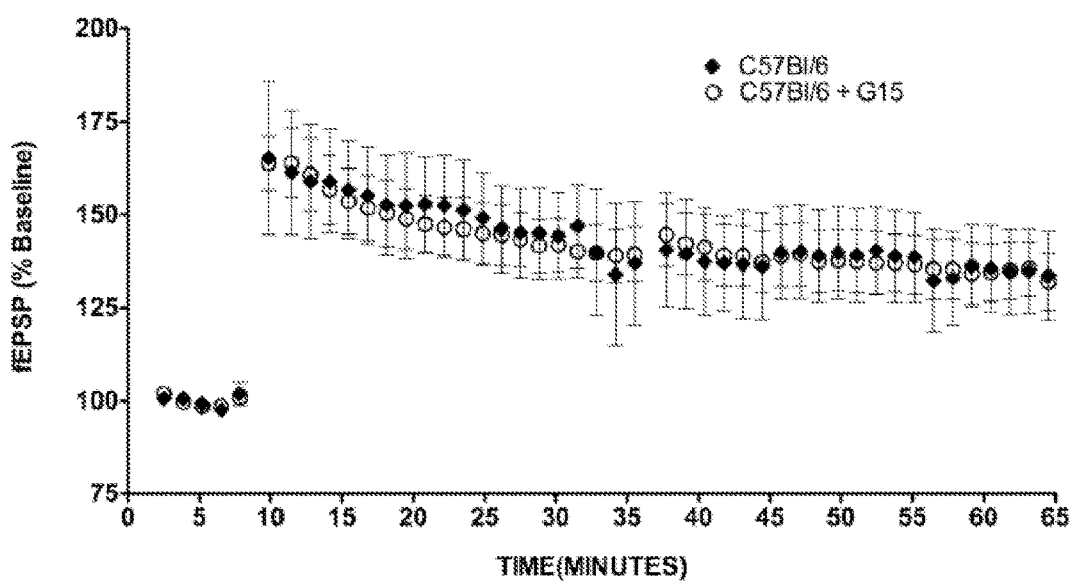
FIG. 7 shows G15 has no effect on LTP in C57Bl/6 mice. LTP was measured after TBS in the CA1 region of hippocampal sections from 8 month old male C57Bl/6 mice. G15 (100 nM) was added 30 min prior to TBS and continued throughout. G15 had no effect on LTP, which reached levels equal to WT background in FIG. 2 for both controls and G15. Data show mean and S.E.M normalized to baseline (n=5-6).
Figure 9:
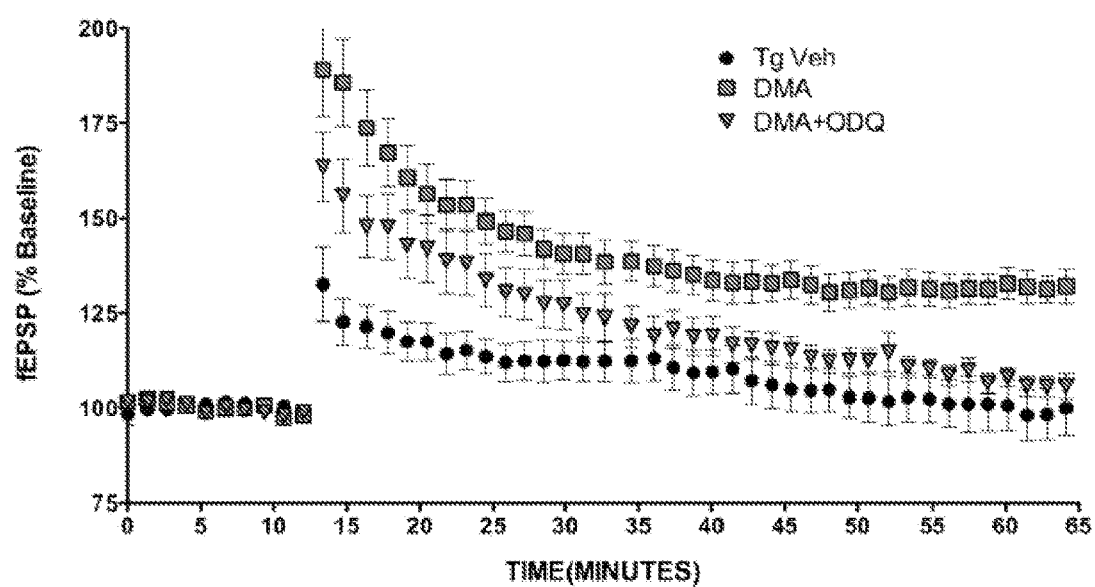
FIG. 9 shows ODQ blocks effect of DMA on LTP in 3×Tg mice. LTP was measured in the CA1 region of hippocampal sections from 16 month male 3×Tg mice using the method detailed in manuscript, with the exception of a variable interburst interval during TBS. ODQ (10 nM) was added 30 min prior to TBS and continued throughout. Data show mean and S.E.M. normalized to baseline (n=9-10).

Long-term potentiation (LTP) in the CA1 field of the hippocampus is a well-studied cellular model for learning and memory. To measure the effect of DMA and NO-DMA in reversing deficits in synaptic plasticity, LTP was induced with a theta burst stimulation (TBS) protocol at Schaffer/commissural fiber synapses in the CA1 field of hippocampal slices from 16-month old male 3×Tg mice. These mice have been shown to have a marked deficit in LTP that becomes apparent at 6 months of age (55). At 16 months, an advanced age at which Alzheimer's-like neuropathology is well developed in these animals, studies on LTP have not previously been reported. We observed a robust, reproducible deficit in LTP in these aged transgenic mice, with field excitatory post-synaptic potentials (fEPSP) showing an end average potentiation of 97.0±6.4% of baseline at 45 min post-TBS, compared to 134.7±10.3% observed in the wild type (WT) controls (FIG. 2A,B). Addition of 100 nM DMA to the aCSF perfusate 30 min prior to induction of LTP resulted in significant reversal of the LTP deficit to an end average potentiation of 144.9±8.7% (FIG. 2A,B). NO-DMA (100 nM) had effects similar to DMA, with an average potentiation of 144.2±5.2% of baseline, with a trend towards increased potentiation over untreated transgenics seen immediately after TBS (FIG. 2A,B). Finally, addition of the GPR30 selective blocker G15 (100 nM) prevented the action of DMA, with end fEPSP approaching levels of untreated transgenics (96.8±7.10%), while having no effect on WT C57Bl/6 slices in the absence of DMA (FIG. 7), suggesting that the GPR30 receptor is critical for the LTP-enhancing effects of SERMs. Preliminary data also indicates that DMA activity is NOS-dependent (FIG. 9).

To determine if drugs enhanced LTP by altering physiological responses during LTP induction, such as NMDA receptor-mediated currents or downstream events involved in expression or stabilization, the postsynaptic responses to theta bursts were quantified as previously described (56, 57). The enhancement of subsequent bursts was augmented by DMA and NO-DMA but not by DMA+G15 (FIG. 2C), suggesting that SERMs may act, at least in part, by enhancing depolarization and NMDA receptor activity during TBS, in addition to downstream actions on the signaling events that lead to stabilization of the LTP response.

Figure 3:
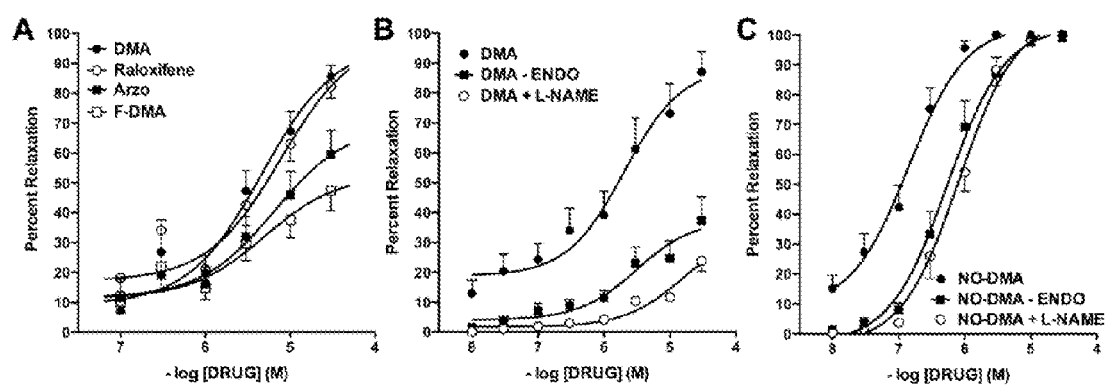
FIG. 3 shows relaxation of isolated aortic rings induced by SERMs and NO-SERM. (A) The $EC_{50}$ values for relaxation were not significantly different ($p>0.05$, one-way ANOVA and Newman-Keuls post-hoc test). The maximal relaxation responses for arzoxifene and FDMA were significantly less than those for DMA and raloxifene ($p<0.05$, one-way ANOVA and Newman-Keuls post-hoc test). Each value represents the mean±S.E.M. (n=7-13). (B) Removal of the endothelium or inhibition of NOS with L-NAME reduced the maximal relaxation response to DMA ($p<0.01$, one-way ANOVA and Newman-Keuls post-hoc test). Each value represents the mean±S.E.M. (n=7). (C) The $EC_{50}$ values for relaxation were significantly increased in the presence of L-NAME or after endothelium removal ($p<0.05$, one-way ANOVA and Newman-Keuls post-hoc test). Each value represents the mean±S.E.M. (n=7).

Example 5 eNOS-Dependent Vascular Relaxation is Retained by NO-SERM in the Absence of eNOS The vasodilator activity of SERMs and NO-SERMs was assessed using isolated aortic ring preparations. All SERMs exhibited dose-dependent relaxation, with raloxifene and DMA showing efficacy approaching 100% relaxation (FIG. 3A). The following $EC_{50}$ values (mean, S.D.) were calculated but not found to be significantly different: FDMA, 2.4±1.2 µM; arzoxifene, 3.3±2.5 µM; DMA, 3.5±2.5 µM; raloxifene, 4.0±2.9 µM, suggesting equal potency as vasodilators for all SERMs studied. Removal of the endothelium or inhibition of NOS by L-NAME resulted in a significant decrease in the efficacy of DMA, indicating that the majority of the vasodilator activity of DMA is mediated through activation of eNOS (FIG. 3B). Thus, SERMs induce relaxation in the aortic ring model at low micromolar concentrations, dependent on intact eNOS/NO signaling. NO-DMA induced maximal relaxation in this model, with at least ten-fold increased potency ($EC_{50}=130\pm90$ nM) over DMA (FIG. 3C). The potency of NO-DMA was reduced in endothelium-denuded tissues ($EC_{50}$ value of $0.90\pm0.69$ µM), and tissues treated with L-NAME ($EC_{50}$ value of $1.0\pm0.54$ µM). NO-DMA was shown to have both endothelium-dependent and -independent vasodilatatory actions, mediated through eNOS and direct NO release.

Example 6

CNS Bioavailable SERMs Increase NO Levels Dependent Upon eNOS Activity

Figure 4:
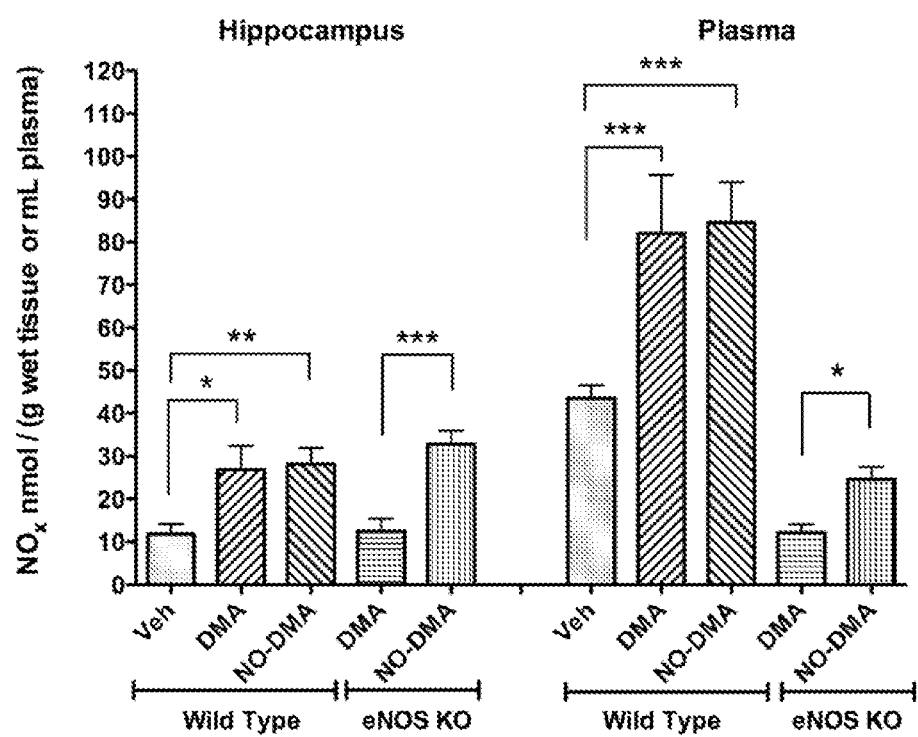
FIG. 4 shows effects of SERM and NO-SERMon NO levels in plasma and CNS of WT and eNOS (−/−) mice. Levels of NO were assessed by measuring breakdown products 1 h after i.p. injection of SERMs (2 mg/kg) using chemiluminescence detection. Both DMA and NO-DMA increased levels of NO in WT mice. The diminished response in eNOS (−/−) was significantly attenuated in DMA relative to NO-DMA treated animals. Data show mean and S.E.M. (n=4-12); *=$p<0.05$, =$p<0.01$, *=$p<0.001$ using one-way ANOVA with Bonferroni's post hoc test.
Figure 8:
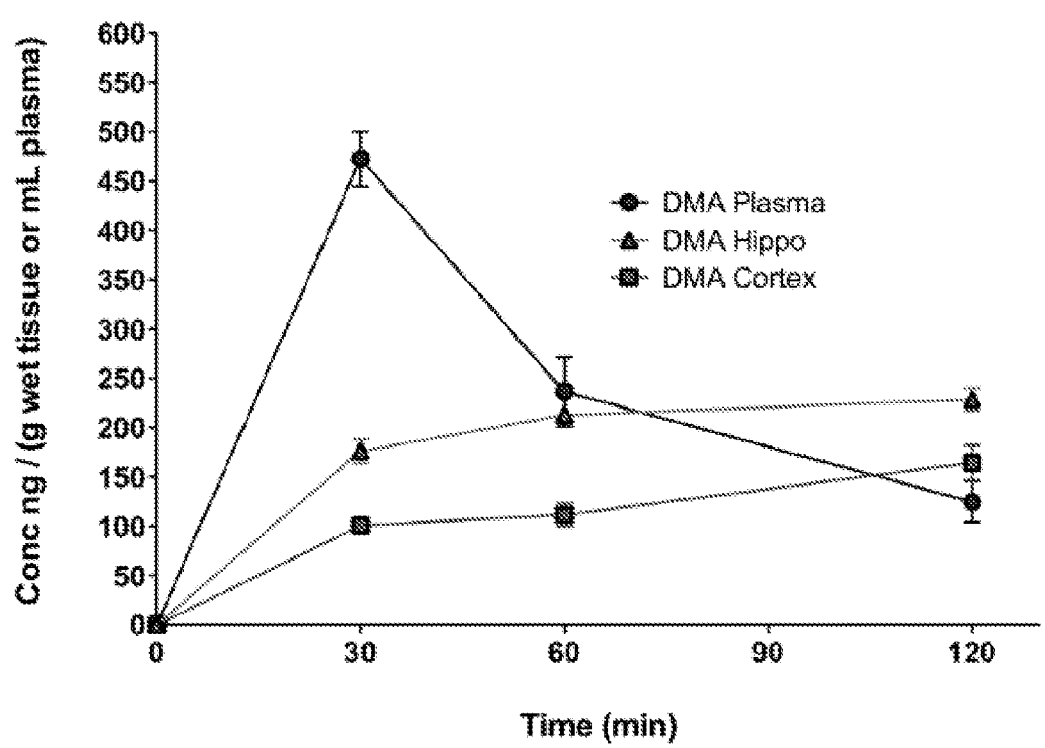
FIG. 8 shows SERM bioavailability in plasma and CNS of WT and eNOS (−/−) mice. Bioavailability was assessed using LC/MS-MS after liquid extraction with internal standard after i.p. injection of 5 mg/kg DMA. DMA shows substantial bioavailability with preferential retention in the hippocampus up to 2 h after administration. Data show mean and S.E.M. (n=4).

The brain and plasma bioavailability of DMA (5 mg/kg; i.p.) was measured in C57Bl/6 mice using LC/MS-MS detection. DMA showed substantial blood brain barrier permeability, with preferential retention in the hippocampus over the cortex (FIG. 8). Brain and plasma NO levels were assessed by measuring metabolic oxidation products, $NO_2^-$ and $NO_3^-$ ($NO_x$), using chemiluminescence detection. One hour after injection of 2 mg/kg DMA or NO-DMA, there was a greater than twofold elevation of $NO_x$ in the hippocampus and plasma (FIG. 4). To assess the relative contribution of eNOS, DMA and NO-DMA were administered to eNOS (−/−) animals. In these animals, DMA had no effect on $NO_x$ in plasma or hippocampus, whereas NO-DMA was found to increase $NO_x$ significantly, in both hippocampus and plasma.

Example 7

Figure 5:
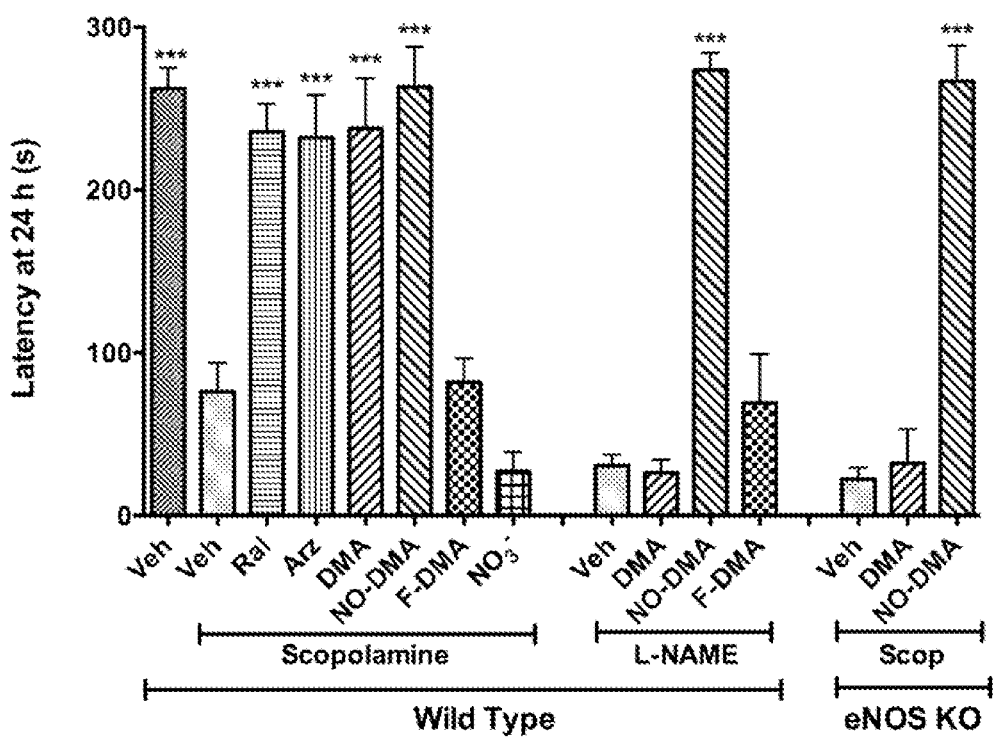
FIG. 5 shows reversal of memory deficit in STPA in WT and eNOS (−/−) mice. Amnestic memory deficit was induced by i.p. injection of either scopolamine (1 mg/kg) or L-NAME (50 mg/kg) 30 min prior to training in C57Bl/6 male mice. SERMs (2 mg/kg) were given 20 min prior to training and latency was assessed 24 h after training with animals being removed from the task if latency >300 s. All SERMs, except F-DMA, restored scopolamine-induced deficits in STPA in WT animals. Against L-NAME-induced deficit, only NO-DMA showed efficacy in reversing memory deficits. In eNOS (−/−) animals subject to scopolamine-induced amnesia, only NO-DMA showed efficacy. Data show mean and S.E.M. (n=4-10); =$p<0.01$, *=$p<0.001$ compared to veh. control using one-way ANOVA with Dunnett's post hoc test.

SERMs Reverse Cholinergic Cognitive Deficits; NO-SERM Reverses the Deficit in eNOS KO Mice To investigate the procognitive effects of SERMs and NO-DMA in an in vivo behavioral model of memory, step-through passive avoidance (STPA) was used in C57Bl/6 mice treated with scopolamine (1 mg/kg) 30 min prior to training. In this assay, memory is tested 24 h and 48 h after training and since drugs are only administered during training, any side effects of drugs, such as sedation are highly unlikely to confound the testing results. A high latency reflects a strong consolidated memory of the aversive stimulus. In scopolamine treated animals, all treatments (2 mg/kg, i.p., 20 min prior to training) except F-DMA and inorganic nitrate induced complete reversal of the memory deficit at 24 h after training (FIG. 5). NO-DMA showed equivalent restoration of protection to DMA. To isolate the procognitive effects due to NO release from NO-DMA, experiments were repeated after administration of L-NAME (50 mg/kg, 30 min prior to training) in place of scopolamine. L-NAME alone resulted in a cognitive deficit that was reversed only by NO-DMA. Similar results were observed in STPA after a scopolamine-induced deficit in eNOS KO mice, strongly implicating eNOS as mediating the procognitive mechanism of action of SERMs and demonstrating the ability of an NO-SERM to circumvent loss of eNOS activity.

Example 8

Figure 6:
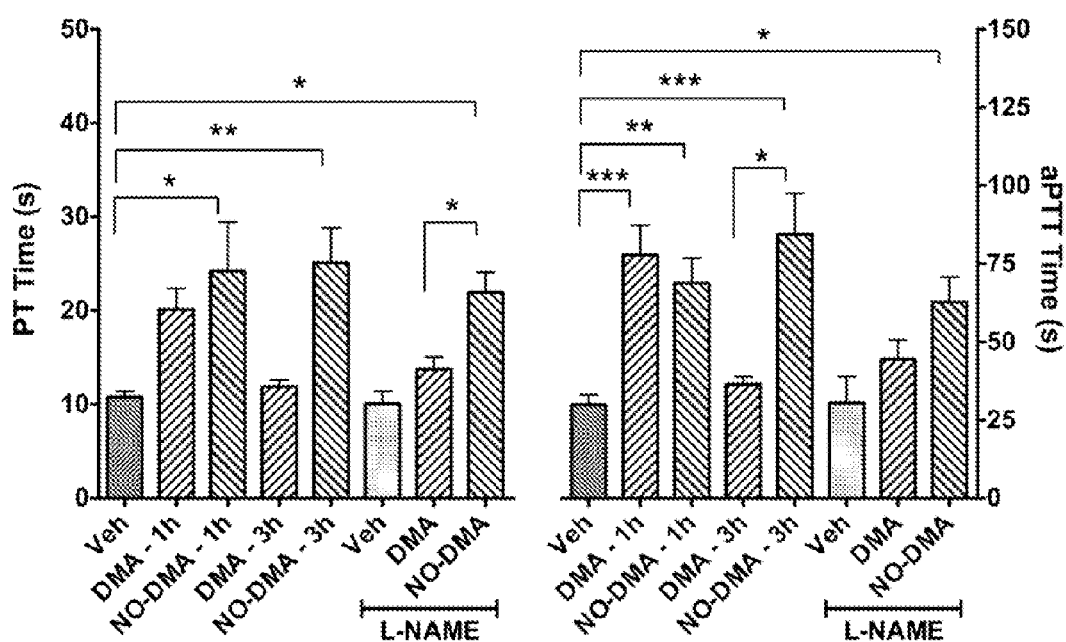
FIG. 6 shows effect of SERMs and NO-SERM on intrinsic (PTT) and extrinsic (aPTT) clotting cascades. Blood was collected by cardiac puncture and PTT and aPTT were determined 1 or 3 h after i.p. drug administration (2 mg/kg). The anticoagulant activity of DMA was shorter lived than that of NO-DMA and did not persist in the presence of NOS blockade. Data show mean and S.E.M. (n=2-8); *=$p<0.05$, =$p<0.01$, *=$p<0.001$ using one-way ANOVA with Bonferroni's post hoc test.

SERMs Act Through the Intrinsic Pathway; NO-SERM Activates Both Intrinsic and Extrinsic Anticoagulant Pathways NO has been implicated in directly reducing clotting (28), therefore prothrombin (PT) and activated thromboplastin times (aPTT) were evaluated for DMA and NO-DMA. At 1 h, both DMA and NO-DMA significantly increased aPTT, and both increased PT, but only NO-DMA reached significance (FIG. 6). After 3 h, the effect of DMA had decreased to that of control samples, whereas the effect of NO-DMA remained significantly higher than control. To test the anticoagulant activity of compounds in models of impaired NOS function, mice injected with L-NAME (50 mg/kg, 30 m prior to collection) were administered DMA or NO-DMA (2 mg/kg, 1 h prior to collection), and only NO-DMA showed significant anticoagulation compared to control, with the increase in PT significantly higher than DMA.

Example 9

Summary of Examples 2-8

Although $2^{nd}$ generation selective estrogen receptor modulators (SERMs) have overcome gynecological issues, the potential of estrogens in neuroprotective and procognitive therapy is limited by the risk of thrombotic events. The critical period hypothesis also posits an attenuated response to estrogens with age. The $3^{rd}$ generation SERM, desmethylarzoxifene (DMA), was shown in hippocampal slices from older 3xTg Alzheimer's transgenic mice to restore synaptic function with dependence on GPR30. Neuroprotection in primary rat neurons was also GPR30 dependent. DMA was brain bioavailable and reversed cholinergic cognitive deficits, however, DMA was not able to restore cognition in mice in which endothelial nitric oxide synthase (eNOS) was inhibited or deleted. A novel NO-donating SERM (NO-SERM) was designed and shown to be procognitive and neuroprotective even with NOS dysfunction: the NO-SERM restored cognition in eNOS (−/−) mice, restored LTP in 3xTg hippocampal slices, and protected primary neurons against ischemia-reperfusion injury. The activation of eNOS underlies the cardiovascular benefits of estrogens and relaxation of aortic rings was induced by SERMs, although only NO-DMA retained efficacy in the absence of eNOS. Finally, in contrast to DMA, NO-DMA was shown to reduce thrombosis through both the intrinsic and extrinsic pathway, even when eNOS was inhibited. The NO-SERM retains the positive attributes of SERMs, without the thrombotic side effect, and can be of use in an aging population in which eNOS activity is attenuated.

Example 10

Discussion of Examples 2-8

Menopause has been associated with dementia, depression, and anxiety, and the management of such effects with safe and effective hormone therapies is a largely unmet need. Women entering menopause report memory and concentration difficulties (58, 59), and the age-adjusted AD mortality rate was shown to be 21.7% higher for women than for men (60). Estrogen replacement therapy has been reported to improve or maintain levels of cognitive function in postmenopausal women, and to reduce the risk of Alzheimer's disease (AD), observations in accord with proposed roles for estrogen in the brain in protection, growth and differentiation of neurons (7, 61-63). However, adverse events associated with estrogen commend SERMs as an alternative approach. The beneficial effects of estrogen in the CNS, bone, and cardiovascular systems underlie the search for an ideal SERM that can preserve these beneficial effects while minimizing or antagonizing the potentially serious adverse effects of estrogens in sex organs.

The benzothiophene SERM, raloxifene, has demonstrated significant beneficial effects on bone and lipid profiles in postmenopausal women (17-19), with evidence suggesting that CNS and cardiac profiles remain positive (14, 23). Furthermore, raloxifene shows antiestrogenic activity in the breast and endometrium (20, 21). Clinical studies on raloxifene have shown positive signals on cognitive skills (18, 64-66), and procognitive and neuroprotective effects have been reported in female rats (67-69). However, raloxifene has also shown efficacy in male rats (70) and positive cognitive responses have been reported in elderly men (71, 72). The benzothiophene SERMs, raloxifene and DMA, have many characteristics of an ideal SERM of potential use in the CNS, in particular if thrombotic side effects can be abolished.

Relevant to design of an ideal SERM is the interplay between classical ER-mediated signaling and emerging mechanisms of rapid extranuclear signaling, such as via GPR30 (54, 73, 74). Associated with these signaling pathways, are important roles for NO in signaling via activation of eNOS through the PI3K/Akt pathway (25, 26). Estrogen and SERM induced neuroprotection has been reported to be mediated via rapid signaling, including regulation of intracellular $Ca^{2+}$ and phosphorylation of ERK (75, 76). Extranuclear ER, linked to kinase signaling pathways, including PI3K/Akt and Src/ERK/CREB, has been shown to play a role in estrogenic neuroprotection (75, 77), providing direct links to anti-apoptotic mechanisms (78). Estradiol and DMA were observed to elicit neuroprotection in primary neurons subject to ischemia-reperfusion injury, with the novel observation that the actions of estrogen and SERMs were mediated via GPR30 linked to downstream PI3K/Akt, Src, and ERK pathways. This activity was retained by NO-DMA, a NO-SERM that is itself a potent antiestrogen; although neuroprotection in this model system was independent of NOS.

To extend observations on neuronal rescue by SERMs and NO-SERM to a model system for synaptic rescue, the 3×Tg Alzheimer's mouse model was used. These mice represent a more complete model of the disease than some other strains, with progressive production of Aβ in relevant brain areas, plaque and tangle pathology similar to those observed in AD patients, and synaptic transmission and LTP impairment at 6 months of age (55, 79). We chose to study synaptic function in 3×Tg mice at 16 months, representing a model of aging, combined with substantial Aβ and tau neuropathology. Gratifyingly, DMA was observed to restore synaptic deficits, measured by LTP in 3×Tg hippocampal slices; and this activity was again dependent upon GPR30 and retained by NO-DMA.

Relaxation of blood vessels by estrogens and SERMs is mediated by endothelium-independent and -dependent mechanisms, the latter involving activation of eNOS. ER isoforms and GPR30 have been implicated in these actions (80). The vascular effects of raloxifene have been well established in conduit arteries, and recently in resistance arteries (81), supporting therapeutic benefit in preserving endothelial function. Raloxifene was first reported to induce vasodilation by an ER and eNOS-dependent pathway (82), and subsequently shown to activate eNOS via PI3K/Akt (26). In rat aorta, vasodilation was observed in response to all benzothiophene SERMs tested. Relaxation induced by DMA was largely endothelium and eNOS-dependent, whereas NO-DMA retained equivalent potency to DMA even in the absence of endothelium and eNOS.

Cholinergic deficits are the basis of current symptomatic therapy of AD (83). The roles that cholinergic dysfunction may play in early AD and Mild Cognitive Impairment (MCI) have recently been reviewed (84). Amnestic MCI is a putative prodromal stage of Alzheimer's disease and chemical amnesia has frequently been induced in man and animal models in drug discovery and development using cholinergic blockade with scopolamine (85). Benzothiophene SERMs, raloxifene, arzoxifene, and DMA restored the cognitive deficit induced in mice by scopolamine. The concerted actions of eNOS and nNOS are required for normal LTP in the hippocampus, and in tissues from knockout mice, exogenous NO can replace NOS function (38). Therefore, given observations on SERMs and NO-SERM in the vasculature, the use of both NOS inhibition and eNOS (KO) mice was indicated to test the efficacy of DMA and NO-DMA. The procognitive mechanism of action of DMA was identified as being eNOS-dependent; NO-DMA was observed to retain procognitive actions in both paradigms of eNOS-challenge.

The known endothelial dysfunction associated with aging, the decreased expression of eNOS in postmenopausal women, and the potential contribution of eNOS to the critical period hypothesis, commend the further study of therapeutic approaches that reinforce NO/cGMP signaling in combination with ER modulation. Other contributions to age-related pathophysiology, in addition to attenuated eNOS expression, have been proposed, including: inhibition of eNOS by elevation of ADMA (86, 87); depletion of cofactors, notably BH4 (88-90); and eNOS polymorphisms (91). Attenuation of NO-dependent cGMP production by soluble guanylyl cyclase (sGC) has also been linked directly with Aβ. (92) The NO-SERM approach is informative, however, related approaches to combinatorial activation of (1) estrogenic signaling and (2) NO/cGMP signaling are also endorsed (27, 93).

In summary, a prototype NO-SERM was designed and demonstrated to retain the ER binding and classical ERα antagonist actions of the parent SERM, and to provide neuroprotection and synaptic restoration in an AD model, dependent upon GPR30. Against a cholinergic cognitive deficit in mice, neuroprotective SERMs restored memory, however, this procognitive effect was lost when eNOS activity was blocked or absent. The NO-SERM restored cognition after cholinergic insult in eNOS (−/−) mice and NO levels measured after SERM and NO-SERM treatment were compatible with the central role of NO signaling. In AD in particular, a role is emerging for NO in treating cholinergic deficits (49) and attenuating amyloidogenesis (94, 95).

From a therapeutic perspective, the known endothelial dysfunction associated with aging, the decreased expression of eNOS in postmenopausal women, and the potential contribution of eNOS to the critical period hypothesis, commend the further study of NO-SERMs. Related approaches to combinatorial activation of (1) estrogenic signaling and (2) NO/cGMP signaling are also endorsed (27, 89). The ability of an NO-SERM to reduce coagulation by increasing both PT and aPTT to levels comparable to those of clinical anticoagulants, suggests that this approach can also address the risk of thrombosis associated with SERM therapeutics. These findings, coupled with the otherwise excellent safety record of raloxifene in the clinic, support further development of NO-SERMs or combination therapies for AD and other neurodegenerative disorders in the post-menopausal cohort, and suggest utility for this approach in the general population.

Example 11
Synthesis of NO-DMA Compound 8 (i.e., 3-(1-(2-(4-(6-hydroxy-2-(4-hydroxyphenyl)benzo[b]thiophen-3-yloxy)phenoxy)ethyl)piperidin-4-yl)propyl nitrate)
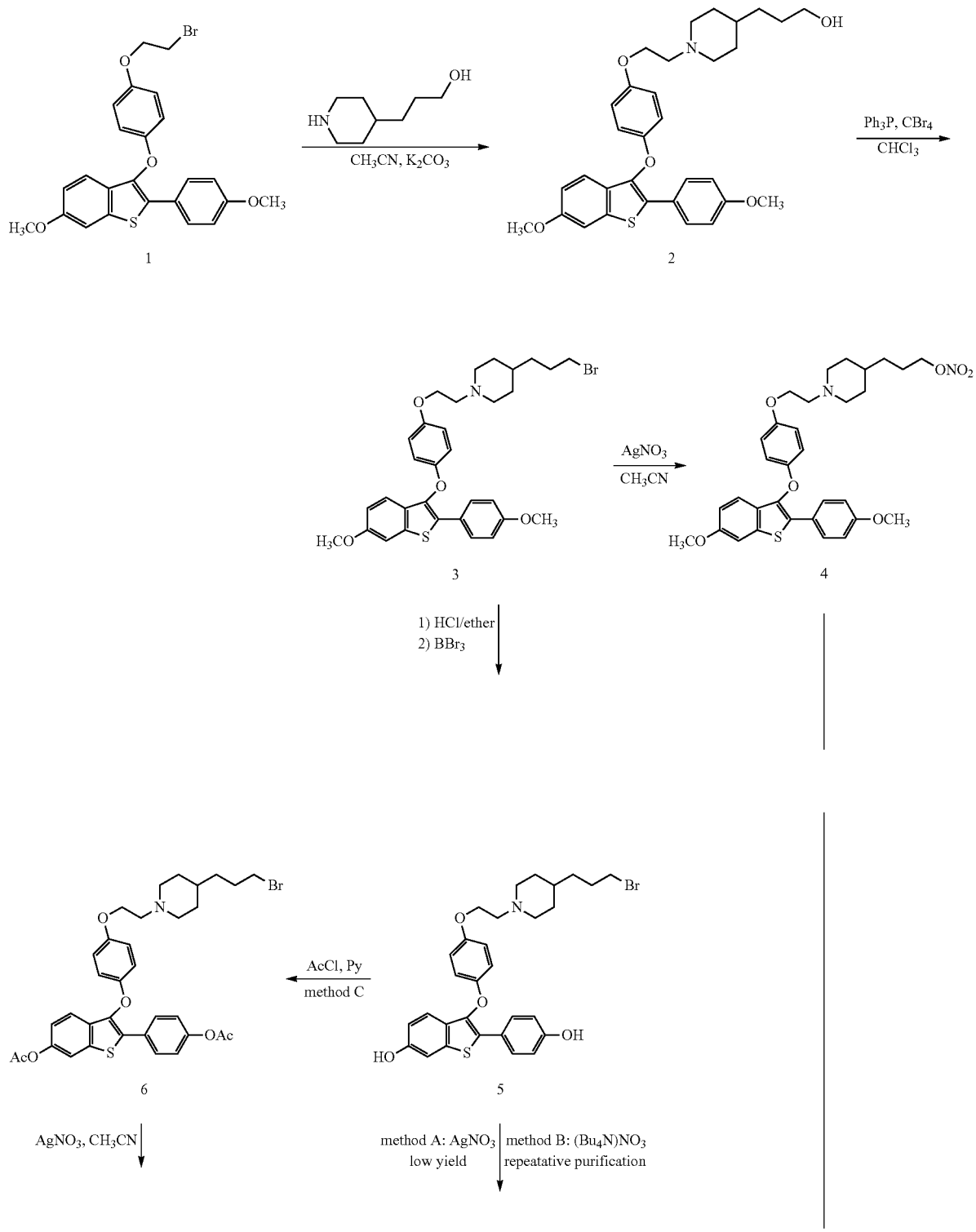

-continued

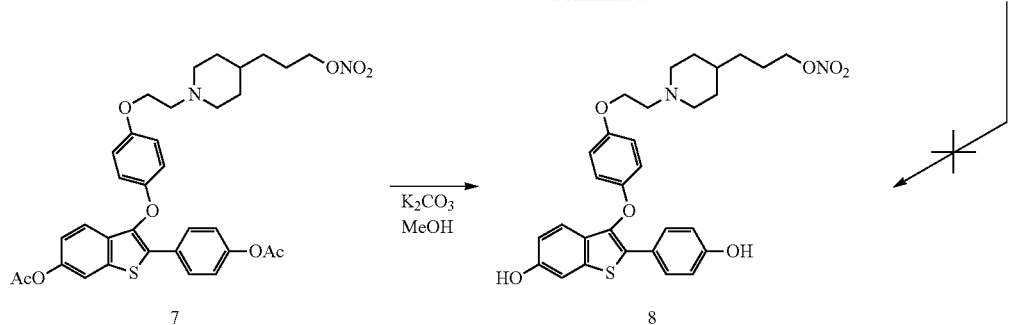

$^1$H and $^{13}$C NMR spectra were obtained with Bruker Ultrashield 400 MHz and Advance 300 MHz spectrometers. Chemical shifts are reported as δ values in parts per million (ppm) relative to tetramethylsilane (TMS) for all recorded NMR spectra. All reagents and solvents were obtained commercially from Acros, Aldrich, and Fluka and were used without purification.

Starting material 1 was synthesized from commercial available 6-methoxy-2-(4-methoxy phenyl)benzo[b]thiophene according to a published method in 6 steps (53). Demethylation of 4 gave complex mixture, might be due to the incompatibility of Lewis acid with organic nitrate. NO-DMA 8 was obtained by the reaction of 5 with silver nitrate in low yield (method A); or by using tetrabutyl ammonium nitrate as nitration reagent, the yield was improved dramatically, but the method suffered from repetitive column purifications to remove ammonium salt (method B); alternatively, the phenol groups of 5 were acetylated and the bromide 6 was converted nitrate 7 using silver salt, 8 was finally obtained with good purity by de-acetylation of 7 in high yield (method C).

Compound 2.

Compound 1 (2.6 g, 5.3 mmol), 4-piperidinepropanol (1.0 g, 6.9 mmol) were dissolved in anhydrous acetonitrile (100 mL) and anhydrous $K_2CO_3$ (2.9 g, 21.5 mmol) was added. The reaction mixture was refluxed for 6 hrs and cooled to room temperature. After filtration, solvent was removed, the residue was dissolved in DCM (150 mL) and washed with water (2×50 mL). Organic phase separated and concentrated. The residue was purified by column chromatography (DCM/MeOH 20:1, 2.9 g, quantitative yield). $^1$H-NMR (Acetone-d$_6$, 400 MHz): δ 7.66-7.69 (m, 2H), 7.42 (d, 1H, J=2.0 Hz), 7.24 (d, 1H, J=8.8 Hz), 6.81-6.93 (m, 7H), 3.97 (t, 2H, J=6.0 Hz), 3.84 (s, 3H), 3.76 (s, 3H), 3.51 (t, 2H, J=6.4 Hz), 2.88-2.91 (m, 2H), 2.63 (t, 2H, J=6.0 Hz), 1.95-2.01 (m, 2H), 1.60-1.62 (m, 2H), 1.46-1.53 (m, 2H), 1.21-1.27 (m, 5H); $^{13}$C-NMR (Acetone-d$_6$, 100 MHz): 160.23, 159.01, 155.19, 152.34, 140.57, 137.56, 129.32, 128.77, 127.06, 125.78, 122.64, 116.95, 116.26, 115.28, 115.05, 106.36, 67.30, 62.64, 58.28, 55.90, 55.52, 55.13, 36.32, 33.62, 33.31, 30.90.

Compound 3.

Compound 2 (1.1 g, 2.0 mmol) was dissolved in chloroform (25 mL), CBr$_4$ (2.7 g, 8.0 mmol) and polymer bound Ph$_3$P (2.6 g, about 3 mmol/g) were added, the reaction mixture was stirred at r.t. overnight. After filtration, solvent was removed, and the residue was purified by column chromatography (DCM/AcOEt/MeOH 3:1:0.2, 1.1 g, 89%). $^1$H-NMR (Acetone-d$_6$, 400 MHz): 7.68-7.72 (m, 2H), 7.46 (d, 1H, J=2.0 Hz), 7.25 (d, 1H, J=8.8 Hz), 6.84-6.97 (m, 7H), 4.00 (t, 2H, J=6.0 Hz), 3.87 (s, 3H), 3.80 (s, 3H), 3.47 (s, 2H, J=6.8 Hz), 2.91-2.94 (m, 2H), 2.67 (t, 2H, J=6.0 Hz), 1.99-2.04 (m, 2H), 1.82-1.89 (m, 2H), 1.62-1.65 (m, 2H), 1.32-1.37 (m, 2H), 1.15-1.24 (m, 3H); δ $^{13}$C-NMR (Acetone-d$_6$, 100 MHz): 160.35, 159.12, 155.29, 152.43, 140.64, 137.63, 129.38, 128.82, 127.10, 125.63, 122.68, 117.00, 116.36, 115.37, 115.12, 106.43, 67.43, 58.30, 55.96, 55.58, 55.06, 35.83, 35.78, 34.98, 33.22, 30.98.

Compound 4.

Compound 3 (110 mg, 0.18 mmol) was dissolved in anhydrous acetonitrile (3 mL), AgNO$_3$ (306 mg, 1.8 mmol) was added. The reaction mixture was stirred at r.t. for 24 h. Solvent was removed and the residue was purified by column chromatography (DCM/AcOEt/MeOH 2:1:0.25, 85 mg, 79%). $^1$H-NMR (Acetone-d$_6$, 400 MHz): δ 7.66-7.72 (m, 2H), 7.43 (d, 1H, J=2.0 Hz), 7.25 (d, 1H, J=8.8 Hz), 6.82-6.95 (m, 7H), 4.49 (t, 2H, J=6.8 Hz), 3.98 (t, 2H, J=6.0 Hz), 3.85 (s, 3H), 3.77 (s, 3H), 2.89-2.92 (m, 2H), 2.64 (t, 2H, J=2.0 Hz), 1.97-2.02 (m, 2H), 1.67-1.73 (m, 2H), 1.61-1.64 (m, 2H), 1.13-1.34 (m, 5H); $^{13}$C-NMR (Acetone-d$_6$, 100 MHz): δ 160.30, 159.07, 155.25, 152.39, 140.62, 137.61, 129.36, 128.81, 127.09, 125.62, 122.67, 116.99, 116.32, 115.32, 115.09, 106.41, 74.69, 67.40, 58.27, 55.94, 55.56, 54.99, 36.03, 33.09, 24.64.

Compound 5.

Compound 3 (240 mg, 0.39 mmol) was dissolved in DCM (5 mL), HCl ether solution (2.0M, 1.0 mL) was added. The reaction mixture was stirred at 4° C. for 2 hr. Solvent was removed, the residue was re-dissolved in DCM (10 mL), cooled in an ice-water bath, BBr$_3$ in DCM (1.0 M, 1 mL) was added dropwise. The reaction mixture was stirred at 4° C. for 3 hr and then at r.t. for another hour. The reaction mixture was poured into ice water (50 mL), neutralized with NaHCO$_3$ and extracted with AcOEt (3×30 mL). Organic solution was combined and concentrated, the residue was purified by column chromatography (DCM/MeOH 50:3, 160 mg, 70%). $^1$H-NMR (Acetone-d$_6$, 400 MHz): δ 7.59-7.62 (m, 2H), 7.32 (d, 1H, J=2.0 Hz), 7.19 (d, 1H, J=8.8 Hz), 6.83-6.89 (m, 7H), 4.06 (t, 2H, J=5.9 Hz), 3.47 (t, 2H, J=6.7 Hz), 3.01-3.04 (m, 2H), 2.77 (t, 2H, J=5.9 Hz), 2.11-2.17 (m, 2H), 1.82-1.90 (m, 2H), 1.65-1.67 (m, 2H), 1.22-1.38 (m, 5H); $^{13}$C-NMR (Acetone-d$_6$, 100 MHz): δ 158.14, 156.63, 154.99, 152.52, 140.31, 137.46, 129.41, 128.06, 126.60, 124.59, 122.67, 116.97, 116.54, 116.30, 115.64, 108.79, 66.85, 58.04, 54.83, 35.61, 35.52, 34.95, 32.68, 30.90.

Compound 6.

Compound 5 (300 mg, 0.52 mmol) was dissolved in DCM (10 mL), pyridine (0.84 mL, 10.3 mmol) and Ac$_2$O (0.34 mL, 3.6 mmol) were added, the reaction mixture was stirred at r.t. overnight. Solvent was removed, the residue was re-dissolved in ethyl acetate (50 mL) and washed with water, organic solution was separated and concentrated, the residue was purified by column chromatography, product was obtained as slightly yellow foam (DCM/MeOH 30:1, 298 mg, 87%). $^1$H-NMR (Acetone-d$_6$, 400 MHz): δ 7.83 (d, 2H, J=8.4 Hz), 7.74 (d, 1H, J=2.0 Hz), 7.40 (d, 1H, J=8.8 Hz), 7.19 (d, 2H, J=8.8 Hz), 7.10 (dd, 1H, J=8.8 Hz, 2.0 Hz), 6.86-6.93 (m, 4H), 4.05 (t, 2H, J=6.0 Hz), 3.47 (t, 2H, J=6.8 Hz), 2.95-2.98 (m, 2H), 2.71 (t, 2H, J=6.0 Hz), 2.29 (s, 3H), 2.26 (s, 3H), 2.06-2.11 (m, 2H), 1.82-1.89 (m, 2H), 1.64-1.66 (m, 2H), 1.32-1.38 (m, 2H), 1.20-1.28 (m, 3H); $^{13}$C-NMR (Acetone-d$_6$, 100 MHz): 169.75, 169.46, 155.42, 152.20, 151.79, 149.90, 141.64, 136.84, 132.49, 130.24, 129.33, 129.24, 123.25, 122.81, 120.61, 117.13, 116.89, 116.46, 67.17, 58.12, 54.93, 35.69, 35.66, 34.98, 32.96, 30.94, 20.93.

Compound 7.

Compound 6 (280 mg, 0.45 mmol) was dissolved in anhydrous acetonitrile (15 mL), AgNO$_3$ (1.1 g, 1.8 mmol) was added. The reaction mixture was stirred at r.t. for 24 h. After filtration, solvent was removed and the residue was purified by column chromatography, product was obtained as slightly yellow foam (DCM/MeOH 30:1, 190 mg, 70%). $^1$H-NMR (Acetone-d$_6$, 400 MHz): δ $^1$H-NMR (Acetone-d$_6$, 400 MHz): δ 7.81 (d, 2H, J=8.8 Hz), 7.71 (d, 1H, J=2.0 Hz), 7.38 (d, 1H, J=8.8 Hz), 7.17 (d, 2H, J=8.8 Hz), 7.08 (dd, 1H, J=8.8 Hz, 2.0 Hz), 6.82-6.92 (m, 4H), 4.48 (t, 2H, J=6.8 Hz), 4.00 (t, 2H, J=6.0 Hz), 2.92-2.95 (m, 2H), 2.68 (t, 2H, J=6.0 Hz), 2.27 (s, 3H), 2.24 (s, 3H), 2.02-2.04 (m, 2H), 1.61-1.74 (m, 4H), 1.16-1.31 (m, 5H); $^{13}$C-NMR (Acetone-d$_6$, 100 MHz): δ 169.69, 169.41, 155.34, 152.12, 151.70, 149.82, 141.58, 136.77, 132.44, 130.19, 129.25, 129.19, 123.18, 122.77, 120.53, 117.08, 116.82, 116.38, 74.65, 67.09, 58.07, 54.85, 35.83, 32.96, 32.79, 24.58, 20.93.

Compound 8.

Method A: Compound 5 (55 mg, 0.095 mmol) was dissolved in anhydrous acetonitrile (2 mL), AgNO$_3$ (160 mg, 0.95 mmol) was added. The reaction mixture was stirred at r.t. overnight. After filtration, solvent was removed and the residue was purified by column chromatography (DCM/AcOEt/MeOH 3:1:0.3), product was obtained as white foam (15 mg, 28%). Method B: Compound 5 (100 mg, 0.17 mmol) was dissolved in anhydrous acetonitrile (5 mL), tetrabutylammonium nitrate (523 mg, 1.7 mmol) was added. The reaction mixture was heated at 70° C. for 8 hrs. Solvent was removed and the residue was purified repeatedly by column chromatography (DCM/AcOEt/MeOH 3:1:0.3) three times, product was obtained as white foam (68 mg, 70%). Method C: Compound 7 (130 mg, 0.2 mmol) was dissolved in a mixture of THF-MeOH—H$_2$O (4.5 mL, 2:2:0.5), K$_2$CO$_3$ (79 mg, 0.58 mmol) was added. The reaction mixture was stirred at r.t. for 1.5 hr. After filtration and concentration, the residue was purified by column chromatography (DCM/MeOH 20:1), product was obtained as white foam (103 mg, 91%). $^1$H-NMR (Acetone-d$_6$, 400 MHz): δ 7.60 (d, 2H, J=8.8 Hz), 7.31 (d, 1H, J=2.0 Hz), 7.19 (d, 1H, J=8.8 Hz), 6.84-6.90 (m, 7H), 4.53 (t, 2H, J=6.7 Hz), 4.03 (t, 2H, J=5.9 Hz), 2.95-2.98 (m, 2H), 2.70 (t, 2H, J=5.9 Hz), 1.98-2.04 (m, 2H), 1.73-1.77 (m, 2H), 1.66-1.69 (m, 2H), 1.19-1.35 (m, 5H); $^{13}$C-NMR (Acetone-d$_6$, 100 MHz): δ 158.14, 156.62, 155.11, 152.50, 140.36, 137.49, 129.43, 128.12, 126.63, 124.64, 122.71, 116.98, 116.56, 116.29, 115.47, 108.81, 74.69, 67.12, 58.21, 54.93, 35.94, 33.03, 32.86, 24.63.

Example 12

Synthesis of NO-SERM 13 and 14

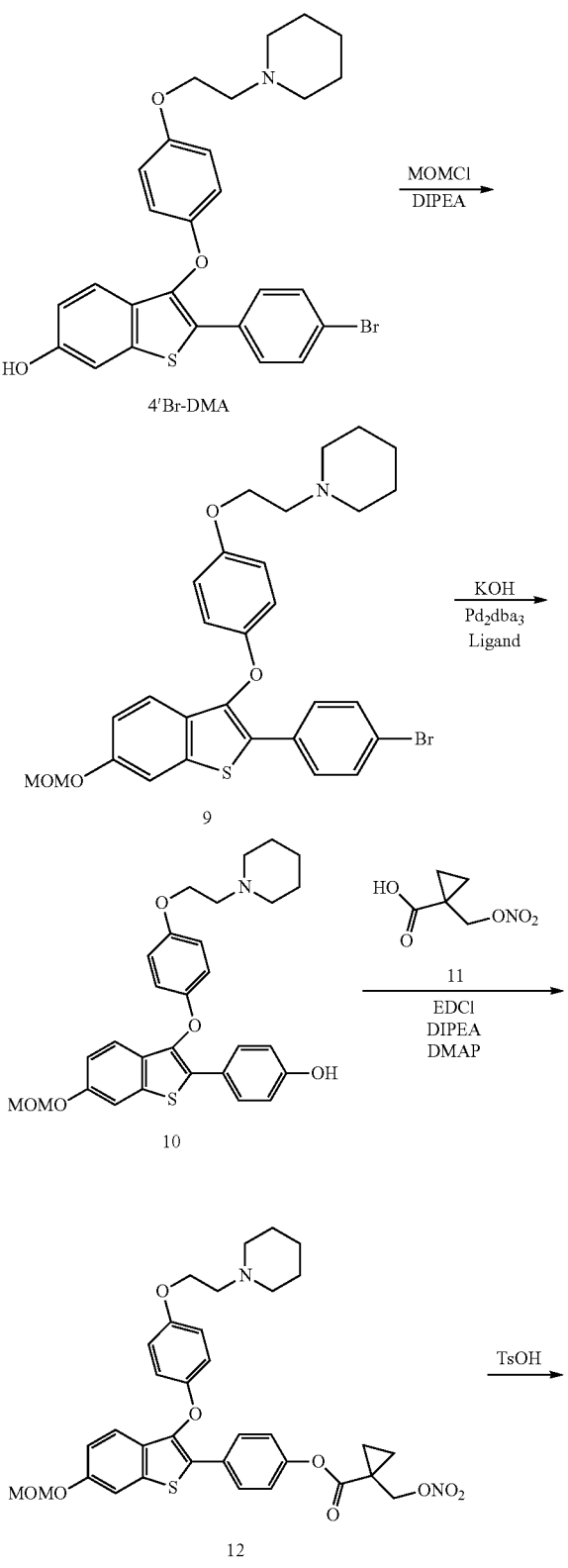

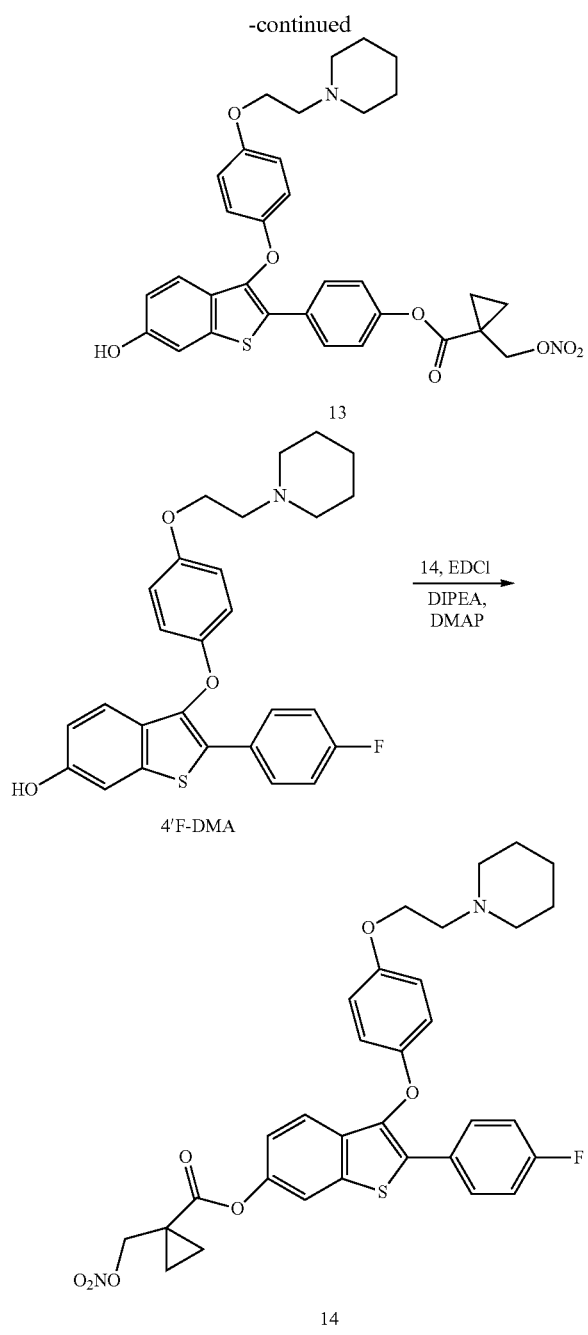

Compound 9.

4'Br-DMA (75 mg, 0.14 mmol) was dissolved in a mixture THF (4 mL) and DIPEA (347 µL, 2.1 mmol), MOM-Br (16 µL, 0.17 mmol) was added. The reaction mixture was refluxed for 5 hrs. Most of the solvent was removed under reduced pressure. The residue was dissolved in DCM and washed with aqueous NaHCO$_3$ and brine. Organic phase separated and concentrated. The residue was purified by column chromatography (DCM/MeOH 20:1), product was obtained as oil (55 mg, 68%). $^1$H-NMR (Acetone-d$_6$, 400 MHz): δ 7.70 (d, 2H, J=8.8 Hz), 7.58 (d, 1H, J=2.0 Hz), 7.55 (d, 2H, J=8.4 Hz), 7.30 (d, 1H, J=8.8 Hz), 7.02 (dd, 1H, J=8.8 Hz, 2.0 Hz), 6.83-6.90 (m, 4H), 5.26 (s, 2H), 3.99 (t, 2H, J=6.0 Hz), 3.45 (s, 3H), 2.64 (t, 2H), 2.44 (broad peak, 4H), 1.48-1.54 (m, 4H), 1.38-1.41 (m, 2H); $^{13}$C-NMR (Acetone-d$_6$, 100 MHz): 155.89, 155.43, 152.08, 142.33, 137.78, 132.76, 132.33, 129.76, 129.33, 126.21, 123.20, 122.08, 117.12, 116.79, 116.37, 109.73, 95.35, 67.25, 58.60, 56.16, 55.59, 26.70, 24.93.

Compound 10.

A round bottom flask was charged with compound 9 (50 mg, 0.088 mmol), Pd$_2$dba$_3$ (4.1 mg, 5 mol %), KOH (20.1 mg, 4 equiv.), ligand 2-Di-tert-butylphosphino-2',4',6'-triisopropylbiphenyl (4.2 mg, 10% mol) and filled with argon. A mixture of 1,4-dioxane (2 mL) and H$_2$O (1 mL) was added. The reaction was stirred at 80° C. for 6 hrs. Most of the solvent was removed and directly purified by column chromatography (DCM/MeOH 50:3 with 0.1% acetic acid), product was obtained as acid salt (45 mg, 90%). $^1$H-NMR (Acetone-d$_6$, 400 MHz): δ 7.60 (d, 2H, J=8.8 Hz), 7.56 (d, 1H, J=2.0 Hz), 7.26 (d, 1H, J=8.8 Hz), 7.01 (dd, 1H, J=2.0 Hz, 8.8 Hz), 6.83-6.89 (m, 6H), 5.26 (s, 2H), 4.18 (t, 2H, J=5.6 Hz), 3.45 (s, 3H), 3.02 (t, 2H, J=5.6 Hz), 2.84 (broad peak, 4H), 1.94 (s, 3H), 1.65-1.70 (m, 4H), 1.48-1.50 (m, 2H); $^{13}$C-NMR (Acetone-d$_6$, 100 MHz): 172.86, 158.54, 156.36, 154.66, 152.66, 140.08, 137.09, 129.79, 129.55, 128.31, 124.24, 122.52, 117.02, 116.64, 116.47, 116.43, 109.84, 95.42, 65.64, 57.54, 56.10, 54.79, 25.18, 23.77, 20.96.

Compound 12.

Compound 10 (40 mg, 0.07 mmol) was dissolved in DCM (20 mL) and washed with saturated NaHCO$_3$ (2×10 mL), organic phase was separated, concentrated and dried under high vacuum for 1 hr. The residue was dissolved in DCM (2 mL), DIPEA (116 µL, 0.7 mmol), DMAP (8.5 mg, 0.07 mmol), compound 11 (16.9 mg, 0.1 mmol) and EDCI (27 mg, 0.14 mmol) were added successively. The reaction mixture was stirred at r.t. for 3 hrs, diluted with DCM (20 mL), washed with aqueous NaHCO$_3$ (10 mL) and H$_2$O (10 mL), organic phase separated and concentrated. The residue was purified by column chromatography (ethyl acetate/MeOH 30:1), product was obtained as slightly yellow oil (30 mg, 65%). $^1$H-NMR (Acetone-d$_6$, 400 MHz): δ 7.81-7.83 (m, 2H), 7.60 (d, 1H, J=2.0 Hz), 7.31 (d, 1H, J=8.8 Hz), 7.18-7.21 (m, 2H), 7.03 (dd, 1H, J=8.8 Hz, 2.0 Hz), 6.84-6.92 (m, 4H), 5.27 (s, 2H), 4.86 (s, 2H), 4.00 (t, 2H, J=6.0 Hz), 3.46 (s, 3H), 2.65 (t, 2H, J=6.0 Hz), 2.45 (broad peak, 4H), 1.58-1.61 (m, 2H), 1.49-1.54 (m, 4H), 1.35-1.40 (m, 4H); $^{13}$C-NMR (Acetone-d$_6$, 100 MHz): 171.46, 156.82, 155.43, 152.23, 151.15, 141.89, 137.74, 130.92, 129.45, 129.12, 126.70, 123.10, 123.01, 117.10, 116.75, 116.38, 109.78, 95.39, 76.53, 67.31, 58.66, 56.15, 55.65, 26.76, 24.98, 22.35, 15.36.

Compound 13.

Compound 12 (30 mg, 0.046 mmol) was dissolved in a mixture of DCM (2 mL) and EtOH (0.5 mL), TsOH.H$_2$O (20 mg, 0.11 mmol) was added. The reaction mixture was stirred at 40° C. until all the starting material was consumed. After dilution with DCM (25 mL) and washed with saturated NaHCO$_3$ (2×5 mL), organic phase was separated and concentrated. The residue was purified by column chromatography (DCM/MeOH 25:2), product was obtained as slightly yellow foam (16 mg, 58%). $^1$H-NMR (THF-d$_8$, 400 MHz): δ 7.43 (d, 2H, J=8.8 Hz), 7.15-7.17 (m, 2H), 7.08 (d, 2H, J=8.8 Hz), 6.85 (d, 2H, J=9.2 Hz), 6.78 (d, 2H, J=9.2 Hz), 6.73 (dd, 1H, J=2.0 Hz, 8.8 Hz), 4.76 (s, 2H), 4.00 (t, 2H, J=6.0 Hz), 2.70 (t, 2H, J=6.0 Hz), 2.51 (broad peak, 4H), 1.51-1.59 (m, 6H), 1.38-1.43 (m, 4H); $^{13}$C-NMR (THF-d$_8$, 100 MHz): 171.04, 157.50, 155.36, 152.52, 150.98, 142.16, 138.22, 131.34, 128.83, 127.76, 125.04, 123.19, 122.62, 117.02, 116.21, 115.57, 108.61, 76.32, 68.22, 58.68, 55.76, 26.72, 24.92, 22.44, 15.19.

Compound 14.

4'FDMA (155 mg, 0.33 mmol), DIPEA (330 µL, 2.0 mmol), DMAP (30 mg, 0.25 mmol), compound 14 (82 mg, 0.51 mmol) were dissolved in DCM (5 mL), EDCI (134 mg, 0.7 mmol) was added to this solution. The reaction was stirred at r.t. overnight. Reaction mixture was diluted with ethyl acetate (50 mL), washed with water and concentrated, the residue was purified by column chromatography (DCM/MeOH 25:1), product was obtained as white foam (151 mg, 74%). $^1$H-NMR (Acetone-d$_6$, 400 MHz): δ 7.82-7.85 (m, 2H), 7.78 (d, 1H, J=1.6 Hz), 7.41 (d, 1H, J=8.8 Hz), 7.18-7.23 (m, 2H), 7.13 (dd, 1H, J=8.4 Hz, 2.0 Hz), 6.85-6.92 (m, 4H), 4.89 (s, 2H), 4.03 (t, 2H, J=6.0 Hz), 2.69 (t, 2H, J=6.0 Hz), 2.49 (broad peak, 4H), 1.62-1.65 (m, 2H), 1.50-1.55 (m, 4H), 1.38-1.41 (m, 4H); $^{13}$C-NMR (Acetone-d$_6$, 100 MHz): δ 171.73, 164.54, 162.09, 155.46, 152.17, 149.59, 141.51, 136.81, 132.65, (130.51, 130.43), (129.19, 129.16), 122.88, 120.38, 117.11, 116.83, 116.61, 116.46, 76.54, 67.16, 58.53, 55.56, 26.59, 24.84, 22.40, 15.43.

Example 13

Pharmacokinetics of SEMs in Mice

SEM prodrugs have been prepared using standard, scalable organic chemistry techniques. SEMs with antithrombotic properties will be prepared using the strategy described above for NO-SERMs (e.g., compounds 8, 13, and 14). Metabolic stability will be verified in human liver and human intestinal microsomal incubations, and plasma, with or without esterase (PLE). SEMs with high stability, minimal oxidative metabolites, and efficient enzymic bioactivation to TTC-352 [i.e., 3-(4-fluorophenyl)-2-(4-hydroxyphenoxy)benzo[b]thiophen-6-ol] will be advanced to pharmacokinetic studies.

Ovariectomized (OVX) nude 4- to 6-week-old athymic mice will be administered TTC-352 and no more than 3 SEM prodrugs and/or NO-SEMs by gavage in ethanol using a vehicle of propylene glycol/carboxymethyl cellulose at a single dose of 4.4 µmol (equivalent to 1.5 mg/day used in xenograft studies). Blood samples will be collected at 20 min, 2 h, and 6 h after treatment, using EDTA as an anticoagulant. Plasma will be separated from whole blood by centrifugation at 4° C. and samples will be immediately analyzed for prodrug and drug using LC-MS/MS.

Example 14

Efficacy of SEM Prodrugs and NO-SEMs on TAM-Resistant Xenograft Tumor Growth

T47D-Tam1 and T47D/PKCα xenograft tumor models will be used to assess the efficacy of 2 SEM treatments at 2 doses (4.4 µmol and 0.44 µmol/day, based upon data shown in FIG. 11). Tumors will be grown in OVX athymic mice and treated once tumor volume reaches approximately 0.5 cm$^2$. The response to SEMs and/or NO-SEMs will be compared to the standard of care (e.g., tamoxifen).

Example 15

Mechanism of Action Confirmation

For tumors treated by SEMs and/or NO-SEMs, PKCα, and ER biomarkers will be assessed by immunohistochemistry. Anticoagulant activity will be measured ex vivo.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

Example 16

Synthesis of a Compound of Formula (I)

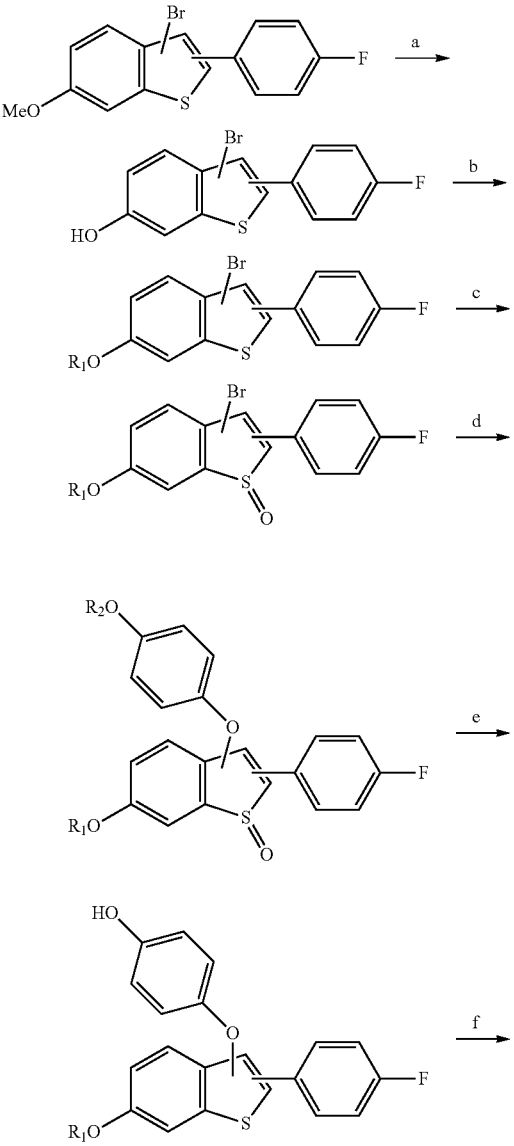

Scheme 1

61
-continued

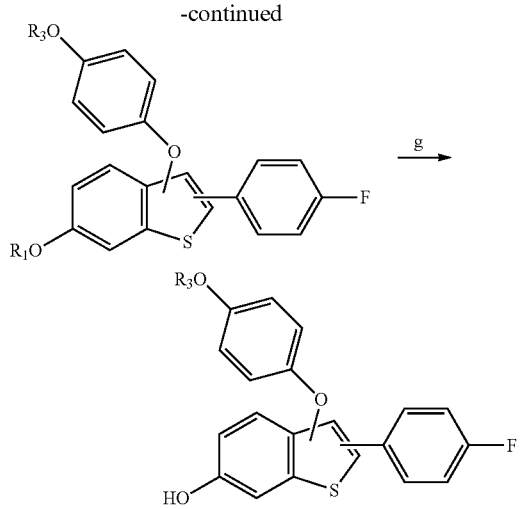

R₁ = TBDPS, TBDMS, TMS, benzyl
R₂ = TBDPS, TBDMS, TMS, benzyl

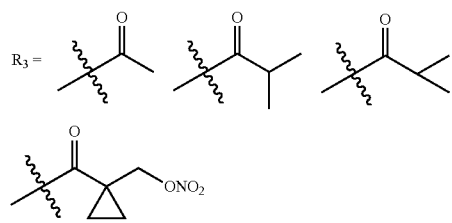

Reagents and conditions: (a) BBr₃, DCM, 0° C.; (b) TBDPSCl, Im, DMF; (c) H₂O₂, TFA, DCM; (d) 4-benzoxyphenol, NaH, DMF; (e) i), LiAlH₄, THF, 0° C.; ii), Pd/C, H₂, MeOH; (f) 1-((nitrooxy)methyl)cyclopropanecarboxylic acid, DIPEA, DMAP, EDCl, DCM; (g) Bu₄NF, THF

62
-continued

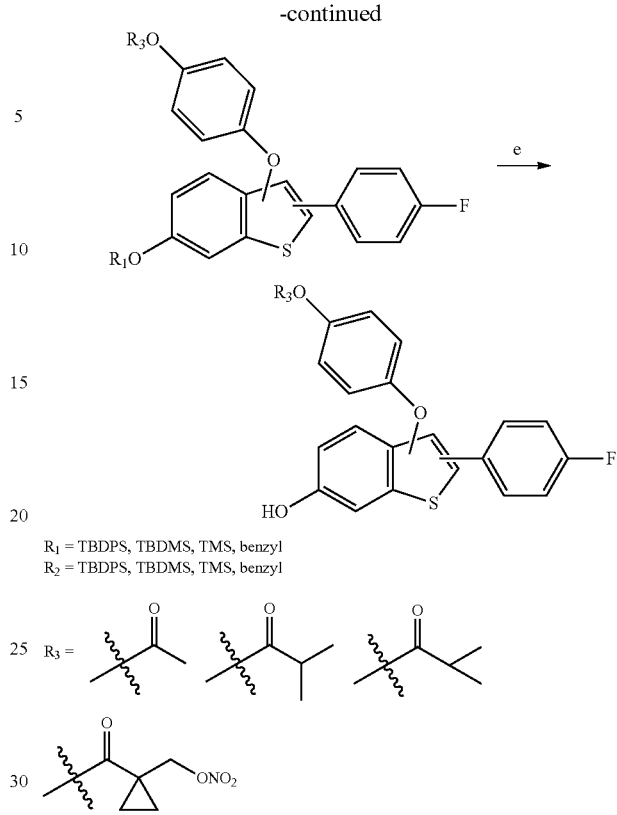

R₁ = TBDPS, TBDMS, TMS, benzyl
R₂ = TBDPS, TBDMS, TMS, benzyl

Reagents and conditions: (a) n-BuLi, THF, B(OMe)₃ (b) 4-(benzoxy)phenol, Cu(OAC)₂, pyridine, DCM; (c) Pd/C, H₂, MeOH; (d) 1-((nitrooxy)methyl) cyclopropanecarboxylic acid, DIPEA, DMAP, EDCl, DCM; (e) Bu₄NF, THF

Scheme 2

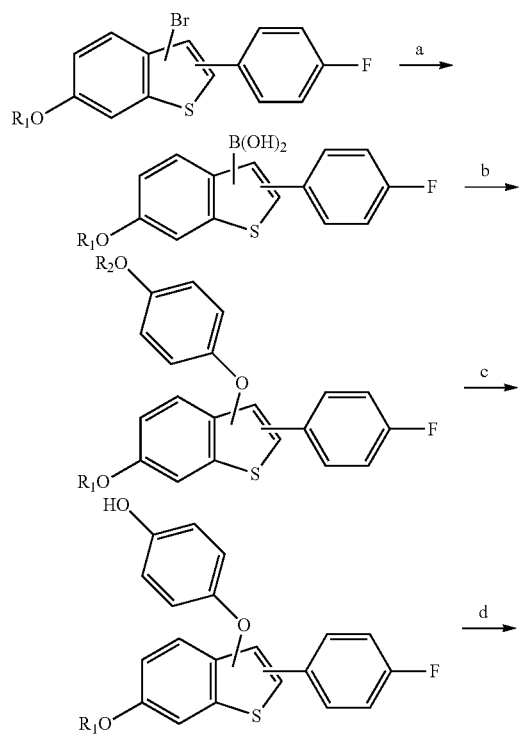

Scheme 3

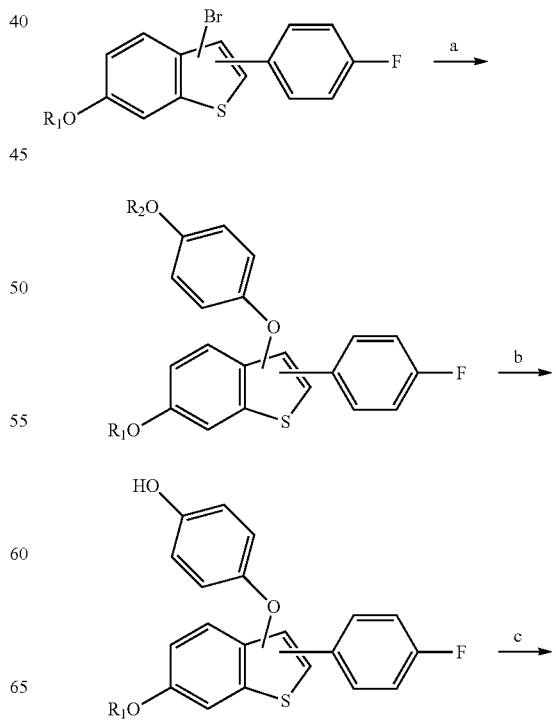

63

-continued

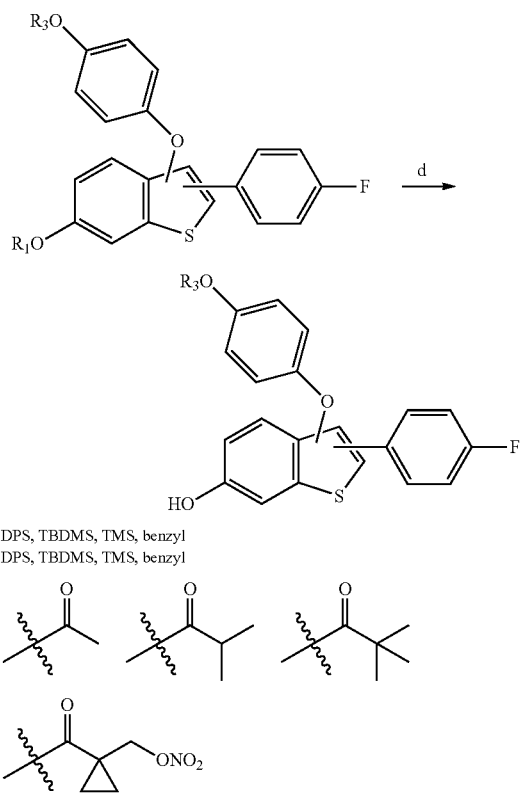

$R_1$ = TBDPS, TBDMS, TMS, benzyl
$R_2$ = TBDPS, TBDMS, TMS, benzyl
$R_3$ =

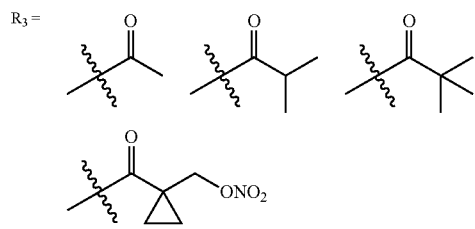

Reagents and conditions: (a) Cu$_2$O, Collidine, 4-benzoxyphenol; (b) Pd/C, H$_2$, MeOH; (c) 1-((nitrooxy)methyl)cyclopropanecarboxylic acid, DIPEA, DMAP, EDCl, DCM; (d) Bu$_4$NF, THF A compound of formula (I), wherein $A_1$ is halogen, $A_2$ is —$OR_2$, $R_2$ is hydrogen, $X_1$ is —O—, $A_3$ is aryl, and $A_4$ is —$OR_3$, wherein $R_3$ is described above, may be prepared according to the methods illustrated in Scheme 1, 2 or 3.

Scheme 4

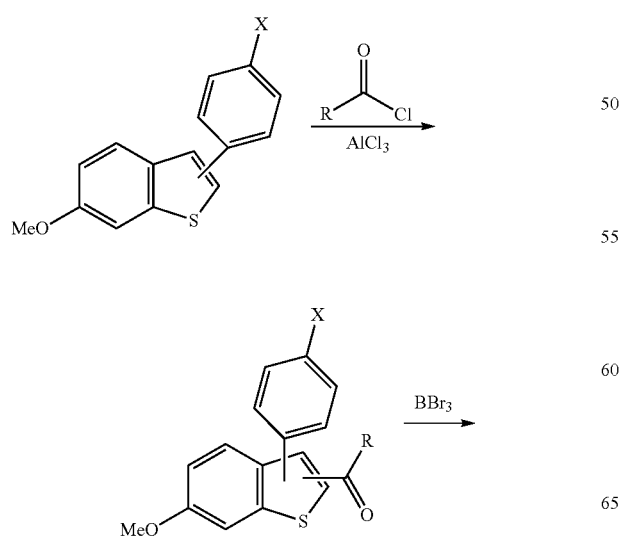

64

-continued

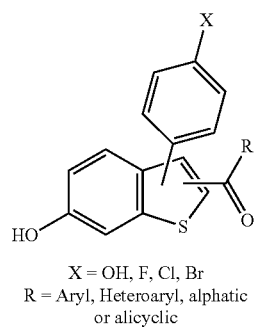

X = OH, F, Cl, Br
R = Aryl, Heteroaryl, alphatic or alicyclic

Scheme 5

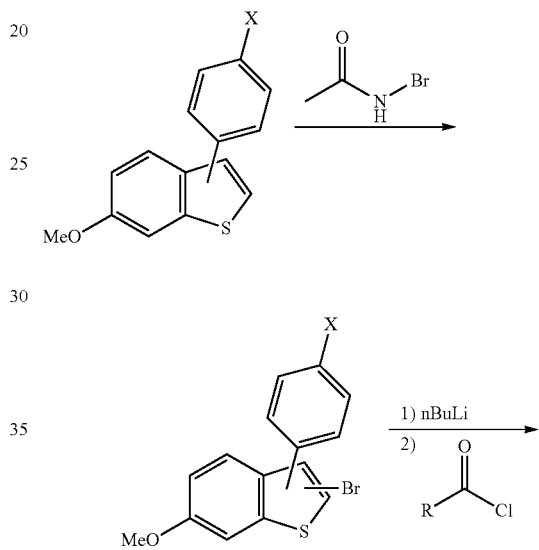

X = OH, F, Cl, Br
R = Aryl, Heteroaryl, alphatic or alicyclic

Scheme 6
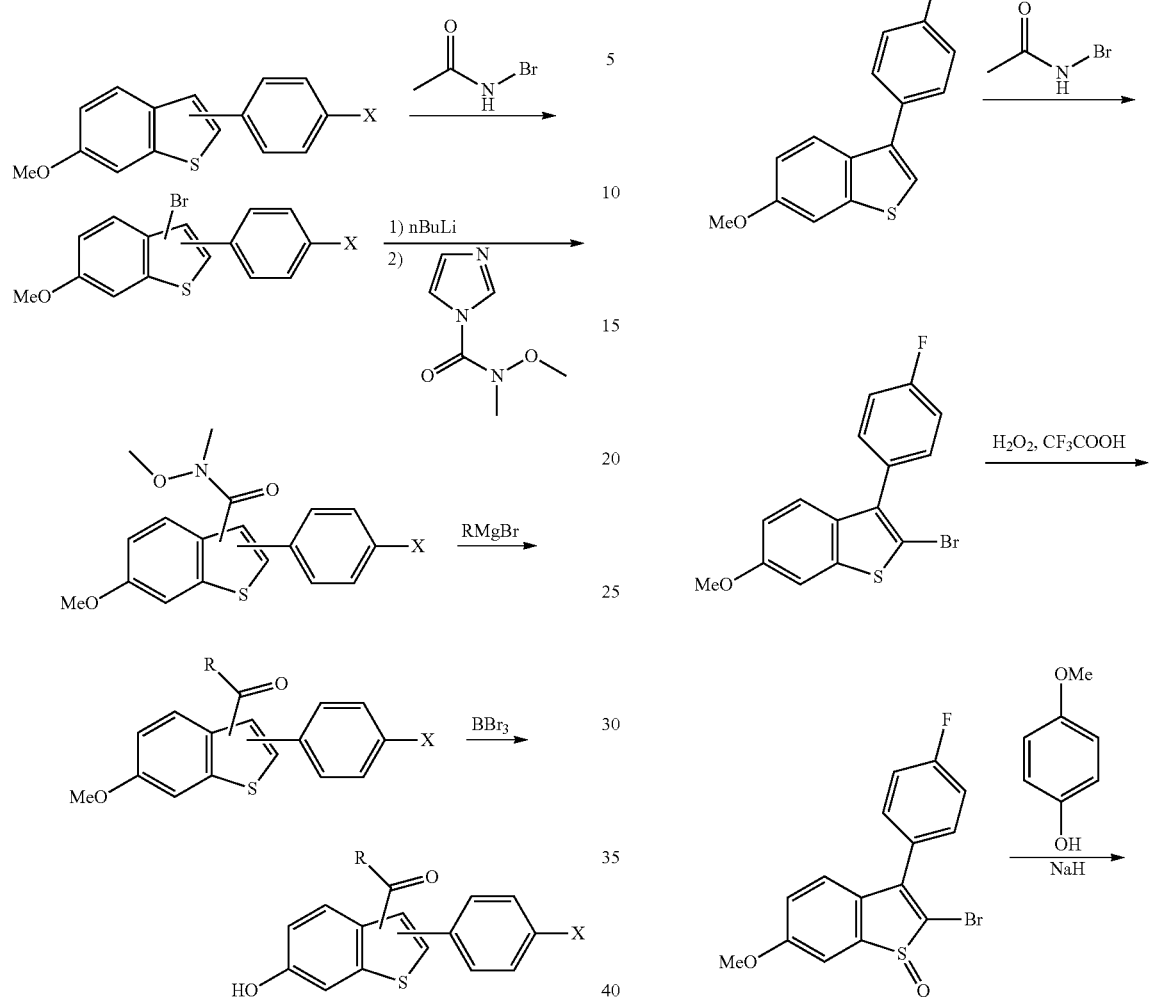
X = OH, F, Cl, Br
R = Aryl, Heteroaryl, aliphatic or alicyclic
A compound of formula (Ic) or formula (II) may be prepared according to the methods illustrated in Scheme 4, 5, or 6.
Scheme 7
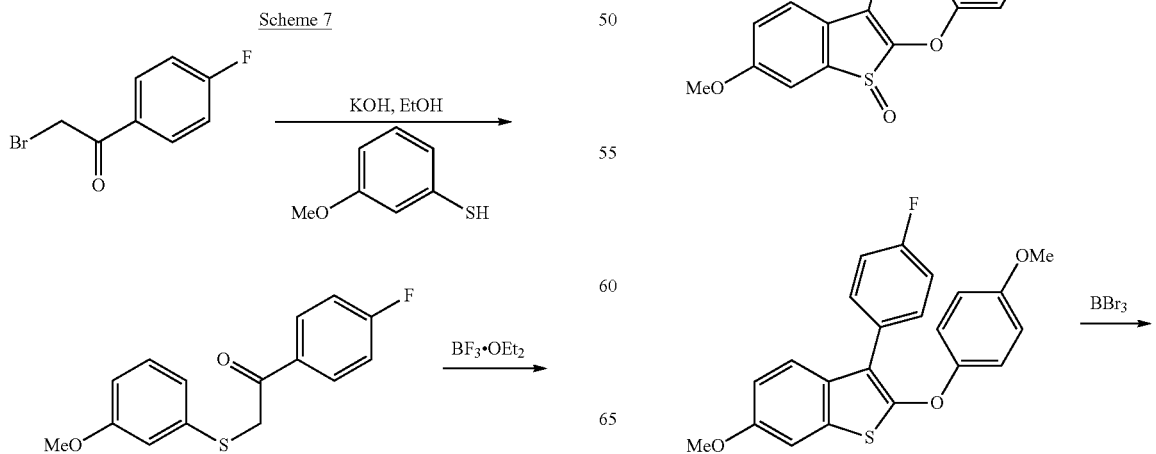

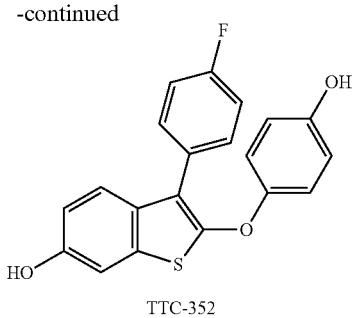

TTC-352

The compound 3-(4-fluorophenyl)-2-(4-hydroxyphenoxy)benzo[b]thiophen-6-ol (TTC-352) can be prepared as described above in Scheme 7 and the following examples.

1-(4-Fluorophenyl)-2-(3-methoxyphenylsulfanyl)ethanone

3-Methoxybenzenethiol (1 g, 7.1 mmol) was added in one portion to a freshly prepared solution of 7.5 mL of ethanol, 3 mL of water, and 470 mg of KOH (8.4 mmol). The solution was cooled to 5-10° C. A solution of 2-bromo-1-(4-fluorophenyl)ethanone (1.54 g, 7.1 mmol) in 2.5 mL of EtOAc was added to this solution at a rate such that the temperature did not exceed 25° C., and the reaction mixture was allowed to stir overnight at room temperature. The solvents were removed under reduced pressure, and the residue was partitioned between water and ethyl acetate. The aqueous layer was isolated and extracted several times with ethyl acetate, and the combined extracts were washed with consecutive portions of 10% HCl, water, saturated NaHCO3, and water before being dried over anhydrous Na2SO4. After concentration in vacuo to an oil, the crude product was purified by flash chromatography [SiO2, hexane/ethyl acetate (10:1, v/v)] to give 1.4 g (74%) desired product. 1H NMR (300 MHz, DMSO-d6) δ 3.73 (s, 3H), 4.67 (s, 3H), 6.75 (m, 1H), 6.91 (m, 2H), 7.18 (t, J) 8.2 Hz, 1H), 7.34 (t, J) 8.9 Hz, 2H), 8.12 (q, J) 8.9 Hz, 2H).

3-(4-fluorophenyl)-6-methoxybenzo[b]thiophene

A flask was charged with 1-(4-Fluorophenyl)-2-(3-methoxyphenylsulfanyl)ethanone and BF3.OEt2 under Argon atmosphere at room temperature. The reaction mixture was stirred until starting material was consumed as monitored by TLC. The reaction mixture was poured into saturated NaHCO3/ice water, stirred 30 min, and extracted with dichloromethane. The crude product was purified by flash chromatography [SiO2, hexane/dichloromethane (20:1, v/v)]. The combined fractions from column was recrystalized to get 50% pure product. 1H NMR (400 MHz, CDCl3) δ (ppm) 3.89 (s, 3H), 7.02 (dd, 8.9 Hz, 2.2 Hz 1H), 7.15 (m, 3H), 7.37 (d, 2.2 Hz 1H), 7.52 (m, 2H), 7.71 (d, 8.9 Hz, 1H), 13C NMR (100 MHz, CDCl3) δ (ppm) 55.62, 105.24, 114.52, 115.50, 115.71, 120.67, 123.30, 130.09, 130.17, 131.96, 132.17, 136.62, 142.07, 157.56, 162.31.

2-bromo-3-(4-fluorophenyl)-6-methoxybenzo[b]thiophene

N-Bromoacetamide (1.46 g, 10.5 mmol) in 10 mL of ethanol was added dropwise to a solution of 3-(4-fluorophenyl)-6-methoxybenzo[b]thiophene (2.58 g, 10 mmol) in 300 mL of CH2Cl2 and 20 mL of ethanol at room temperature. After the mixture was stirred for 1 h, the solvent was removed in vacuo. Next, the residue was titrated with ethanol and filtered to give 3.0 g (89%) of desired product. 1H NMR (400 MHz, CDCl3) δ (ppm) 3.898 (s, 3H), 6.94 (dd, 8.9 Hz, 2.3 Hz 1H), 7.24 (m, 3H), 7.38 (d, 8.9 Hz 1H), 7.45 (m, 2H)), 13C NMR (100 MHz, CDCl3) δ (ppm) 55.27, 104.1, 109.47, 114.20, 115.14, 115.36, 122.99, 129.57, 131.23, 131.31, 132.29, 135.28, 140.61, 157.36, 162.05.

2-bromo-3-(4-fluorophenyl)-6-methoxybenzo[b]thiophene 1-oxide

Trifluoacetic acid (13 mL) was added dropwise to a solution of 2-bromo-3-(4-fluorophenyl)-6-methoxybenzo[b]thiophene (2.4 g, 7 mmol) in 13 mL of anhydrous CH2Cl2. After the mixture was stirred for 5 min, H2O2 (1.0 mL, 7 mmol, 30% aqueous solution) was added dropwise, and the resulting mixture was stirred for 2 h at room temperature. Sodium bisulfite (0.3 g) was added to the solution followed by 5 mL of water. The mixture was stirred vigorously for 30 min and then concentrated in vacuo. The residue was partitioned between CH2Cl2 and saturated aqueous NaHCO3 solution (50 mL each). The layers were separated, and the organic layer was washed with consecutive portions of water, saturated NaHCO3, and water, and then dried over anhydrous Na2SO4 and concentrated in vacuo; the residue was titrated with diethylether and filtered to give 2.1 g (84%) of desired product.

3-(4-fluorophenyl)-6-methoxy-2-(4-methoxyphenoxy)benzo[b]thiophene 1-oxide

NaH (237 mg, 9.9 mmol, 60% dispersion in mineral oil) was added to a solution of 4-methoxyphenol (1.31 g, 59 mmol) in 25 mL of anhydrous DMF at room temperature. After the mixture was stirred for 15 min, 2-bromo-3-(4-fluorophenyl)-6-methoxybenzo[b]thiophene 1-oxide (2 g, 5.7 mmol) was added in small portions. After the mixture was stirred for 1 h, ethyl acetate and water were added, and the organic layer was washed several times with water and then dried over Na2SO4. The residue was titrated with hexane/ethyl acetate (10:1, v/v) and filtered to yield 2.47 g (89%) of desired product.

3-(4-fluorophenyl)-6-methoxy-2-(4-methoxyphenoxy)benzo[b]thiophene

LiAlH4 (0.27 g, 7.2 mmol) was added in small portions to a solution of 3-(4-fluorophenyl)-6-methoxy-2-(4-methoxyphenoxy)benzo[b]thiophene 1-oxide (2.37 g, 4.8 mmol) in 180 mL of anhydrous THF under argon at 0° C. After the mixture was stirred for 30 min, the reaction was quenched by the slow addition of 4 mL of 2.0 MNaOH. The mixture was stirred vigorously for 30 min, and a minimal amount of 2.0 M NaOH was added to dissolve salts. The mixture was then partitioned between water and ethanol/ethyl acetate (1:9, v/v). The aqueous layer was isolated and then extracted several times with ethanol/ethyl acetate (1:9, v/v). The organic layers were combined, dried over anhydrous Na2SO4, concentrated in vacuo to an oil, and then purified by flash chromatography to give 1.2 g (67%) of desired product.

3-(4-fluorophenyl)-2-(4-hydroxyphenoxy)benzo[b]thiophen-6-ol (TTC-352)

3-(4-fluorophenyl)-6-methoxy-2-(4-methoxyphenoxy)benzo[b]thiophene (1.5 g, 2.9 mmol) was dissolved in 150 mL of anhydrous CH2Cl2 and cooled to 0° C. BBr$_3$ (1.0 M in CH2Cl2, 11.6 mL, 11.6 mmol) was added to this solution followed by stirring at 0° C. for 4 h. The reaction was quenched by saturated NaHCO3 (100 mL) and cooled to 0° C. The aqueous layer was isolated and extracted with methanol/ethyl acetate (5:95, v/v) (3_100 mL). The organic extracts were combined, dried over anhydrous Na2SO4, concentrated in vacuo, and then purified by flash chromatography [SiO2, CH2Cl2/MeOH (8:1, v/v)] to obtain 1.1 g (75%) desired product. $^1$H NMR (400 MHz, acetone d6) δ (ppm) 6.84 (m, 2H), 6.97 (dd, 8.9 Hz, 2.2 Hz, 1H), 7.02 (m, 2H), 7.24 (m, 2H)), 7.28 (d, 2.2 Hz, 1H), 7.47 (d, 8.9 Hz, 1H), 7.61 (m, 2H)$^{13}$C NMR (100 MHz acetone d6) δ (ppm) 162.84, 155.94, 155.02, 153.81, 152.35, 135.21, 132.28, 132.20, 130.90, 130.32, 123.70, 120.81, 119.67, 119.66, 116.95, 116.95, 116.39, 116.17, 115.52, 109.00.

4-((3-(4-fluorophenyl)-6-methoxybenzo[b]thiophen-2-yl)oxy)phenol (Monomethoxyl-TTC-352)

Made from general procedure as TTC-352. $^1$H NMR (400 MHz, Acetone d6) δ=7.62 (m, 2H), 7.52 (d, 8.9 Hz, 1H), 7.41 (d, 2.3 Hz, 1H), 7.25 (t, 8.9 Hz, 2H), 7.02 (dd, 9.0 Hz, 2.6, 3H), 6.83 (d, 9.0 Hz, 2H), 3.86 (s, 3H). $^{13}$C NMR (100 MHz acetone d6) δ (ppm) 161.95, 157.52, 154.09, 153.58, 151.34, 134.15, 131.34, 131.26, 130.71, 129.25, 122.60, 119.70, 118.79, 118.79, 116.00, 115.91, 115.46, 115.24, 114.20, 105.89, 55.04.

7. REFERENCES

1. R. Antonicelli, F. Olivieri, V. Morichi, E. Urbani, V. Mais, Prevention of cardiovascular events in early menopause: a possible role for hormone replacement therapy. *Int J Cardiol* 130, 140 (Nov. 12, 2008).
2. R. T. Turner, B. L. Riggs, T. C. Spelsberg, Skeletal effects of estrogen. *Endocr Rev* 15, 275 (June, 1994).
3. F. Ba, P. K. Pang, S. T. Davidge, C. G. Benishin, The neuroprotective effects of estrogen in SK—N—SH neuroblastoma cell cultures. *Neurochem Int* 44, 401 (May, 2004).
4. L. Fan, S. C. Pandey, R. S. Cohen, Estrogen affects levels of Bcl-2 protein and mRNA in medial amygdala of ovariectomized rats. *J Neurosci Res* 86, 3655 (December, 2008).
5. P. Tanapat, N. B. Hastings, A. J. Reeves, E. Gould, Estrogen stimulates a transient increase in the number of new neurons in the dentate gyrus of the adult female rat. *J Neurosci* 19, 5792 (Jul. 15, 1999).
6. L. A. Galea, M. D. Spritzer, J. M. Barker, J. L. Pawluski, Gonadal hormone modulation of hippocampal neurogenesis in the adult. *Hippocampus* 16, 225 (2006).
7. L. A. Galea, Gonadal hormone modulation of neurogenesis in the dentate gyrus of adult male and female rodents. *Brain Res Rev* 57, 332 (March, 2008).
8. S. M. Resnick, P. M. Maki, S. Golski, M. A. Kraut, A. B. Zonderman, Effects of estrogen replacement therapy on PET cerebral blood flow and neuropsychological performance. *Horm Behav* 34, 171 (October, 1998).
9. P. M. Maki, S. M. Resnick, Longitudinal effects of estrogen replacement therapy on PET cerebral blood flow and cognition. *Neurobiol Aging* 21, 373 (March-April, 2000).
10. D. J. Wegesin, Y. Stern, Effects of hormone replacement therapy and aging on cognition: evidence for executive dysfunction. *Neuropsychol Dev Cogn B Aging Neuropsychol Cogn* 14, 301 (May, 2007).
11. J. E. Rossouw et al., Risks and benefits of estrogen plus progestin in healthy postmenopausal women: principal results From the Women's Health Initiative randomized controlled trial. *JAMA* 288, 321 (Jul. 17, 2002).
12. S. A. Shumaker et al., The Women's Health Initiative Memory Study (WHIMS): a trial of the effect of estrogen therapy in preventing and slowing the progression of dementia. *Control Clin Trials* 19, 604 (December, 1998).
13. E. S. LeBlanc, J. Janowsky, B. K. Chan, H. D. Nelson, Hormone replacement therapy and cognition: systematic review and meta-analysis. *JAMA* 285, 1489 (Mar. 21, 2001).
14. K. Yaffe, G. Sawaya, I. Lieberburg, D. Grady, Estrogen therapy in postmenopausal women: effects on cognitive function and dementia. *JAMA* 279, 688 (Mar. 4, 1998).
15. R. B. Gibbs, Estrogen therapy and cognition: a review of the cholinergic hypothesis. *Endocr Rev* 31, 224 (April, 2010).
16. P. M. Maki, E. Sundermann, Hormone therapy and cognitive function. *Hum Reprod Update* 15, 667 (November-December, 2009).
17. P. D. Delmas et al., Effects of raloxifene on bone mineral density, serum cholesterol concentrations, and uterine endometrium in postmenopausal women. *N Engl J Med* 337, 1641 (Dec. 4, 1997).
18. D. Agnusdei, N. Iori, Raloxifene: results from the MORE study. *J Musculoskelet Neuronal Interact* 1, 127 (December, 2000).
19. E. Siris et al., Effects of raloxifene on fracture severity in postmenopausal women with osteoporosis: results from the MORE study. Multiple Outcomes of Raloxifene Evaluation. *Osteoporos Int* 13, 907 (November, 2002).
20. V. G. Vogel et al., Effects of tamoxifen vs raloxifene on the risk of developing invasive breast cancer and other disease outcomes: the NSABP Study of Tamoxifen and Raloxifene (STAR) P-2 trial. *JAMA* 295, 2727 (Jun. 21, 2006).
21. F. J. Cohen, S. Watts, A. Shah, R. Akers, L. Plouffe, Jr., Uterine effects of 3-year raloxifene therapy in postmenopausal women younger than age 60. *Obstet Gynecol* 95, 104 (January, 2000).
22. K. Yaffe et al., Effect of raloxifene on prevention of dementia and cognitive impairment in older women: the Multiple Outcomes of Raloxifene Evaluation (MORE) randomized trial. *Am J Psychiatry* 162, 683 (April, 2005).
23. E. Barrett-Connor et al., Effects of raloxifene on cardiovascular events and breast cancer in postmenopausal women. *N Engl J Med* 355, 125 (Jul. 13, 2006).
24. A. Saitta et al., Randomized, double-blind, placebo-controlled study on effects of raloxifene and hormone replacement therapy on plasma no concentrations, endothelin-1 levels, and endothelium-dependent vasodilation in postmenopausal women. *Arterioscler Thromb Vasc Biol* 21, 1512 (September, 2001).
25. M. H. Wyckoff et al., Plasma membrane estrogen receptors are coupled to endothelial nitric-oxide synthase through Galpha(i). *J Biol Chem* 276, 27071 (Jul. 20, 2001).
26. T. Simoncini, A. R. Genazzani, J. K. Liao, Nongenomic mechanisms of endothelial nitric oxide synthase activation by the selective estrogen receptor modulator raloxifene. *Circulation* 105, 1368 (Mar. 19, 2002).
27. O. Khorram, M. Garthwaite, R. R. Magness, Endometrial and myometrial expression of nitric oxide synthase isoforms in pre- and postmenopausal women. *J Clin Endocrinol Metab* 84, 2226 (June, 1999).

28. E. Gkaliagkousi, A. Ferro, Nitric oxide signalling in the regulation of cardiovascular and platelet function. *Front Biosci* 16, 1873 (2011).
29. A. R. Smith, F. Visioli, B. Frei, T. M. Hagen, Age-related changes in endothelial nitric oxide synthase phosphorylation and nitric oxide dependent vasodilation: evidence for a novel mechanism involving sphingomyelinase and ceramide-activated phosphatase 2A. *Aging Cell* 5, 391 (October, 2006).
30. B. Jeynes, J. Provias, Significant negative correlations between capillary expressed eNOS and Alzheimer lesion burden. *Neurosci Lett* 463, 244 (Oct. 9, 2009).
31. P. M. Maki, Hormone therapy and cognitive function: is there a critical period for benefit? *Neuroscience* 138, 1027 (2006).
32. B. B. Sherwin, Estrogen therapy: is time of initiation critical for neuroprotection? *Nat Rev Endocrinol* 5, 620 (November, 2009).
33. W. A. Rocca, B. R. Grossardt, L. T. Shuster, Oophorectomy, menopause, estrogen, and cognitive aging: the timing hypothesis. *Neurodegener Dis* 7, 163 (2010).
34. R. B. Gibbs, Long-term treatment with estrogen and progesterone enhances acquisition of a spatial memory task by ovariectomized aged rats. *Neurobiol Aging* 21, 107 (January-February, 2000).
35. R. D. Brinton, The healthy cell bias of estrogen action: mitochondrial bioenergetics and neurological implications. *Trends Neurosci* 31, 529 (October, 2008).
36. Q. G. Zhang et al., C terminus of Hsc70-interacting protein (CHIP)-mediated degradation of hippocampal estrogen receptor-alpha and the critical period hypothesis of estrogen neuroprotection. *Proc Natl Acad Sci USA* 108, E617 (Aug. 30, 2011).
37. C. Stirone, A. Boroujerdi, S. P. Duckles, D. N. Krause, Estrogen receptor activation of phosphoinositide-3 kinase, akt, and nitric oxide signaling in cerebral blood vessels: rapid and long-term effects. *Mol Pharmacol* 67, 105 (January, 2005).
38. R. A. Hopper, J. Garthwaite, Tonic and phasic nitric oxide signals in hippocampal long-term potentiation. *J Neurosci* 26, 11513 (Nov. 8, 2006).
39. G. Garthwaite et al., Signaling from blood vessels to CNS axons through nitric oxide. *J Neurosci* 26, 7730 (Jul. 19, 2006).
40. C. Grohe et al., 17 Beta-estradiol regulates nNOS and eNOS activity in the hippocampus. *Neuroreport* 15, 89 (Jan. 19, 2004).
41. N. Suh et al., Arzoxifene, a new selective estrogen receptor modulator for chemoprevention of experimental breast cancer. *Cancer Res* 61, 8412 (Dec. 1, 2001).
42. M. Sato et al., LY353381.HCl: a novel raloxifene analog with improved SERM potency and efficacy in vivo. *J Pharmacol Exp Ther* 287, 1 (October, 1998).
43. D. Hochner-Celnikier, Pharmacokinetics of raloxifene and its clinical application. *Eur J Obstet Gynecol Reprod Biol* 85, 23 (July, 1999).
44. A. D. Palkowitz et al., Discovery and synthesis of [6-hydroxy-3-[4-[2-(1-piperidinyl)ethoxy]phenoxy]-2-(4-hydroxyphenyl)]benzo[b]thiophene: a novel, highly potent, selective estrogen receptor modulator. *J Med Chem* 40, 1407 (May 9, 1997).
45. C. R. Overk et al., Structure-activity relationships for a family of benzothiophene selective estrogen receptor modulators including raloxifene and arzoxifene. *Chem Med Chem* 2, 1520 (October, 2007).
46. G. R. Thatcher, B. M. Bennett, J. N. Reynolds, NO chimeras as therapeutic agents in Alzheimer's disease. *Curr Alzheimer Res* 3, 237 (July, 2006).
47. G. R. Thatcher, B. M. Bennett, J. N. Reynolds, Nitric oxide mimetic molecules as therapeutic agents in Alzheimer's disease. *Curr Alzheimer Res* 2, 171 (April, 2005).
48. S. Smith, H. C. Dringenberg, B. M. Bennett, G. R. J. Thatcher, J. N. Reynolds, A novel nitrate ester reverses the cognitive impairment caused by scopolamine in the Morris water maze. *Neuroreport* 11, 3883 (2000).
49. B. M. Bennett et al., Cognitive deficits in rats after forebrain cholinergic depletion are reversed by a novel NO mimetic nitrate ester. *Neuropsychopharmacology* 32, 505 (March, 2007).
50. S. O. Abdul-Hay, J. Luo, R. T. Ashghodom, G. R. Thatcher, NO-flurbiprofen reduces amyloid-beta, is neuroprotective in cell culture, and enhances cognition in response to cholinergic blockade. *J Neurochem* 111, 766 (November, 2009).
51. S. Abdul-Hay et al., NO-SSRIs: Nitric Oxide Chimera Drugs Incorporating a Selective Serotonin Reuptake Inhibitor. *ACS Med Chem Lett* 2, 656 (Sep. 8, 2011).
52. Z. Qin et al., Benzothiophene selective estrogen receptor modulators with modulated oxidative activity and receptor affinity. *J Med Chem* 50, 2682 (May 31, 2007).
53. R. Abdelhamid et al., Benzothiophene Selective Estrogen Receptor Modulators Provide Neuroprotection by a novel GPR30-dependent Mechanism. *ACS Chem Neurosci* 2, 256 (May 18, 2011).
54. M. K. Dennis et al., In vivo effects of a GPR30 antagonist. *Nat Chem Biol* 5, 421 (June, 2009).
55. S. Oddo et al., Triple-transgenic model of Alzheimer's disease with plaques and tangles: intracellular Abeta and synaptic dysfunction. *Neuron* 39, 409 (Jul. 31, 2003).
56. J. Larson, G. Lynch, D. Games, P. Seubert, Alterations in synaptic transmission and long-term potentiation in hippocampal slices from young and aged PDAPP mice. *Brain Res* 840, 23 (Sep. 4, 1999).
57. J. Larson, G. Lynch, Role of N-methyl-D-aspartate receptors in the induction of synaptic potentiation by burst stimulation patterned after the hippocampal theta-rhythm. *Brain Res* 441, 111 (Feb. 16, 1988).
58. L. E. Carlson, B. B. Sherwin, Steroid hormones, memory and mood in a healthy elderly population. *Psychoneuroendocrinology* 23, 583 (August, 1998).
59. S. M. Resnick, E. J. Metter, A. B. Zonderman, Estrogen replacement therapy and longitudinal decline in visual memory. A possible protective effect? *Neurology* 49, 1491 (December, 1997).
60. K. Steenland, J. MacNeil, I. Vega, A. Levey, Recent trends in Alzheimer disease mortality in the United States, 1999 to 2004. *Alzheimer Dis Assoc Disord* 23, 165 (April-June, 2009).
61. D. B. Dubal, P. J. Shughrue, M. E. Wilson, I. Merchenthaler, P. M. Wise, Estradiol Modulates bcl-2 in Cerebral Ischemia: A Potential Role for Estrogen Receptors. *J. Neurosci.* 19, 6385 (Aug. 1, 1999, 1999).
62. P. Tanapat, N. B. Hastings, A. J. Reeves, E. Gould, Estrogen Stimulates a Transient Increase in the Number of New Neurons in the Dentate Gyrus of the Adult Female Rat. *J. Neurosci.* 19, 5792 (Jul. 15, 1999, 1999).
63. J. Zhou, H. Zhang, R. S. Cohen, S. C. Pandey, Effects of estrogen treatment on expression of brain-derived neurotrophic factor and cAMP response element-binding pro- 64. K. Yaffe et al., Effect of Raloxifene on Prevention of Dementia and Cognitive Impairment in Older Women: The Multiple Outcomes of Raloxifene Evaluation (MORE) Randomized Trial. *Am J Psychiatry* 162, 683 (Apr. 1, 2005, 2005).

65. K. Yaffe et al., Cognitive function in postmenopausal women treated with raloxifene. *N Engl J Med* 344, 1207 (Apr. 19, 2001).

66. D. E. Jacobsen, M. M. Samson, M. H. Emmelot-Vonk, H. J. Verhaar, Raloxifene improves verbal memory in late postmenopausal women: a randomized, double-blind, placebo-controlled trial. *Menopause*, (Nov. 14, 2009).

67. X. Wu et al., Raloxifene and estradiol benzoate both fully restore hippocampal choline acetyltransferase activity in ovariectomized rats. *Brain Research* 847, 98 (1999).

68. R. B. Gibbs, R. Gabor, T. Cox, D. A. Johnson, Effects of raloxifene and estradiol on hippocampal acetylcholine release and spatial learning in the rat. *Psychoneuroendocrinology* 29, 741 (2004).

69. I. Ciriza, P. Carrero, I. Azcoitia, S. G. Lundeen, L. M. Garcia-Segura, Selective estrogen receptor modulators protect hippocampal neurons from kainic acid excitotoxicity: differences with the effect of estradiol. *J Neurobiol* 61, 209 (November, 2004).

70. O. N. Kokiko, A. K. Murashov, M. R. Hoane, Administration of raloxifene reduces sensorimotor and working memory deficits following traumatic brain injury. *Behav Brain Res* 170, 233 (Jun. 30, 2006).

71. R. Goekoop et al., Raloxifene Treatment Enhances Brain Activation during Recognition of Familiar Items: a Pharmacological fMRI Study in Healthy Elderly Males. *Neuropsychopharmacology* 31, 1508 (2005).

72. R. Goekoop et al., Raloxifene exposure enhances brain activation during memory performance in healthy elderly males; its possible relevance to behavior. *NeuroImage* 25, 63 (2005).

73. E. R. Prossnitz, M. Barton, The G-protein-coupled estrogen receptor GPER in health and disease. *Nat Rev Endocrinol* 7, 715 (December, 2011).

74. R. Hammond, R. B. Gibbs, GPR30 is positioned to mediate estrogen effects on basal forebrain cholinergic neurons and cognitive performance. *Brain Res* 1379, 53 (Mar. 16, 2011).

75. J. Nilsen, S. Chen, R. D. Brinton, Dual action of estrogen on glutamate-induced calcium signaling: mechanisms requiring interaction between estrogen receptors and src/mitogen activated protein kinase pathway. *Brain Res* 930, 216 (Mar. 15, 2002).

76. J. Nilsen, R. Diaz Brinton, Mechanism of estrogen-mediated neuroprotection: regulation of mitochondrial calcium and Bcl-2 expression. *Proc Natl Acad Sci USA* 100, 2842 (Mar. 4, 2003).

77. T. W. Wu, J. M. Wang, S. Chen, R. D. Brinton, 17Beta-estradiol induced Ca2+ influx via L-type calcium channels activates the Src/ERK/cyclic-AMP response element binding protein signal pathway and BCL-2 expression in rat hippocampal neurons: a potential initiation mechanism for estrogen-induced neuroprotection. *Neuroscience* 135, 59 (2005).

78. A. Parcellier, L. A. Tintignac, E. Zhuravleva, B. A. Hemmings, PKB and the mitochondria: AKTing on apoptosis. *Cell Signal* 20, 21 (January, 2008).

79. R. Sterniczuk, M. C. Antle, F. M. Laferla, R. H. Dyck, Characterization of the 3xTg-AD mouse model of Alzheimer's disease: part 2. Behavioral and cognitive changes. *Brain Res* 1348, 149 (Aug. 12, 2010).

80. M. R. Meyer et al., Deletion of G protein-coupled estrogen receptor increases endothelial vasoconstriction. *Hypertension* 59, 507 (February, 2012).

81. Y. C. Chan et al., Raloxifene improves vascular reactivity in pressurized septal coronary arteries of ovariectomized hamsters fed cholesterol diet. *Pharmacol Res* 65, 182 (February, 2012).

82. G. A. Figtree, Y. Lu, C. M. Webb, P. Collins, Raloxifene acutely relaxes rabbit coronary arteries in vitro by an estrogen receptor-dependent and nitric oxide-dependent mechanism. *Circulation* 100, 1095 (Sep. 7, 1999).

83. R. T. Bartus, R. L. Dean, 3rd, B. Beer, A. S. Lippa, The cholinergic hypothesis of geriatric memory dysfunction. *Science* 217, 408 (Jul. 30, 1982).

84. E. J. Mufson et al., Mild cognitive impairment: pathology and mechanisms. *Acta Neuropathol* 123, 13 (January, 2012).

85. J. Buccafusco, in *Methods of Behavior Analysis in Neuroscience*, J. Buccafusco, Ed. (CRC Press, Boca Raton (Fla.), 2009).

86. S. Arlt et al., Dimethylarginines, homocysteine metabolism, and cerebrospinal fluid markers for Alzheimer's disease. *J Alzheimers Dis* 31, 751 (2012).

87. M. L. Selley, Increased (E)-4-hydroxy-2-nonenal and asymmetric dimethylarginine concentrations and decreased nitric oxide concentrations in the plasma of patients with major depression. *J Affect Disord* 80, 249 (June, 2004).

88. Y. C. Luiking, G. A. Ten Have, R. R. Wolfe, N. E. Deutz, Arginine de novo and nitric oxide production in disease states. *Am J Physiol Endocrinol Metab* 303, E1177 (November, 2012).

89. R. H. Foxton, J. M. Land, S. J. Heales, Tetrahydrobiopterin availability in Parkinson's and Alzheimer's disease; potential pathogenic mechanisms. *Neurochem Res* 32, 751 (April-May, 2007).

90. S. Cantara, P. E. Thorpe, M. Ziche, S. Donnini, TAT-BH4 counteracts Abeta toxicity on capillary endothelium. *FEBS Lett* 581, 702 (Feb. 20, 2007).

91. N. Ferlazzo et al., The 894G>T (Glu298Asp) variant in the endothelial NOS gene and MTHFR polymorphisms influence homocysteine levels in patients with cognitive decline. *Neuromolecular Med* 13, 167 (September, 2011).

92. D. M. Jans et al., Processing of amyloid precursor protein as a biochemical link between atherosclerosis and Alzheimer's disease. *Cardiovasc Hematol Disord Drug Targets* 6, 21 (March, 2006).

93. S. Taddei et al., Menopause is associated with endothelial dysfunction in women. *Hypertension* 28, 576 (October, 1996).

94. C. A. Colton et al., NO synthase 2 (NOS2) deletion promotes multiple pathologies in a mouse model of Alzheimer's disease. *Proc Natl Acad Sci USA* 103, 12867 (Aug. 22, 2006).

95. L. Ridnour et al., Nitric Oxide-Mediated Regulation of beta-Amyloid Clearance via Alterations of MMP-9/TIMP-1. *J Neurochem*, (Sep. 27, 2012).

96. H. Liu, J. Liu, R. B. van Breemen, G. R. J. Thatcher, J. L. Bolton, Bioactivation of the selective estrogen receptor modulator desmethylated arzoxifene to quinoids: 4'-fluoro substitution prevents quinoid formation. *Chem Res Toxicol* 18, 162 (February, 2005).

97. E. A. Kramar et al., Cytoskeletal changes underlie estrogen's acute effects on synaptic transmission and plasticity. *J Neurosci* 29, 12982 (Oct. 14, 2009).

98. I. T. Schiefer, L. Vandevrede, M. Fa, O. Arancio, G. R. Thatcher, Furoxans (1,2,5-Oxadiazole-N-Oxides) as Novel NO Mimetic Neuroprotective and Procognitive Agents. *J Med Chem* 55, 3076 (Apr. 12, 2012).
99. Z. Qin et al., Design and synthesis of neuroprotective methylthiazoles and modification as NO-chimeras for neurodegenerative therapy. *J Med Chem* 55, 6784 (Aug. 9, 2012).
100. H. Liu, Z. Qin, G. R. Thatcher, J. L. Bolton, Uterine peroxidase-catalyzed formation of diquinone methides from the selective estrogen receptor modulators raloxifene and desmethylated arzoxifene. *Chem Res Toxicol* 20, 1676 (November, 2007).

What is claimed is:

1. A compound having a formula of (II-i):

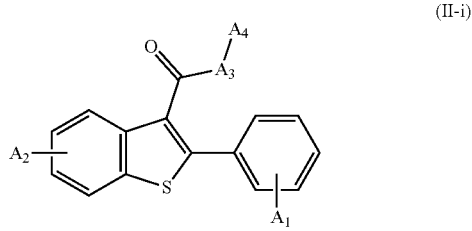

(II-i)

or a pharmaceutically acceptable salt thereof,
wherein
$A_1$ is selected from the group consisting of halogen, trifluoromethyl, and —$OR_1$;
$A_2$ is selected from the group consisting of halogen and trifluoromethyl;
$A_3$ is selected from the group consisting of alkyl, aryl, cycloalkyl, cycloalkylalkyl, heterocycle, and heteroaryl;
$A_4$ is selected from the group consisting of hydrogen, halogen, cyano, trifluoromethyl, aryl-heteroaryl wherein the aryl is substituted or unsubstituted, and —$OR_3$;
$R_1$ is selected from the group consisting of —$SO_3R^{x1}$ and —$PO_3R^{y1}R^{z1}$;
$R_3$ is selected from the group consisting of hydrogen, alkyl, —$SO_3R^{x1}$, —$PO_3R^{y1}R^{z1}$, and —$C(=O)R^a$;
$R^{x1}$, $R^{y1}$ and $R^{z1}$, at each occurrence, are independently selected from the group consisting of hydrogen and a pharmaceutically acceptable cation; and
$R^a$ is alkyl or —OH.

2. A compound selected from the group consisting of:
(2-(4-fluorophenyl)-6-hydroxybenzo[b]thiophen-3-yl)(4-(trifluoromethyl)phenyl)methanone;
(3-(4-fluorophenyl)-6-hydroxybenzo[b]thiophen-2-yl)(4-(trifluoromethyl)phenyl)methanone;
cyclopropyl(2-(4-fluorophenyl)-6-hydroxybenzo[b]thiophen-3-yl)methanone;
cyclopropyl(3-(4-fluorophenyl)-6-hydroxybenzo[b]thiophen-2-yl)methanone;
(2-(4-fluorophenyl)-6-hydroxybenzo[b]thiophen-3-yl)(pyridin-4-yl)methanone;
(3-(4-fluorophenyl)-6-hydroxybenzo[b]thiophen-2-yl)(pyridin-4-yl)methanone;
1-(2-(4-fluorophenyl)-6-hydroxybenzo[b]thiophen-3-yl)-2-methylpropan-1-one;
1-(3-(4-fluorophenyl)-6-hydroxybenzo[b]thiophen-2-yl)-2-methylpropan-1-one;
(4-ethynylphenyl)(2-(4-fluorophenyl)-6-hydroxybenzo[b]thiophen-3-yl)methanone;
(4-ethynylphenyl)(3-(4-fluorophenyl)-6-hydroxybenzo[b]thiophen-2-yl)methanone;
(3-(4-fluorophenyl)-6-hydroxybenzo[b]thiophen-2-yl)(p-tolyl)methanone;
(4-(1-(4-fluorophenyl)-1H-1,2,3-triazol-4-yl)phenyl)(2-(4-fluorophenyl)-6-hydroxybenzo[b]thiophen-3-yl)methanone;
(4-(1-(4-fluorophenyl)-1H-1,2,3-triazol-4-yl)phenyl)(3-(4-fluorophenyl)-6-hydroxybenzo[b]thiophen-2-yl)methanone;
(3r,5r,7r)-adamantan-1-yl(2-(4-fluorophenyl)-6-hydroxybenzo[b]thiophen-3-yl)methanone; and
(3r,5r,7r)-adamantan-1-yl(3-(4-fluorophenyl)-6-hydroxybenzo[b]thiophen-2-yl)methanone;
or a pharmaceutically acceptable salt thereof.

3. A compound having a formula of (II-ii):

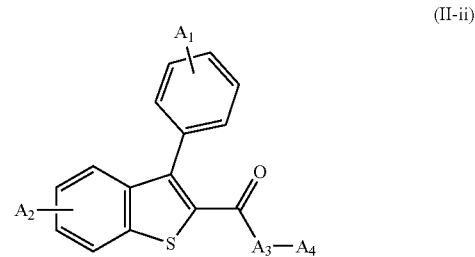

(II-ii)

or a pharmaceutically acceptable salt thereof,
wherein
$A_1$ is selected from the group consisting of halogen, trifluoromethyl, and —$OR_1$;
$A_2$ is selected from the group consisting of halogen and trifluoromethyl;
$A_3$ is selected from the group consisting of alkyl, aryl, cycloalkyl, cycloalkylalkyl, heterocycle, and heteroaryl;
$A_4$ is selected from the group consisting of hydrogen, halogen, alkyl, cyano, trifluoromethyl, aryl-heteroaryl wherein the aryl is substituted or unsubstituted, and —$OR_3$;
$R_1$, $R_2$ and $R_3$ are each independently selected from the group consisting of hydrogen, alkyl, —$SO_3R^{x1}$, —$PO_3R^{y1}R^{z1}$, and —$C(=O)R^a$;
$R^{x1}$, $R^{y1}$ and $R^{z1}$, at each occurrence, are independently selected from the group consisting of hydrogen and a pharmaceutically acceptable cation; and
$R^a$ is alkyl or —OH.

* * * * *